US012723076B2

(12) United States Patent
Shusta et al.

(10) Patent No.: US 12,723,076 B2
(45) Date of Patent: Sep. 1, 2026

(54) HUMAN BLOOD-BRAIN BARRIER TARGETING ANTIBODIES

(71) Applicant: Wisconsin Alumni Research Foundation, Madison, WI (US)

(72) Inventors: Eric V. Shusta, Madison, WI (US); Charles C. Stutz, Waltham, MA (US); Loukas Goulatis, Worcester, MA (US); Julia Georgieva, Berlin (DE)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 19/384,776

(22) Filed: Nov. 10, 2025

(65) Prior Publication Data

US 2026/0062480 A1 Mar. 5, 2026

Related U.S. Application Data

(62) Division of application No. 17/759,854, filed as application No. PCT/US2021/015466 on Jan. 28, 2021, now Pat. No. 12,492,251.

(60) Provisional application No. 62/966,860, filed on Jan. 28, 2020.

(51) Int. Cl.
*C07K 16/28* (2006.01)
*C12N 15/63* (2006.01)

(52) U.S. Cl.
CPC .............. *C07K 16/28* (2013.01); *C12N 15/63* (2013.01); *C07K 2317/24* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| | | | | |
|---|---|---|---|---|
| 8,048,992 | B2 * | 11/2011 | Kurosawa ............ | C07K 16/303 530/387.1 |
| 2009/0169561 | A1 | 7/2009 | Fischer et al. | |
| 2015/0196663 | A1 | 7/2015 | Shusta et al. | |
| 2017/0260282 | A1 | 9/2017 | Holland et al. | |
| 2021/0277108 | A1 | 9/2021 | Shusta et al. | |

FOREIGN PATENT DOCUMENTS

| | | | |
|---|---|---|---|
| CN | 1900117 | A | 1/2007 |
| WO | 2002057445 | A1 | 7/2002 |
| WO | 2007143711 | A2 | 12/2007 |
| WO | 2018007950 | A1 | 1/2018 |

OTHER PUBLICATIONS

UniProtKB Accession No. AOA4Y81313, Trk system potassium transporter TrkA. Sep. 18, 2019 [online]. [Retrieved on Jun. 8, 2021). Retrieved from the internet <URL: https://www.uniprot.org/uniproUAOA4Y81313> Full document, especially sequence.

UniProtKB Accession No. R6G1B2, Sus0-like_3 domain-containing protein. Jul. 24, 2013 [online]. [Retrieved on Jun. 8, 2021). Retrieved from the internet <URL: https://www.uniprot.org/uniproUR6G1B2> Full document, especially sequence.

International Search Report and Written Opinion issued in corresponding PCT Application No. PCT/US2021/015466, mailed Jul. 16, 2021.

Abbott, A. Friedman, Overview and introduction: the blood-brain barrier in health and disease. Epilepsia. 53 Suppl 6, 1-6 (2012).

Couch, Y. J. Yu, Y. Zhang, J. M. Tarrant, R. N. Fuji, W. J. Meilandt, H. Solanoy, R. K. Tong, K. Hoyte, W. Luk, Y. Lu, K. Gadkar, S. Prabhu, B. A. Ordonia, Q. Nguyen, Y. Lin, Z. Lin, M. Balazs, K. Scearce-Levie, J. A. Ernst, M. S. Dennis, R. J. Watts, Addressing safety liabilities of TfR bispecific antibodies that cross the blood-brain barrier. Sci. Transl. Med. 5, 183ra57, 1-12 (2013).

Farrington, N. Caram-Salas, A. S. Haqqani, E. Brunette, J. Eldredge, B. Pepinsky, G. Antognetti, E. Baumann, W. Ding, E. Garber, S. Jiang, C. Delaney, E. Boileau, W. P. Sisk, D. B. Stanimirovic, A novel platform for engineering blood-brain barrier-crossing bispecific biologics. FASEB J. 28, 4764-78 (2014).

Goulatis, E. V Shusta, Protein engineering approaches for regulating blood-brain barrier transcytosis. Curr. Opin. Struct. Biol. 45, 109-115 (2017).

Haqqani, G. Thom, M. Burrell, C. E. Delaney, E. Brunette, E. Baumann, C. Sodja, A. Jezierski, C. Webster, D. B. Stanimirovic, Intracellular sorting and transcytosis of the rat transferrin receptor antibody {OX}26 across the blood-brain barrier in vitro is dependent on its binding affinity. J. Neurochem. (2018), doi:10.1111/jnc.14482.

Johnsen, M. Bak, F. Melander, M. S. Thomsen, A. Burkhart, P. J. Kempen, T. L. Andresen, T. Moos, Modulating the antibody density changes the uptake and transport at the blood-brain barrier of both transferrin receptor-targeted gold nanoparticles and liposomal cargo. J. Control. Release. 295, 237-249 (2019).

Jones AR, Shusta EV. Blood-brain barrier transport of therapeutics via receptor-mediation. Pharm Res. Sep. 2007;24(9):1759-71.

Jones et al., Replacing the complementarity-determining regions in a human antibody with those from a mouse. Nature 321:522-525 (1986).

Jones, C. C. Stutz, Y. Zhou, J. D. Marks, E. V Shusta, Identifying blood-brain-barrier selective single-chain antibody fragments. Biotechnol. J. 9, 664-674 (2014).

Karaoglu Hanzatian, A. Schwartz, F. Gizatullin, J. Erickson, K. Deng, R. Villanueva, C. Stedman, C. Harris, T. Ghayur, A. Goodearl, Brain uptake of multivalent and multi-specific DVD-Ig proteins after systemic administration. MAbs. 10, 765-777 (2018).

(Continued)

*Primary Examiner* — Gary B Nickol

(74) *Attorney, Agent, or Firm* — Quarles & Brady LLP

(57) ABSTRACT

The present invention provides antibodies or antigen-binding fragments thereof including single chain variable fragment (scFv) antibodies that specifically bind to and translocate the blood-brain barrier and methods of use.

18 Claims, 13 Drawing Sheets

Specification includes a Sequence Listing.

(56) References Cited

OTHER PUBLICATIONS

Kurosawa, Y. Tega, K. Higuchi, T. Yamaguchi, T. Nakakura, T. Mochizuki, H. Kusuhara, K. Kawabata, Y. Deguchi, Expression and Functional Characterization of Drug Transporters in Brain Microvascular Endothelial Cells Derived from Human Induced Pluripotent Stem Cells. Mol. Pharm. 15, 5546-5555 (2018).
Li, L. Feng, L. Fan, Y. Zha, L. Guo, Q. Zhang, J. Chen, Z. Pang, Y. Wang, X. Jiang, V. C. Yang, L. Wen, Targeting the brain with PEG-PLGA nanoparticles modified with phage-displayed peptides. Biomaterials. 32, 4943-4950 (2011).
Muruganandam, J. Tanha, S. Narang, D. Stanimirovic, Selection of phage-displayed llama single-domain antibodies that transmigrate across human blood-brain barrier endothelium. FASEB J. Off. Publ. Fed. Am. Soc. Exp. Biol. 16, 240-242 (2002).
Niewoehner, B. Bohrmann, L. Collin, E. Urich, H. Sade, P. Maier, P. Rueger, J. O. Stracke, W. Lau, A. C. Tissot, H. Loetscher, A. Ghosh, P.-O. Freskgård, Increased brain penetration and potency of a therapeutic antibody using a monovalent molecular shuttle. Neuron. 81, 49-60 (2014).
Pardridge, Blood-brain barrier drug delivery of IgG fusion proteins with a transferrin receptor monoclonal antibody. Expert Opin. Drug Deliv. 12 (2015), pp. 207-222.
Pardridge, Y. S. Kang, J. L. Buciak, J. Yang, Human insulin receptor monoclonal antibody undergoes high affinity binding to human brain capillaries in vitro and rapid transcytosis through the blood-brain barrier in vivo in the primate. Pharm. Res. 12, 807-816 (1995).
Pardridge, Y. S. Kang, J. L. Buciak, Transport of human recombinant brain-derived neurotrophic factor ({BDNF}) through the rat blood-brain barrier in vivo using vector-mediated peptide drug delivery. Pharm. Res. 11, 738-746 (1994).
Pasqualini, E. Ruoslahti, Organ targeting in vivo using phage display peptide libraries. Nature. 380, 364-366 (1996).
Poduslo, G. L. Curran, C. T. Berg, Macromolecular permeability across the blood-nerve and blood-brain barriers. Proc. Natl. Acad. Sci. U. S. A. 91, 5705-5709 (1994).
Poul, B. Becerril, U. B. Nielsen, P. Morisson, J. D. Marks, Selection of tumor-specific internalizing human antibodies from phage libraries. J. Mol. Biol. 301, 1149-1161 (2000).
Presta, L.G. (1992). "Antibody Engineering," Curr. Op. Struct. Biol. 2:593-596.
Reichmann et al., Reshaping human antibodies for therapy. Nature 332:323-329 (1988).
Ribecco-Lutkiewicz, C. Sodja, J. Haukenfrers, A. S. Haqqani, D. Ly, P. Zachar, E. Baumann, M. Ball, J. Huang, M. Rukhlova, M. Martina, Q. Liu, D. Stanimirovic, A. Jezierski, M. Bani-Yaghoub, A novel human induced pluripotent stem cell blood-brain barrier model: Applicability to study antibody-triggered receptor-mediated transcytosis. Sci. Rep. 8, 1873 (2018).
Saito G, Swanson JA, Lee KD. Drug delivery strategy utilizing conjugation via reversible disulfide linkages: role and site of cellular reducing activities. Adv Drug Deliv Rev. Feb. 10, 2003;55(2):199-215.
Stutz, J. V. Georgieva, E. V. Shusta, Coupling brain perfusion screens and next generation sequencing to identify blood-brain barrier binding antibodies. AIChE J. 64 (2018), doi:10.1002/aic.16360.
Stutz, X. Zhang, E. V Shusta, Combinatorial approaches for the identification of brain drug delivery targets. Curr. Pharm. Des. 20, 1564-1576 (2014).
Sugano et al., Antibody Targeting of Doxorubicin-loaded Liposomes Suppresses the Growth and Metastatic Spread of Established Human Lung Tumor Xenografts in Severe Combined Immunodeficient Mice Cancer Research 60, 6942-6949, Dec. 15, 2000.
Sukhanova et al. Oriented conjugates of single-domain antibodies and quantum dots: toward a new generation of ultrasmall diagnostic nanoprobes. Nanomedicine. May 2012;8(4):516-25.
Takakura, M. Hashida, Macromolecular carrier systems for targeted drug delivery: Pharmacokinetic considerations on biodistribution. Pharm. Res. 13, 820-831 (1996).
Trail PA, King HD, Dubowchik GM. Monoclonal antibody drug immunoconjugates for targeted treatment of cancer. Cancer Immunol Immunother. May 2003;52(5):328-37.
Umlauf, P. A. Clark, J. M. Lajoie, J. V. Georgieva, S. Bremner, B. R. Herrin, J. S. Kuo, E. V. Shusta, Identification of variable lymphocyte receptors that can target therapeutics to pathologically exposed brain extracellular matrix. Sci. Adv. 5 (2019), doi:10.1126/sciadv.aau4245.
Urich, R. Schmucki, N. Ruderisch, E. Kitas, U. Certa, H. Jacobsen, C. Schweitzer, A. Bergadano, M. Ebeling, H. Loetscher, P. O. Freskgård, Cargo Delivery into the Brain by in vivo identified Transport Peptides. Sci. Rep. 5, 14104 (2015).
Van de Broek B, Devoogdt N, D'Hollander A, Gijs HL, Jans K, Lagae L, Muyldermans S, Maes G, Borghs G. Specific cell targeting with nanobody conjugated branched gold nanoparticles for photothermal therapy. ACS Nano. Jun. 28, 2011;5(6):4319-28.
Wang, Y. K. Cho, E. V Shusta, Mining a yeast library for brain endothelial cell-binding antibodies. Nat. Methods. 4, 143-145 (2007).
Webster, N. Caram-Salas, A. S. Haqqani, G. Thom, L. Brown, K. Rennie, A. Yogi, W. Costain, E. Brunette, D. B. Stanimirovic, Brain penetration, target engagement, and disposition of the blood-brain barrier-crossing bispecific antibody antagonist of metabotropic glutamate receptor type 1. FASEB J. 30, 1927-1940 (2016).
Wu AM, Senter PD. Arming antibodies: prospects and challenges for immunoconjugates. Nat Biotechnol. Sep. 2005;23(9):1137-46.
Ye Z, Gastfriend BD, Umlauf BJ, Lynn DM, Shusta EV. Antibody-Targeted Liposomes for Enhanced Targeting of the Blood-Brain Barrier. Pharm Res. Jul. 2022;39(7):1523-1534. doi: 10.1007/s11095-022-03186-1. Epub Feb. 15, 2022. PMID: 35169958; PMCID: PMC9250590.
Yu, J. K. Atwal, Y. Zhang, R. K. Tong, K. R. Wildsmith, C. Tan, N. Bien-Ly, M. Hersom, J. A. Maloney, W. J. Meilandt, D. Bumbaca, K. Gadkar, K. Hoyte, W. Luk, Y. Lu, J. A. Ernst, K. Scearce-Levie, J. A. Couch, M. S. Dennis, R. J. Watts, Therapeutic bispecific antibodies cross the blood-brain barrier in nonhuman primates. Sci. Transl. Med. 6, 261ra154 (2014).
Yu, Y. Zhang, M. Kenrick, K. Hoyte, W. Luk, Y. Lu, J. Atwal, J. M. Elliott, S. Prabhu, R. J. Watts, M. S. Dennis, Boosting brain uptake of a therapeutic antibody by reducing its affinity for a transcytosis target. Sci. Transl. Med. 3, 84ra44 (2011).
Zhou Y, Marks JD. Identification of target and function specific antibodies for effective drug delivery. Methods Mol Biol. 2009;525:145-60, xv.
Zorniak, P. A. Clark, B. J. Umlauf, Y. Cho, E. V Shusta, J. S. Kuo, Yeast display biopanning identifies human antibodies targeting glioblastoma stem-like cells. Sci. Rep. 7, 15840 (2017).
Zuchero, X. Chen, N. Bien-Ly, D. Bumbaca, R. K. Tong, X. Gao, S. Zhang, K. Hoyte, W. Luk, M. A. Huntley, L. Phu, C. Tan, D. Kallop, R. M. Weimer, Y. Lu, D. S. Kirkpatrick, J. A. Ernst, B. Chih, M. S. Dennis, R. J. Watts, Discovery of Novel Blood-Brain Barrier Targets to Enhance Brain Uptake of Therapeutic Antibodies. Neuron. 89, 70-82 (2016).

* cited by examiner

Phage-displayed human scFv library (1) Presubtraction on human heart and lung endothelial cells supernatant (2) Binding and internalization into BMECs (3) i / ii blood side brain side Transcytosis of phage particles at 37°C for 3hrs
i: without scFv blocking
ii: with scFv blocking Sequencing of recovered phage

B)

| TEER (ohm-cm$^2$) | Total CFU Brain side |
|---|---|
| 140 | $4.9x10^7$ |
| 168 | $1.12x10^6$ |
| 403 | $5.4x10^3$ |
| 712 | $1.24x10^3$ |
| 1302 | 812 |
| 1905 | 205 |

C)

R3
R2
R1
Non-binding phage

Count

Fluorescence

D)

Non-binding clone

Binding clone

| Clone | Kd [nM] | 95% CI |
|---|---|---|
| 3 | 52 | (30, 74) |
| 9 | 44 | (27, 60) |
| 17 | 28 | (19, 36) |
| 26 | 38 | (29, 47) |
| 46.1 | 153 | (128, 179) |

merge | scFv-Fc | GFAP 3-scFv-Fc 17-scFv-Fc 26-scFv-Fc 46.1-scFv-Fc

Ctrl-Fc

| Clone | Ctrl-Fc | 46.1-scFv-Fc | 17-scFv-Fc |
|---|---|---|---|
| Brain concentration [nM] | 0.31 ± 0.11 | 8.1† ± 1.2 | 2.79* ± 0.63 |
| Plasma concentration [nM] | 1970 ± 130 | 1150 ± 100 | 940 ± 90 |
| Brain to plasma ratio (%) | 0.015 ± 0.004 | 0.72† ± 0.152 | 0.28† ± 0.045 |

FIG. 6

17-scFv 9-scFv 3-scFv

Ctrl-scFv 46.1-scFv 26-scFv

22Ch-scFv

FIG. 7 antibody
antibody + rIR
antibody + rhTFR
Relative binding signal (AU)
0
1
2
3
46.1
17
anti-TFR
anti-IR
*
*
*
*

FIG. 10
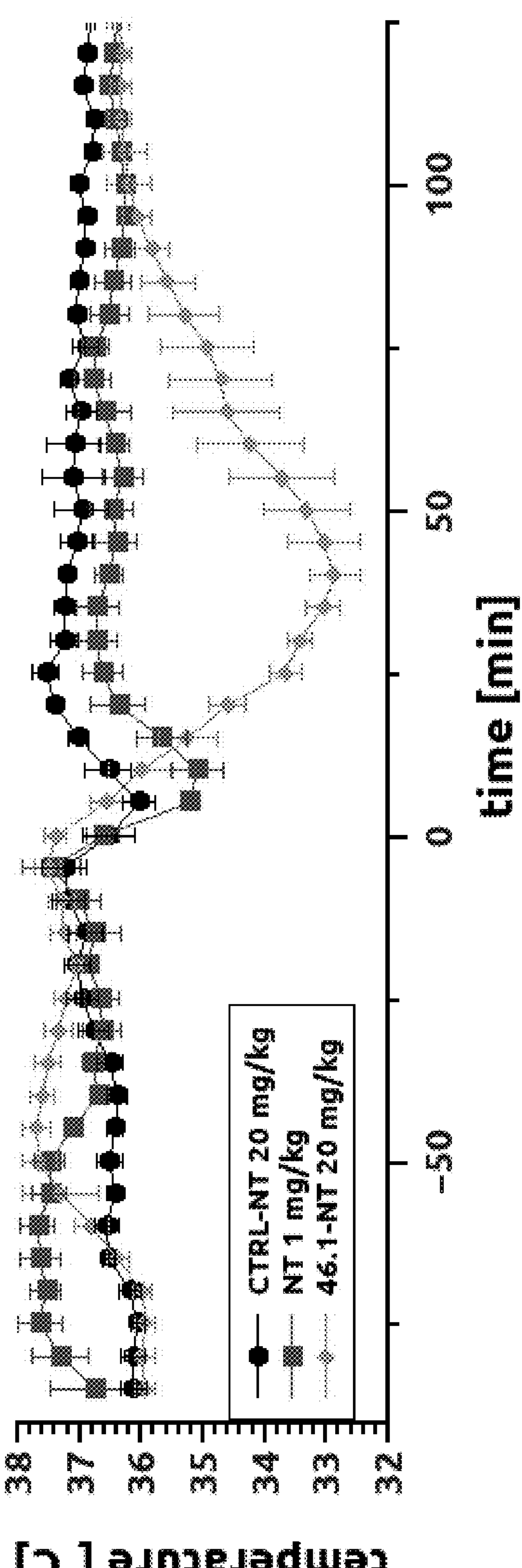
temperature [°C]
38
37
36
35
34
33
32
time [min]
−50
0
50
100
CTRL-NT 20 mg/kg
NT 1 mg/kg
46.1-NT 20 mg/kg

SEQUENCE LISTING

```
Sequence total quantity: 74
SEQ ID NO: 1            moltype = AA  length = 245
FEATURE                 Location/Qualifiers
```

```
REGION                  1..245
                        note = Synthetic - scFv3
source                  1..245
                        mol_type = protein
                        organism = synthetic construct
SEQUENCE: 1
QVQLQESGGG VVQPGRSLRL SCAASGFTFS SYAMHWVRQA PGKGLEWVAV ISYDGSNKYY  60
ADSVKGRFTI SRDNSKNTLY LQMNSLRAED TAVYYCARDS KGQSVRNRFD PWGQGTLVTV  120
SSGGGGSGGG GSGGGGSSEL TQDPAVSVAL GQTVRITCQG DNLRSYYASW YQQRPGQAPI  180
LVLYANTHRP SSIPDRFSGS SSGNTASLTI TGAQAEDEAD YYCNSRDSSG NLVVFGGGTK  240
LTVLG                                                              245

SEQ ID NO: 2            moltype = AA  length = 8
FEATURE                 Location/Qualifiers
REGION                  1..8
                        note = Synthetic - scFv3CDRH1
source                  1..8
                        mol_type = protein
                        organism = synthetic construct
SEQUENCE: 2
GFTFSSYA                                                           8

SEQ ID NO: 3            moltype = AA  length = 8
FEATURE                 Location/Qualifiers
REGION                  1..8
                        note = Synthetic - scFv3CDRH2
source                  1..8
                        mol_type = protein
                        organism = synthetic construct
SEQUENCE: 3
ISYDGSNK                                                           8

SEQ ID NO: 4            moltype = AA  length = 15
FEATURE                 Location/Qualifiers
REGION                  1..15
                        note = Synthetic - scFv3CDRH3
source                  1..15
                        mol_type = protein
                        organism = synthetic construct
SEQUENCE: 4
ARDSKGQSVR NRFDP                                                   15

SEQ ID NO: 5            moltype = AA  length = 6
FEATURE                 Location/Qualifiers
REGION                  1..6
                        note = Synthetic - scFv3CDRL1
source                  1..6
                        mol_type = protein
                        organism = synthetic construct
SEQUENCE: 5
NLRSYY                                                             6

SEQ ID NO: 6            moltype = AA  length = 11
FEATURE                 Location/Qualifiers
REGION                  1..11
                        note = Synthetic - scFv3CDRL3
source                  1..11
                        mol_type = protein
                        organism = synthetic construct
SEQUENCE: 6
NSRDSSGNLV V                                                       11

SEQ ID NO: 7            moltype = AA  length = 239
FEATURE                 Location/Qualifiers
REGION                  1..239
                        note = Synthetic - scFv9
source                  1..239
                        mol_type = protein
                        organism = synthetic construct
SEQUENCE: 7
QVQLVESGGG VTQPGLSLRL SCAASGFTFS SYAMSWVRQA PGKGLEWVSA ISGSGGSTYY  60
ADSVKGRFTI SRDNSKNTLY LQMNSLRAED TAVYYCARGW KYFDYWGQGT LVTVSSSGGG  120
SGGGGSGGGG SETTLTQSPS TLSASIGDRV AITCRASEGI YHWLAWYQQK PGKAPKLLIY  180
KASSLASGAP SRFSGSGSGT DFTLTISSLQ PDDFATYYCQ QYHTISRTFG PGTKVEIKR   239

SEQ ID NO: 8            moltype = AA  length = 8
FEATURE                 Location/Qualifiers
REGION                  1..8
                        note = Synthetic - scFv9CDRH1
```

```
source                 1..8
                       mol_type = protein
                       organism = synthetic construct
SEQUENCE: 8
GFTFSSYA                                                    8

SEQ ID NO: 9           moltype = AA  length = 8
FEATURE                Location/Qualifiers
REGION                 1..8
                       note = Synthetic - scFv9CDRH2
source                 1..8
                       mol_type = protein
                       organism = synthetic construct
SEQUENCE: 9
ISGSGGST                                                    8

SEQ ID NO: 10          moltype = AA  length = 9
FEATURE                Location/Qualifiers
REGION                 1..9
                       note = Synthetic - scFv9CDRH3
source                 1..9
                       mol_type = protein
                       organism = synthetic construct
SEQUENCE: 10
ARGWKYFDY                                                   9

SEQ ID NO: 11          moltype = AA  length = 6
FEATURE                Location/Qualifiers
REGION                 1..6
                       note = Synthetic - scFv9CDRL1
source                 1..6
                       mol_type = protein
                       organism = synthetic construct
SEQUENCE: 11
EGIYHW                                                      6

SEQ ID NO: 12          moltype = AA  length = 9
FEATURE                Location/Qualifiers
REGION                 1..9
                       note = Synthetic - scFv9CDRL3
source                 1..9
                       mol_type = protein
                       organism = synthetic construct
SEQUENCE: 12
QQYHTISRT                                                   9

SEQ ID NO: 13          moltype = AA  length = 243
FEATURE                Location/Qualifiers
REGION                 1..243
                       note = Synthetic - scFv17
source                 1..243
                       mol_type = protein
                       organism = synthetic construct
SEQUENCE: 13
QVQLLQSAGA LVQPGGSLRL SCAASGFTFS SSTMHWVRQA PGKGLEWVAV VSYDGNTQYY  60
ADSVKGRFTI SRDNSKNTLS LQMNNLRAED TAVYYCAGLW GSLLGYFQHW GQGTLVTVSS  120
GGGGSGGGGS GGGGSDIQMT QSPSFLSASV GDRVTITCRA SQGVNNYLAW YQQKPGKAPK  180
LLIYAASTLQ SGVPSSFSGS GSGTEFTLTI SSLQPEDFAT YFCQQAHSFP PTFGGGTKLE  240
IKR                                                         243

SEQ ID NO: 14          moltype = AA  length = 8
FEATURE                Location/Qualifiers
REGION                 1..8
                       note = Synthetic - scFv17CDRH1
source                 1..8
                       mol_type = protein
                       organism = synthetic construct
SEQUENCE: 14
GFTFSSST                                                    8

SEQ ID NO: 15          moltype = AA  length = 8
FEATURE                Location/Qualifiers
REGION                 1..8
                       note = Synthetic - scFv17CDRH2
source                 1..8
                       mol_type = protein
                       organism = synthetic construct
SEQUENCE: 15
VSYDGNTQ                                                    8
```

```
SEQ ID NO: 16          moltype = AA  length = 13
FEATURE                Location/Qualifiers
REGION                 1..13
                       note = Synthetic - scFv17CDRH3
source                 1..13
                       mol_type = protein
                       organism = synthetic construct
SEQUENCE: 16
AGLWGSLLGY FQH                                                    13

SEQ ID NO: 17          moltype = AA  length = 6
FEATURE                Location/Qualifiers
REGION                 1..6
                       note = Synthetic - scFv17CDRL1
source                 1..6
                       mol_type = protein
                       organism = synthetic construct
SEQUENCE: 17
QGVNNY                                                            6

SEQ ID NO: 18          moltype = AA  length = 9
FEATURE                Location/Qualifiers
REGION                 1..9
                       note = Synthetic - scFv17CDRL3
source                 1..9
                       mol_type = protein
                       organism = synthetic construct
SEQUENCE: 18
QQAHSFPPT                                                         9

SEQ ID NO: 19          moltype = AA  length = 239
FEATURE                Location/Qualifiers
REGION                 1..239
                       note = Synthetic - scFv26
source                 1..239
                       mol_type = protein
                       organism = synthetic construct
SEQUENCE: 19
QVELVESGGG LVQPGGSLRL SCAASGFTFS TYWMNWVRQA PGKGLEWVAI INQDGTAEYY  60
VDSVEGRFTI SRDNAKNSLY LQMTSLRVED TAVYYCATPT GDSDYWGQGT LVTVSSGGGG  120
SGGGGSGGGG SSELTQDPAV SVALGQTVRI TCQGDSLRSY YATWYQQKPG QAPVAVIYGQ  180
NNRPSGIPDR FSGSNSGNTA SLTITAALAE DEADYYCHSR DSSGNHVLFG GGTKLTVLG   239

SEQ ID NO: 20          moltype = AA  length = 8
FEATURE                Location/Qualifiers
REGION                 1..8
                       note = Synthetic - scFv26CDRH1
source                 1..8
                       mol_type = protein
                       organism = synthetic construct
SEQUENCE: 20
GFTFSTYW                                                          8

SEQ ID NO: 21          moltype = AA  length = 8
FEATURE                Location/Qualifiers
REGION                 1..8
                       note = Synthetic - scFv26CDRH2
source                 1..8
                       mol_type = protein
                       organism = synthetic construct
SEQUENCE: 21
INQDGTAE                                                          8

SEQ ID NO: 22          moltype = AA  length = 9
FEATURE                Location/Qualifiers
REGION                 1..9
                       note = Synthetic - scFv26CDRH3
source                 1..9
                       mol_type = protein
                       organism = synthetic construct
SEQUENCE: 22
ATPTGDSDY                                                         9

SEQ ID NO: 23          moltype = AA  length = 6
FEATURE                Location/Qualifiers
REGION                 1..6
                       note = Synthetic - scFv26CDRL1
source                 1..6
```

```
                      mol_type = protein
                      organism = synthetic construct
SEQUENCE: 23
SLRSYY                                                                    6

SEQ ID NO: 24         moltype = AA  length = 11
FEATURE               Location/Qualifiers
REGION                1..11
                      note = Synthetic - scFv26CDRL3
source                1..11
                      mol_type = protein
                      organism = synthetic construct
SEQUENCE: 24
HSRDSSGNHV L                                                              11

SEQ ID NO: 25         moltype = AA  length = 243
FEATURE               Location/Qualifiers
REGION                1..243
                      note = Synthetic - scFv46.1
source                1..243
                      mol_type = protein
                      organism = synthetic construct
SEQUENCE: 25
QVQLQESGGG LAQPGGSLRL SCAASGFTFS GYWMHWVRQA PGKGLVWVSR IKGDGTDIEY  60
ADSVKGRFTI SRDNAKNTLY LQMNSLRAED TAVYYCARDL RQTHWFDSWG QGTLVTVSSG  120
GGGSGGGGSG GGGSQSALTQ DPAVSVALGQ TVRITCQGDS LRSYYASWYQ QKPGQAPVLV  180
MYGENSRPSG IPDRFSGSNS GNTASLIITG AQAEDEADYY CSSRDTSGNH VLFGGGTKLT  240
VLG                                                                       243

SEQ ID NO: 26         moltype = AA  length = 8
FEATURE               Location/Qualifiers
REGION                1..8
                      note = Synthetic - scFv46.1CDRH1
source                1..8
                      mol_type = protein
                      organism = synthetic construct
SEQUENCE: 26
GFTFSGYW                                                                  8

SEQ ID NO: 27         moltype = AA  length = 8
FEATURE               Location/Qualifiers
REGION                1..8
                      note = Synthetic - scFv46.1CDRH2
source                1..8
                      mol_type = protein
                      organism = synthetic construct
SEQUENCE: 27
IKGDGTDI                                                                  8

SEQ ID NO: 28         moltype = AA  length = 12
FEATURE               Location/Qualifiers
REGION                1..12
                      note = Synthetic - scFv46.1CDRH3
source                1..12
                      mol_type = protein
                      organism = synthetic construct
SEQUENCE: 28
ARDLRQTHWF DS                                                             12

SEQ ID NO: 29         moltype = AA  length = 6
FEATURE               Location/Qualifiers
REGION                1..6
                      note = Synthetic - scFv46.1CDRL1
source                1..6
                      mol_type = protein
                      organism = synthetic construct
SEQUENCE: 29
SLRSYY                                                                    6

SEQ ID NO: 30         moltype = AA  length = 11
FEATURE               Location/Qualifiers
REGION                1..11
                      note = Synthetic - scFv46.1CDRL3
source                1..11
                      mol_type = protein
                      organism = synthetic construct
SEQUENCE: 30
SSRDTSGNHV L                                                              11
```

-continued

```
SEQ ID NO: 31          moltype = AA  length = 239
FEATURE                Location/Qualifiers
REGION                 1..239
                       note = Synthetic - scFv6i
source                 1..239
                       mol_type = protein
                       organism = synthetic construct
SEQUENCE: 31
QVQLVESGGG LVQPGGSLRL SCAASGFTFS TYWMNWVRQA PGKGLEWVAI INQDGTAEYY  60
VDSVEGRFTI SRDNAKNSLY LQMTSLRVED TAVYYCATPT GDSDYWGQGT LVTVSSGGGG  120
SGGGGSGGGG SDIQMTQSPS TLSASIGDRV TITCQASQDI GNYLNWYQQK PGEAPKLLIY  180
DASHLETGVP SRFSGSGSGT EFTLTITGLQ PEDFATYYCQ KLSSYPLTFG GGTKLEIKR   239

SEQ ID NO: 32          moltype = AA  length = 8
FEATURE                Location/Qualifiers
REGION                 1..8
                       note = Synthetic - scFv6iCDRH1
source                 1..8
                       mol_type = protein
                       organism = synthetic construct
SEQUENCE: 32
GFTFSTYW                                                           8

SEQ ID NO: 33          moltype = AA  length = 8
FEATURE                Location/Qualifiers
REGION                 1..8
                       note = Synthetic - scFv6iCDRH2
source                 1..8
                       mol_type = protein
                       organism = synthetic construct
SEQUENCE: 33
INQDGTAE                                                           8

SEQ ID NO: 34          moltype = AA  length = 9
FEATURE                Location/Qualifiers
REGION                 1..9
                       note = Synthetic - scFv6iCDRH3
source                 1..9
                       mol_type = protein
                       organism = synthetic construct
SEQUENCE: 34
ATPTGDSDY                                                          9

SEQ ID NO: 35          moltype = AA  length = 6
FEATURE                Location/Qualifiers
REGION                 1..6
                       note = Synthetic - scFv6iCDRL1
source                 1..6
                       mol_type = protein
                       organism = synthetic construct
SEQUENCE: 35
QDIGNY                                                             6

SEQ ID NO: 36          moltype = AA  length = 9
FEATURE                Location/Qualifiers
REGION                 1..9
                       note = Synthetic - scFv6iCDRL3
source                 1..9
                       mol_type = protein
                       organism = synthetic construct
SEQUENCE: 36
QKLSSYPLT                                                          9

SEQ ID NO: 37          moltype = AA  length = 244
FEATURE                Location/Qualifiers
REGION                 1..244
                       note = Synthetic - scFv5A
SITE                   240
                       note = MISC_FEATURE - Xaa is any amino acid residue
source                 1..244
                       mol_type = protein
                       organism = synthetic construct
SEQUENCE: 37
QVQLVESGGG LVQPGGSLRL SCAASGFTFS NYAMTWVRQA PGKGLEWVSA ISGSGSSTYY  60
ADSVKGRFTI SRDNSKNTLY LQMNSLRAED TAVYYCAKTS GWPYYFDYWG QGTLVTVSSG  120
GGGSGGGGSG GGGSQSVLTQ PPSVSAAPGQ KVTISCSGSS SNIGNNYVSW YQQFPGAAPK  180
LLIYDNNKRP SGIPDRFSGS KSGTSATLGI TGLQTGDEAD YYCCSYAGSS TLVFGGGTKX  240
DRPR                                                               244
```

-continued

```
SEQ ID NO: 38            moltype = AA  length = 8
FEATURE                  Location/Qualifiers
REGION                   1..8
                         note = Synthetic - scFv5ACDRH1
source                   1..8
                         mol_type = protein
                         organism = synthetic construct
SEQUENCE: 38
GFTFSNYA                                                                  8

SEQ ID NO: 39            moltype = AA  length = 8
FEATURE                  Location/Qualifiers
REGION                   1..8
                         note = Synthetic - scFv5ACDRH2
source                   1..8
                         mol_type = protein
                         organism = synthetic construct
SEQUENCE: 39
ISGSGSST                                                                  8

SEQ ID NO: 40            moltype = AA  length = 12
FEATURE                  Location/Qualifiers
REGION                   1..12
                         note = Synthetic - scFv5ACDRH3
source                   1..12
                         mol_type = protein
                         organism = synthetic construct
SEQUENCE: 40
AKTSGWPYYF DY                                                             12

SEQ ID NO: 41            moltype = AA  length = 8
FEATURE                  Location/Qualifiers
REGION                   1..8
                         note = Synthetic - scFv5ACDRL1
source                   1..8
                         mol_type = protein
                         organism = synthetic construct
SEQUENCE: 41
SSNIGNNY                                                                  8

SEQ ID NO: 42            moltype = AA  length = 10
FEATURE                  Location/Qualifiers
REGION                   1..10
                         note = Synthetic - scFv5ACDRL3
source                   1..10
                         mol_type = protein
                         organism = synthetic construct
SEQUENCE: 42
CSYAGSSTLV                                                                10

SEQ ID NO: 43            moltype = AA  length = 242
FEATURE                  Location/Qualifiers
REGION                   1..242
                         note = Synthetic - scFv2F
source                   1..242
                         mol_type = protein
                         organism = synthetic construct
SEQUENCE: 43
QVQLQESGGG LVQPGGSLRL SCAASGFTFS SYAMTWVRQV PGKGLEWVST VSGTGVSTYY  60
ADSVKGRFTI SRDNSKNTLY LQMNSLRAED TAIYYCARGL DWKSTPIDYW GQGTLVTVSS  120
GGGGSGGGGS GGGGSEIVLT QSPSTLSASV GDRVTITCRA SQSISGWLAW YQQKPGKAPK  180
LLIYGASSLQ SGVPSRFSGS GSGTDFTLTI SGPQPEDSAT YYCLQDYNGW TFGQGTKVEI  240
KR                                                                242

SEQ ID NO: 44            moltype = AA  length = 8
FEATURE                  Location/Qualifiers
REGION                   1..8
                         note = Synthetic - scFv2FCDRH1
source                   1..8
                         mol_type = protein
                         organism = synthetic construct
SEQUENCE: 44
GFTFSSYA                                                                  8

SEQ ID NO: 45            moltype = AA  length = 8
FEATURE                  Location/Qualifiers
REGION                   1..8
                         note = Synthetic - scFv2FCDRH2
source                   1..8
```

```
                        mol_type = protein
                        organism = synthetic construct
SEQUENCE: 45
VSGTGVST                                              8

SEQ ID NO: 46           moltype = AA  length = 13
FEATURE                 Location/Qualifiers
REGION                  1..13
                        note = Synthetic - scFv2FCDRH3
source                  1..13
                        mol_type = protein
                        organism = synthetic construct
SEQUENCE: 46
ARGLDWKSTP IDY                                        13

SEQ ID NO: 47           moltype = AA  length = 6
FEATURE                 Location/Qualifiers
REGION                  1..6
                        note = Synthetic - scFv2FCDRL1
source                  1..6
                        mol_type = protein
                        organism = synthetic construct
SEQUENCE: 47
QSISGW                                                6

SEQ ID NO: 48           moltype = AA  length = 8
FEATURE                 Location/Qualifiers
REGION                  1..8
                        note = Synthetic - scFv2FCDRL3
source                  1..8
                        mol_type = protein
                        organism = synthetic construct
SEQUENCE: 48
LQDYNGWT                                              8

SEQ ID NO: 49           moltype = AA  length = 245
FEATURE                 Location/Qualifiers
REGION                  1..245
                        note = Synthetic - scFv4B
source                  1..245
                        mol_type = protein
                        organism = synthetic construct
SEQUENCE: 49
QVQLQESGGG LIQPGGSLRL SCAASGFTVS SNYMSWVRQA PGKGLEWVAN IKQDGSEKYY  60
VDSVKDRFTI SRDNAKNSLD LQMNSLRAED TALYYCARGG EEKNSGYYGD YWGQGTLVTV  120
SSGGGGSGGG GSGGGGSSEL TQDPAVSVAV GQTVKITCQG DSLRSYYASW YRQKPGQSPV  180
LVIYQDSKRP SGIPERFSGS NSGNTATLTI SGTQAMDEAN YYCQAWDSST AHYVFGTGTK  240
VTVLG                                                 245

SEQ ID NO: 50           moltype = AA  length = 8
FEATURE                 Location/Qualifiers
REGION                  1..8
                        note = Synthetic - scFv4BCDRH1
source                  1..8
                        mol_type = protein
                        organism = synthetic construct
SEQUENCE: 50
GFTVSSNY                                              8

SEQ ID NO: 51           moltype = AA  length = 8
FEATURE                 Location/Qualifiers
REGION                  1..8
                        note = Synthetic - scFv4BCDRH2
source                  1..8
                        mol_type = protein
                        organism = synthetic construct
SEQUENCE: 51
IKQDGSEK                                              8

SEQ ID NO: 52           moltype = AA  length = 15
FEATURE                 Location/Qualifiers
REGION                  1..15
                        note = Synthetic - scFv4BCDRH3
source                  1..15
                        mol_type = protein
                        organism = synthetic construct
SEQUENCE: 52
ARGGEEKNSG YYGDY                                      15
```

```
SEQ ID NO: 53           moltype = AA  length = 6
FEATURE                 Location/Qualifiers
REGION                  1..6
                        note = Synthetic - scFv4BCDRL1
source                  1..6
                        mol_type = protein
                        organism = synthetic construct
SEQUENCE: 53
SLRSYY                                                                    6

SEQ ID NO: 54           moltype = AA  length = 11
FEATURE                 Location/Qualifiers
REGION                  1..11
                        note = Synthetic - scFv4BCDRL3
source                  1..11
                        mol_type = protein
                        organism = synthetic construct
SEQUENCE: 54
QAWDSSTAHY V                                                              11

SEQ ID NO: 55           moltype = AA  length = 240
FEATURE                 Location/Qualifiers
REGION                  1..240
                        note = Synthetic - scFv5E-0.4
source                  1..240
                        mol_type = protein
                        organism = synthetic construct
SEQUENCE: 55
QVQLQESGGG LVQPGGSLRL SCSASGFTFS SYVMGWVRQA PGKGLEWVSA ISGSGGSTYY  60
ADSVKGRFTI SRDNSKNTVY LQMNSLRAED TAVYYCAKQN WYFDLWGRGT LVTVSSGGGG  120
SGGGGSGGGG SSELTQDPAV SVALGQTVRI TCQGDSLRSY YASWYQQKPG QAPVLVIYGE  180
NSRPSGIPDR FSGSSSGNTA SLTITGAQAE DEADYYCNSR DSRGTHLEVF GGRTKLTVLG  240

SEQ ID NO: 56           moltype = AA  length = 8
FEATURE                 Location/Qualifiers
REGION                  1..8
                        note = Synthetic - scFv5E-0.4CDRH1
source                  1..8
                        mol_type = protein
                        organism = synthetic construct
SEQUENCE: 56
GFTFSSYV                                                                  8

SEQ ID NO: 57           moltype = AA  length = 8
FEATURE                 Location/Qualifiers
REGION                  1..8
                        note = Synthetic - scFv5E-0.4CDRH2
source                  1..8
                        mol_type = protein
                        organism = synthetic construct
SEQUENCE: 57
ISGSGGST                                                                  8

SEQ ID NO: 58           moltype = AA  length = 9
FEATURE                 Location/Qualifiers
REGION                  1..9
                        note = Synthetic - scFv5E-0.4CDRH3
source                  1..9
                        mol_type = protein
                        organism = synthetic construct
SEQUENCE: 58
AKQNWYFDL                                                                 9

SEQ ID NO: 59           moltype = AA  length = 6
FEATURE                 Location/Qualifiers
REGION                  1..6
                        note = Synthetic - scFv5E-0.4CDRL1
source                  1..6
                        mol_type = protein
                        organism = synthetic construct
SEQUENCE: 59
SLRSYY                                                                    6

SEQ ID NO: 60           moltype = AA  length = 12
FEATURE                 Location/Qualifiers
REGION                  1..12
                        note = Synthetic - scFv5E-0.4CDRL3
source                  1..12
                        mol_type = protein
```

```
                        organism = synthetic construct
SEQUENCE: 60
NSRDSRGTHL EV                                                         12

SEQ ID NO: 61           moltype = AA  length = 245
FEATURE                 Location/Qualifiers
REGION                  1..245
                        note = Synthetic - scFvB3-R3
source                  1..245
                        mol_type = protein
                        organism = synthetic construct
SEQUENCE: 61
QVQLVESGGG VVQPGRSLRL SCAASGFTFS SYAMSWVRQA PGKGLEWVSA ISGSGGSTYY  60
ADSVMGRFTI SRDNSKNTLY LQMDSLRAED TAVYYCAKSQ GWAGDFDFWG RGTLVTVSSG  120
GGGSGGGGSG GGGSQSALTQ PPSASGSPGQ SVTISCTGTS SDIGTYNYVS WYQQRPGYAP  180
KLMIYEVNKR PSGVPDRFSG SKSGNTASLT ISGLQAEDEA EYHCCSYAGS STLVFGGGTK  240
LTVLG                                                                 245

SEQ ID NO: 62           moltype = AA  length = 8
FEATURE                 Location/Qualifiers
REGION                  1..8
                        note = Synthetic - scFvB3-R3CDRH1
source                  1..8
                        mol_type = protein
                        organism = synthetic construct
SEQUENCE: 62
GFTFSSYA                                                              8

SEQ ID NO: 63           moltype = AA  length = 8
FEATURE                 Location/Qualifiers
REGION                  1..8
                        note = Synthetic - scFvB3-R3CDRH2
source                  1..8
                        mol_type = protein
                        organism = synthetic construct
SEQUENCE: 63
ISGSGGST                                                              8

SEQ ID NO: 64           moltype = AA  length = 12
FEATURE                 Location/Qualifiers
REGION                  1..12
                        note = Synthetic - scFvB3-R3CDRH3
source                  1..12
                        mol_type = protein
                        organism = synthetic construct
SEQUENCE: 64
AKSQGWAGDF DF                                                         12

SEQ ID NO: 65           moltype = AA  length = 9
FEATURE                 Location/Qualifiers
REGION                  1..9
                        note = Synthetic - scFvB3-R3CDRL1
source                  1..9
                        mol_type = protein
                        organism = synthetic construct
SEQUENCE: 65
SSDIGTYNY                                                             9

SEQ ID NO: 66           moltype = AA  length = 10
FEATURE                 Location/Qualifiers
REGION                  1..10
                        note = Synthetic - scFvB3-R3CDRL3
source                  1..10
                        mol_type = protein
                        organism = synthetic construct
SEQUENCE: 66
CSYAGSSTLV                                                            10

SEQ ID NO: 67           moltype = AA  length = 248
FEATURE                 Location/Qualifiers
REGION                  1..248
                        note = Synthetic - scFv22Ch
source                  1..248
                        mol_type = protein
                        organism = synthetic construct
SEQUENCE: 67
QVQLQESGGG VVQPGGSLRL SCSASGFTFS SYAMHWVRQA PGKGLEYVSA ISSNGAITYY  60
ADSVKGRFTI SRDNSKNTLY LQMSSLSAED TAVYYCVKDL KPSSWPPIYF DYWGQGTLVT  120
VSSGGGGSGG GGSGGGGSQS VLTQDPAVSV ALGQTVKITC QGDSLRTYYA SWYQQRPGQA  180
```

```
PILVLYANTH RPSSIPDRFS GSSSGTTASL TITGAQAEDE ADYYCNSRDS SGNHHVVFGG  240
GTKLTVLG                                                          248

SEQ ID NO: 68          moltype = AA  length = 8
FEATURE                Location/Qualifiers
REGION                 1..8
                       note = Synthetic - scFv22ChCDRH1
source                 1..8
                       mol_type = protein
                       organism = synthetic construct
SEQUENCE: 68
GFTFSSYA                                                          8

SEQ ID NO: 69          moltype = AA  length = 8
FEATURE                Location/Qualifiers
REGION                 1..8
                       note = Synthetic - scFv22ChCDRH2
source                 1..8
                       mol_type = protein
                       organism = synthetic construct
SEQUENCE: 69
ISSNGAIT                                                          8

SEQ ID NO: 70          moltype = AA  length = 16
FEATURE                Location/Qualifiers
REGION                 1..16
                       note = Synthetic - scFv22ChCDRH3
source                 1..16
                       mol_type = protein
                       organism = synthetic construct
SEQUENCE: 70
VKDLKPSSWP PIYFDY                                                 16

SEQ ID NO: 71          moltype = AA  length = 6
FEATURE                Location/Qualifiers
REGION                 1..6
                       note = Synthetic - scFv22ChCDRL1
source                 1..6
                       mol_type = protein
                       organism = synthetic construct
SEQUENCE: 71
SLRTYY                                                            6

SEQ ID NO: 72          moltype = AA  length = 12
FEATURE                Location/Qualifiers
REGION                 1..12
                       note = Synthetic - scFv22ChCDRL3
source                 1..12
                       mol_type = protein
                       organism = synthetic construct
SEQUENCE: 72
NSRDSSGNHH VV                                                     12

SEQ ID NO: 73          moltype = AA  length = 22
FEATURE                Location/Qualifiers
REGION                 1..22
                       note = Synthetic - Forward primer for amplifying scFv genes
source                 1..22
                       mol_type = protein
                       organism = synthetic construct
SEQUENCE: 73
TTTTTGGAGA TTTTCAACGT GA                                          22

SEQ ID NO: 74          moltype = AA  length = 27
FEATURE                Location/Qualifiers
REGION                 1..27
                       note = Synthetic - Reverse primer for amplifying scFv genes
source                 1..27
                       mol_type = protein
                       organism = synthetic construct
SEQUENCE: 74
GAATTTTCTG TATGAGGTTT TGCTAAA                                     27
```

HUMAN BLOOD-BRAIN BARRIER TARGETING ANTIBODIES

CROSS-REFERENCE TO RELATED APPLICATION

This application is a divisional application of U.S. application Ser. No. 17/759,854, filed Jul. 30, 2022, which application represents the U.S. National Stage of PCT/US2021/015466, filed Jan. 28, 2021, which application claims priority to U.S. Provisional Application No. 62/966,860 filed on Jan. 28, 2020, the contents of each of which are incorporated by reference in their entireties.

STATEMENT REGARDING FEDERALLY SPONSORED RESEARCH

This invention was made with government support under NS071513 awarded by the National Institutes of Health and HDTRA1-15-1-0012 awarded by the DOD/DTRA. The government has certain rights in the invention.

SEQUENCE LISTING

The contents of the electronic sequence listing (96029604735.xml; Size: 96,417 bytes; and Date of Creation: Oct. 24, 2025) is herein incorporated by reference in its entirety.

INTRODUCTION

The blood-brain barrier (BBB) prevents substantial accumulation of biologics in the central nervous system (CNS) after systemic administration, thereby limiting new treatments for neurological disorders. In the brain, the blood vessel network is made up of brain microvascular endothelial cells (BMECs) connected by tight junctions that restrict paracellular movement of molecules into the CNS, hence, controlling brain uptake of blood-borne substances (1). For instance, brain uptake of untargeted antibodies is limited to ~0.1% of circulating antibody levels (2), hampering therapeutic effects from a systemically administered biologic. However, a host of molecular transporters are expressed by BMECs that allow the selective passage of necessary nutrients across the BMECs by carrier-mediated and receptor-mediated transport (RMT) mechanisms. Thus, one approach to circumvent barrier properties consists of coopting BBB RMT systems by targeting them with antibodies that can first engage the RMT receptor on the blood side of BMECs and trigger transcytosis of the targeting antibody and any attached therapeutic cargo across the BMECs and into the brain (3). Two prominent examples are antibodies against the transferrin (TfR) (4) and insulin (IR) receptors (5). These systems, while mediating transport across the BBB, are somewhat inefficient and non-specific, and can result in deleterious off-target effects (6-8). While it is possible to mitigate these effects by antibody engineering strategies (9), there remains a significant need for the discovery of new BBB RMT-targeting antibody pairs that may address these challenges.

Several approaches have been implemented to identify new antibody-RMT pairs (10). Genomic and proteomic profiling of BBB endothelial cells has helped identify new BBB RMT targets such as basigin and CD98 heavy chain (11); however, it can be difficult to determine a priori what BBB proteins identified from omics data are actually capable of BBB transport. By contrast, phenotypic screening of large antibody libraries on a variety of BBB substrates can be used to identify cognate antibody-RMT pairs without prior knowledge of the RMT target (10). However, phenotypic screening of large libraries in vivo (12, 13) and in vitro (11, 14) for new antibody-RMT pairs has shown limited success, with only a handful of new BBB targeting antibodies isolated. In vivo screening challenges include the finding that phage antibody libraries are plagued by high background recoveries masking relevant clones (15), while antibodies identified from in vitro biopanning often do no not cross-react with in vivo antigens, due to potential alteration of protein expression profiles in culture. Further, human in vitro BBB models are inherently leaky, limiting the effectiveness of functional transcytosis screens of antibody libraries. Accordingly, there remains a need in the art for new antibody-RMT pairs that can effectively target the brain vasculature in vivo.

SUMMARY

The present invention provides isolated blood-brain barrier (BBB)-selective antibody or antigen-binding fragments thereof.

In some aspects, the disclosure provides an isolated blood-brain barrier (BBB)-selective antibody or antigen-binding fragment thereof comprising: (a) a heavy chain domain comprising a CDRH1 region comprising SEQ ID NO: 26 (GFTFSGYW), a CDHR2 region comprising SEQ ID NO:27 (IKGDGTDI), and a CDHR3 region comprising SEQ ID NO: 28 (ARDLRQTHWFDS), and a light chain domain comprising CDRL1 region comprising SEQ ID NO: 29 (SLRSYY), a CDRL2 region comprising the amino acid sequence GE, and a CDRL3 comprising SEQ ID NO: 30 (SSRDTSGNHVL); (b) a heavy chain domain comprising a CDRH1 region comprising SEQ ID NO:2 (GFTFSSYA), a CDHR2 region comprising SEQ ID NO: 3 (ISYDGSNK), and a CDHR3 region comprising SEQ ID NO: 4 (ARDSKGQSVRNRFDP), and a light chain domain comprising a CDRL1 region comprising SEQ ID NO: 5 (NLRSYY), a CDRL2 region comprising the amino acid sequence AN, and a CDRL3 comprising SEQ ID NO: 6 (NSRDSSGNLVV); (c) a heavy chain domain comprising a CDRH1 region comprising SEQ ID NO: 8 (GFTFSSYA), a CDHR2 region comprising SEQ ID NO: 9 (ISGSGGST), and a CDHR3 region comprising SEQ ID NO: 10 (ARGWKYFDY), and a light chain domain comprising a CDRL1 region comprising SEQ ID NO:11 (EGIYHW), a CDRL2 region comprising the amino acid sequence KA, and a CDRL3 comprising SEQ ID NO: 12 (QQYHTISRT); (d) a heavy chain domain comprising a CDRH1 region comprising SEQ ID NO: 14 (GFTFSSST), a CDHR2 region comprising SEQ ID NO: 15 (VSYDGNTQ), and a CDHR3 region comprising SEQ ID NO: 16 (AGLWGSLLGYFQH), and a light chain domain comprising a CDRL1 region comprising SEQ ID NO: 17 (QGVNNY), a CDRL2 region comprising the amino acid sequence AA, and a CDRL3 comprising SEQ ID NO: 18 (QQAHSFPPT); (e) a heavy chain domain comprising a CDRH1 region comprising SEQ ID NO:20 (GFTFSTYW), a CDHR2 region comprising SEQ ID NO: 21 (INQDGTAE), and a CDHR3 region comprising SEQ ID NO: 22 (ATPTGDSDY), and a light chain domain comprising a CDRL1 region comprising SEQ ID NO: 23 (SLRSYY), a CDRL2 region comprising the amino acid sequence GQ, and a CDRL3 comprising SEQ ID NO: 24 (HSRDSSGNHVL); (f) a heavy chain domain comprising a CDRH1 region comprising SEQ ID NO: 32 (GFTFSTYW), a CDHR2 region comprising SEQ ID NO: 33 (INQDG- TAE), and a CDHR3 region comprising SEQ ID NO:34 (ATPTGDSDY), and a light chain domain comprising a CDRL1 region comprising SEQ ID NO: 35 (QDIGNY), a CDRL2 region comprising the amino acid sequence DA, and a CDRL3 comprising SEQ ID NO: 36 (QKLSSYPLT); (g) a heavy chain domain comprising a CDRH1 region comprising SEQ ID NO: 38 (GFTFSNYA), a CDHR2 region comprising SEQ ID NO: 39 (ISGSGSST), and a CDHR3 region comprising SEQ ID NO: 40 (AKTSGWPYYFDY), and a light chain domain comprising a CDRL1 region comprising SEQ ID NO: 41 (SSNIGNNY), a CDRL2 region comprising the amino acid sequence DN, and a CDRL3 comprising SEQ ID NO: 42 (CSYAGSSTLV); (h) a heavy chain domain comprising a CDRH1 region comprising SEQ ID NO:44 (GFTFSSYA), a CDHR2 region comprising SEQ ID NO: 45 (VSGTGVST), and a CDHR3 region comprising SEQ ID NO: 46 (ARGLDWKSTPIDY), and a light chain domain comprising a CDRL1 region comprising SEQ ID NO: 47 (QSISGW), a CDRL2 region comprising the amino acid sequence GA, and a CDRL3 comprising SEQ ID NO: 48 (LQDYNGWT); (i) a heavy chain domain comprising a CDRH1 region comprising SEQ ID NO: 50 (GFTVSSNY), a CDHR2 region comprising SEQ ID NO: 51 (IKQDGSEK), and a CDHR3 region comprising SEQ ID NO: 52 (ARGGEEKNSGYYGDY), and a light chain domain comprising a CDRL1 region comprising SEQ ID NO: 53 (SLRSYY), a CDRL2 region comprising the amino acid sequence QD, and a CDRL3 comprising SEQ ID NO: 54 (QAWDSSTAHYV); (j) a heavy chain domain comprising a CDRH1 region comprising SEQ ID NO: 56 (GFTFSSYV), a CDHR2 region comprising SEQ ID NO:57 (ISGSGGST), and a CDHR3 region comprising SEQ ID NO: 58 (AKQNWYFDL), and a light chain domain comprising a CDRL1 region comprising SEQ ID NO: 59 (SLRSYY), a CDRL2 region comprising the amino acid sequence GE, and a CDRL3 comprising SEQ ID NO: 60 (NSRDSRGTHLEV); (k) a heavy chain domain comprising a CDRH1 region comprising SEQ ID NO:62 (GFTFSSYA), a CDHR2 region comprising SEQ ID NO: 63 (ISGSGGST), and a CDHR3 region comprising SEQ ID NO: 64 (AKSQGWAGDFDF), and a light chain domain comprising a CDRL1 region comprising SEQ ID NO: 65 (SSDIGTYNY), a CDRL2 region comprising the amino acid sequence EV, and a CDRL3 comprising SEQ ID NO: 66 (CSYAGSSTLV); or (l) a heavy chain domain comprising a CDRH1 region comprising SEQ ID NO: 68 (GFTFSSYA), a CDHR2 region comprising SEQ ID NO: 69 (ISSNGAIT), and a CDHR3 region comprising SEQ ID NO: 70 (VKDLKPSSWPPIYFDY), and a light chain domain comprising a CDRL1 region comprising SEQ ID NO: 71 (SLRTYY), a CDRL2 region comprising the amino acid sequence AN, and a CDRL3 comprising SEQ ID NO: 72 (NSRDSSGNHHVV).

In another aspect, the disclosure provides an isolated BBB-selective antibody or antigen-binding fragment thereof comprising an amino acid sequence selected from: (a) SEQ ID NO: 25 or a sequence having at least 90% identity to SEQ ID NO: 25; (b) SEQ ID NO: 1 or a sequence having at least 90% identity to SEQ ID NO: 1; (c) SEQ ID NO: 7 or a sequence having at least 90% identity to SEQ ID NO: 7; (d) SEQ ID NO: 13 or a sequence having at least 90% identity to SEQ ID NO: 13; (e) SEQ ID NO: 19 or a sequence having at least 90% identity to SEQ ID NO: 19; (f) SEQ ID NO: 31 or a sequence having at least 90% identity to SEQ ID NO: 31; (g) SEQ ID NO: 37 or a sequence having at least 90% identity to SEQ ID NO: 37; (h) SEQ ID NO: 43 or a sequence having at least 90% identity to SEQ ID NO: 43; (i) SEQ ID NO: 49 or a sequence having at least 90% identity to SEQ ID NO: 49; (j) SEQ ID NO: 55 or a sequence having at least 90% identity to SEQ ID NO: 55; (k) SEQ ID NO: 61 or a sequence having at least 90% identity to SEQ ID NO: 61; and (1) SEQ ID NO: 61 or a sequence having at least 90% identity to SEQ ID NO: 67.

In some aspects, the disclosure provides an isolated BBB-selective antibody or antigen-binding fragment comprising an amino acid sequence selected from: (a) SEQ ID NO: 25; (b) SEQ ID NO: 1; (c) SEQ ID NO: 7; (d) SEQ ID NO: 13; (e) SEQ ID NO: 19; (f) SEQ ID NO: 31; (g) SEQ ID NO: 37; (h) SEQ ID NO: 43; (i) SEQ ID NO: 49; (j) SEQ ID NO: 55; (k) SEQ ID NO: 61; and (1) SEQ ID NO: 66.

In yet another aspect, the disclosure provides a method of targeting an agent to the BBB of a subject comprising administering to the subject a BBB-selective antibody or antigen-binding fragment thereof as described herein, wherein the antibody is directly or indirectly linked to the agent, and wherein the BBB-selective antibody or antigen-binding fragment thereof is able to specifically target the BBB.

In yet another aspect, the disclosure provides a method of targeting a therapeutic agent to the BBB of a subject, the method comprising administering to the subject a BBB-selective antibody or antigen-binding fragment thereof described herein, wherein the antibody is directly or indirectly linked to the therapeutic agent, and wherein the BBB-selective antibody or antigen-binding fragment thereof is able to specifically target and translocate the BBB.

In yet another aspect, the disclosure provides a kit comprising the BBB-selective antibody or antigen-binding fragment described herein.

BRIEF DESCRIPTION OF THE DRAWINGS

FIG. 1. Antibody library screening on in vitro BBB model. (A) Scheme for the phage display screen. Step 1: pre-subtraction of phage scFv library on cultured human heart and lung endothelial cells in an effort to promote brain selectivity. Step 2: Supernatant from pre-subtraction step is next incubated with iPSC-derived BMECs to allow for binding and internalization of the antibody bearing phage. The antibody pools underwent three rounds of Step 2 internalization screening. Step 3: Internalizing phage were next dosed onto the blood side of BMECs in a Transwell format for 3 h to allow for transcytosis. Recovered scFv-bearing phage particles were subjected to further analysis. (B) Number of phage displaying an irrelevant anti-botulinum neurotoxin scFv that were recovered in the basolateral, brain side chamber in the Transwell system as a function of trans-endothelial electrical resistance (TEER). (C) Enrichment of BMEC-binding phage displayed scFvs as observed by FACS-analysis of phage antibody pools during screening Step 2. Shown are representative histograms of BMECs labeled with phage-displayed scFvs after respective screening rounds. The number of cells (counts: Y-axis) is given as function of the fluorescence intensity of phage antibody labeling of the cells (X-axis). In all experiments, BMECs were incubated with phage antibody pools, and cell-binding was detected by anti-M13 antibody. Geometric means are round R1-80.6, R2-27, R3-10.9, Non-binding phage-3.16, respectively. (D) Representative images from clonal phage immunocytochemistry with BMECs to determine clones displaying a BMEC binding phenotype. Scale bar, 50 μm. For panels C) and D), Non-binding phage displays antibotulinum neurotoxin scFv.

FIG. 6. ScFvs bind and internalize into iPSC-derived BMECs. ScFvs (13.2 μg/ml) were pre-dimerized with mouse anti-c-myc antibody in 4:1 molar ratio. BMECs were incubated with scFv-dimers at 4° C. and subsequently at 37° C. for 30 min. The cell membrane was washed with cold buffer and the membrane bound fraction labeled with anti-mouse AlexaFluor555 antibody (red) on ice. After fixation and permeabilization, the internalized scFvs were labeled with anti-mouse AlexaFluor488 antibody (green), nuclei (blue). Images were taken on epifluorescence microscope. Negative control is an anti-botulinum neurotoxin scFv (Ctrl-scFv). Scale bar, 20 μm.

FIG. 7. Competitive BMEC binding assay. Binding signal of each scFv-Fc or control anti-TfR or anti-IR antibodies following competition with soluble receptor ectodomains was normalized to binding in the absence of competition. Data are presented as the means±S.D. calculated from 3 independent experiments. * p<0.05 versus uncompeted control using students t test.

FIG. 10. Body temperature of mice in response to antibody-neurotensin conjugates. The body temperature of mice was measured before and after administration of antibody-neurotensin conjugates via the retro-orbital sinus. Time 0 equals the time of injection (n=4). The decrease in body temperature of mice receiving scFv-46.1-rabbitFc-neurotensin-antibody conjugate indicates engagement of neurotensin receptor 1 on expressing neurons and hence its targeted transport across the blood-brain barrier.

DETAILED DESCRIPTION

Figure 2:
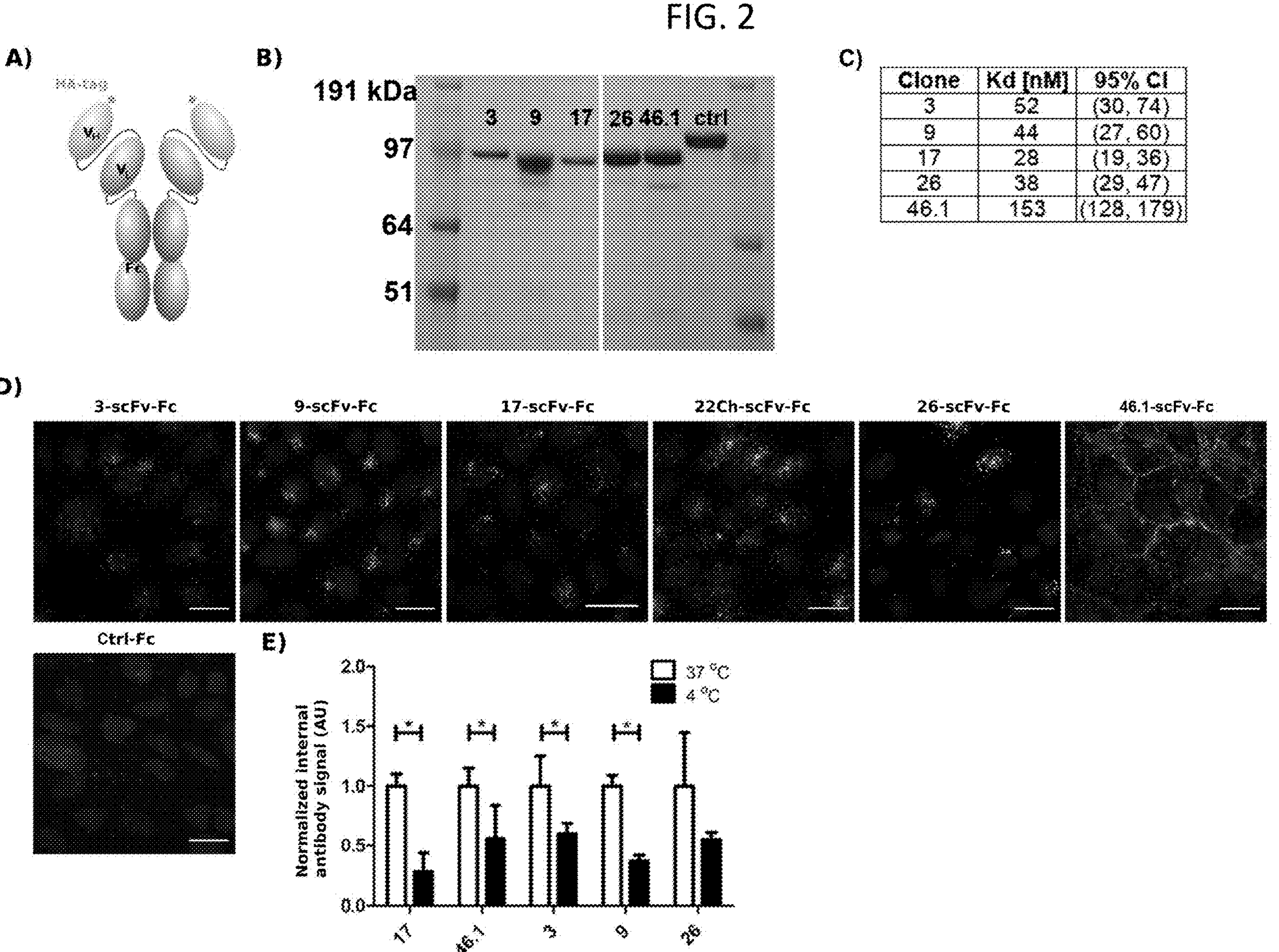
FIG. 2. Antibodies binding properties. (A) ScFv-Fc construct with scFv linked directly to rabbit IgG Fc region. (B) Non-reducing, Coomassie blue-stained SDS-PAGE gel analysis of scFv-Fc antibodies following expression in HEK293F cells and protein A/G purification. Molecular weights are indicated. (C) Apparent equilibrium binding affinity of selected clones. The table shows numeric values for the best-fit equilibrium binding affinity (Kd) and associated 95% CI. (D) Binding and internalization of antibodies into BMECs. Live cells were incubated with antibodies (5 μg/ml) at 4° C. and subsequently at 37° C. for 30 min. The cell membrane was washed with cold buffer and the membrane bound fraction labeled with anti-rabbit Fc AlexaFluor555 antibody (red). After fixation and permeabilization the internalized antibodies were labeled with anti-rabbit Fc AlexaFluor488 antibody (green). Images were taken on an epifluorescent microscope. Scale bar, 20 μm. (E) Temperature-dependent internalization of antibodies. Internalized antibody fluorescent signal values at 4° C. are normalized to the total signal per cell at 37° C. Reported are means±S.D., n=3, *p<0.05 by the Student's T-test. (F) ScFv-Fcs binding to human and mouse brain microvessels. Cryosections of human and mouse brain were immunolabeled for CD31 (green) to visualize the blood vessels and incubated with 5 μg/ml scFv-Fcs (red) to identify scFv-Fc binding. Nuclei are visualized in blue. Images were taken on a confocal microscope. Scale bar, 20 μm.
Figure 2:
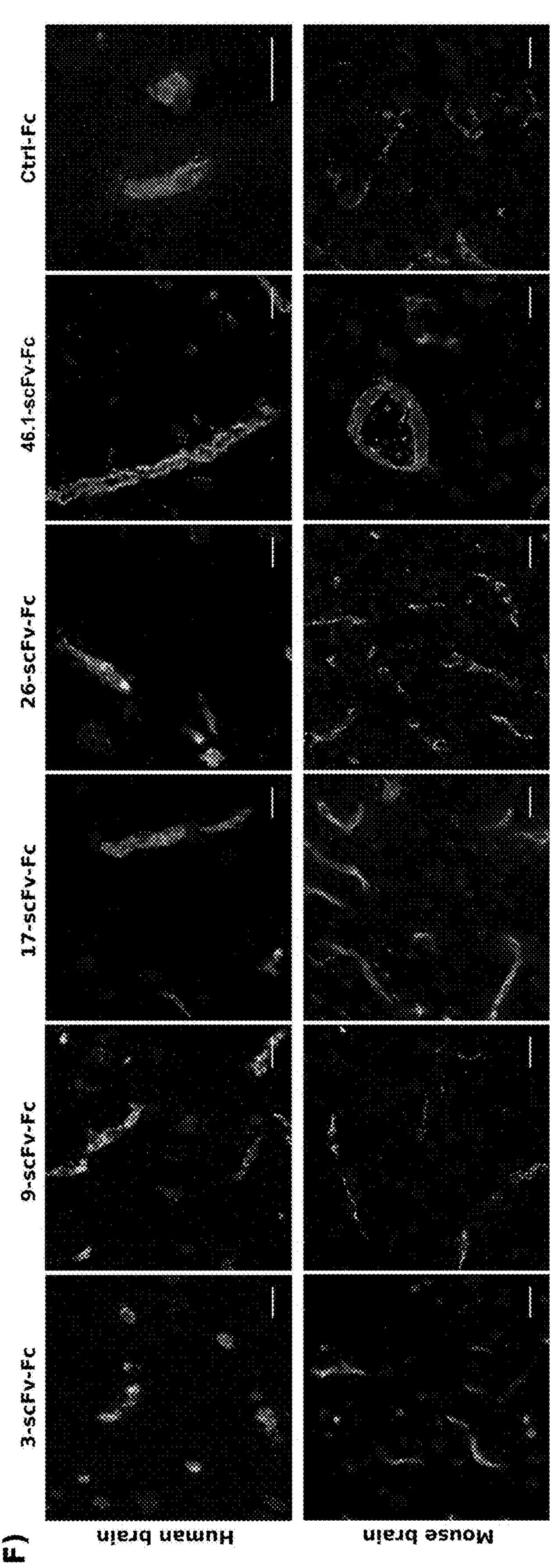

Before the present invention is described, it is to be understood that this invention is not limited to the particular methodology, protocols, and reagents described, as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing chemicals, cell lines, vectors, animals, instruments, statistical analysis, and methodologies, which might be used in connection with the invention. Nothing herein is to be construed as an admission that the invention is not entitled to antedate such disclosure by virtue of prior invention.

Compositions:

The present invention provides isolated blood-brain barrier (BBB)-selective antibodies or antigen-binding fragments thereof. In some embodiments, the BBB-selective antibody or antigen-binding fragment thereof specifically binds to the brain (e.g., blood brain barrier endothelium). The terms "specifically" or "selectively" are used interchangeably herein to describe an antibody that is capable of binding to the surface of the endothelium in brain vessels that line the blood brain barrier. By "binding" we mean that the antibodies can be detected at a given tissue's endothelium using standard methods (e.g., tissue section immunofluorescence assays). Further, in some embodiments, the BBB-selective antibody or antigen-binding fragment thereof bind the BBB and translocate across the BBB. As described below, translocation across the BBB can be detected in vivo (e.g., mouse model) or in vitro using a transwell tissue culture BBB-model.

In the Examples disclosed herein, the inventors describe a new screening method that relies on human induced pluripotent stem cell (iPSC)-derived brain microvascular endothelial cells (BMECs) as a screening substrate. The iPSC-derived BMECs have well-developed tight junctions, express key BBB markers and, most importantly, are a reasonable facsimile of both primary human BMECs and acutely isolated human BMECs in terms of their transporter expression profiles (16-19). Using the iPSC-derived BMECs to perform a transcytosis screen with a phage display scFv library, the inventors identified a cohort of antibodies that are able to react with human BBB antigens and target the murine brain vasculature in vivo. Lead candidates exhibited binding and internalization into BMECs as well as binding to both human and mouse BBB in brain tissue sections. Antibodies targeted the murine BBB after intravenous administration with one particular clone, 46.1-scFv, exhibiting a 26-fold increase in brain accumulation (8.1 nM). Moreover, clone 46.1-scFv was found to associate with postvascular cells, suggesting its potential utility for CNS therapeutic delivery. Thus, the present disclosure provides a number of BBB-specific antibodies and antigen-binding fragments thereof specific to the BBB.

The terms "antibody" or "antibody molecule" are used interchangeably herein to refer to immunoglobulin molecules or other molecules that comprise an antigen-binding domain from an immunoglobulin molecule. Suitable antibody molecules include, without limitation, whole antibodies (e.g., IgG, IgA, IgE, IgM, or IgD), monoclonal antibodies, polyclonal antibodies, chimeric antibodies, humanized antibodies, and antibody fragments, including single chain variable fragments (ScFv), single domain antibodies, antigen-binding fragments (e.g., complementarity determining region (CDR) domains), and genetically engineered antibodies. Thus, any form of antibody, antibody fragment, or antibody-derived fragment may be used with the present invention, as long as it retains the ability to bind the BBB in vivo.

As stated above, the term "antibody" includes "antibody fragments" or "antibody-derived fragments" that comprise an antigen-binding domain. As used herein, the term "antibody fragment" is intended to include any fragment that displays antigen binding function, for example, Fab, Fab', F(ab')2, scFv, Fv, dsFv, ds-scFv, Fd, dAbs, TandAbs dimers, mini bodies, monobodies, diabodies, and multimers thereof and bispecific antibody fragments. The CDR and ScFv sequences described herein can be genetically engineered into antibodies and antibody fragments using conventional techniques, including recombinant or chemical synthesis techniques, which are well known and described in the art. As used herein, the term "fragment" refers to fragments of biological relevance (i.e., functional fragments). For example, the fragments may contribute to or enable antigen binding, form part of or all of the antigen-binding site, or contribute to the prevention of the antigen interacting with its natural ligands. In some embodiments, fragments comprise a heavy chain variable region ($V_H$ domain) and light chain variable region ($V_L$) disclosed herein. In some embodiments, the fragments comprise one or more of the heavy chain complementarity determining regions (CDRHs) of the antibodies or of the $V_H$ domains, and one or more of the light chain complementarity determining regions (CDRLs), or $V_L$ domains to form the antigen-binding site. A fragment is suitable for use in the present methods and kits if it retains its ability to bind in vivo to the BBB.

The antibodies disclosed in the present invention may be modified to be human antibodies which include the constant region from a human germline immunoglobulin sequences. The term "recombinant human antibody" or "chimeric human antibody" includes all human antibodies that are prepared, expressed, created or isolated by recombinant means, such as antibodies isolated from a host cell such as an SP2-0, NS0 or CHO cell (like CHO K1) or from an animal (e.g., a mouse) that is transgenic for human immunoglobulin genes or antibodies or polypeptides expressed using a recombinant expression vector transfected into a host cell. Such recombinant human antibodies have variable and in some embodiments, constant regions derived from human germline immunoglobulin sequences in a rearranged form.

The antibodies and antigen-binding fragments of the present invention may be from any appropriate source. The antibodies can be produced in vitro or in vivo, and can be wholly or partially synthetically produced. For example, the antibodies may be from a recombinant source and/or produced in transgenic animals or transgenic plants. Preferably, an antibody or antibody fragment comprises an at least the heavy chain variable region ($V_H$) of an antibody, which generally comprises the antigen-binding site. In certain preferred embodiments, the antibody comprises the heavy chain variable region and light chain variable region ($V_L$). The antibody can be made such that it comprises all or a portion of a heavy chain constant region, such as an IgG1, IgG2, IgG3, IgG4, IgAQ1, IgA2, IgE, IgM or IgD constant region. Furthermore, the antibody or antibody fragment can comprise all or a portion of a kappa light chain constant region or a lambda light chain constant region. All or part of such constant regions may be produced wholly or partially synthetically. Appropriate sequences for such constant regions are well known and documented in the art.

In one embodiment, the present invention provides an isolated BBB-selective antibody or antigen-binding fragment thereof comprising or consists of a heavy chain domain, wherein the heavy chain domain is selected from the group consisting of: (a) a heavy chain domain comprising one or more of (i) a CDRH1 region comprising SEQ ID NO: 26 (GFTFSGYW), (ii) a CDHR2 region comprising SEQ ID NO: 27 (IKGDGTDI), and (iii) a CDHR3 region comprising SEQ ID NO:28 (ARDLRQTHWFDS); (b) a heavy chain domain comprising one or more of (i) a CDRH1 region comprising SEQ ID NO: 2 (GFTFSSYA), (ii) a CDHR2 region comprising SEQ ID NO: 3 (ISYDGSNK), and (iii) a CDHR3 region comprising SEQ ID NO: 4 (ARDSKGQSVRNRFDP), (c) a heavy chain domain comprising one or more of (i) a CDRH1 region comprising SEQ ID NO:8 (GFTFSSYA), (ii) a CDHR2 region comprising SEQ ID NO: 9 (ISGSGGST), and (iii) a CDHR3 region comprising SEQ ID NO: 10 (ARGWKYFDY), (d) a heavy chain domain comprising one or more of (i) a CDRH1 region comprising SEQ ID NO: 14 (GFTFSSST), (ii) a CDHR2 region comprising SEQ ID NO: 15 (VSYDGNTQ), and (iii) a CDHR3 region comprising SEQ ID NO: 16 (AGLWGSLLGYFQH), (e) a heavy chain domain comprising one or more of (i) a CDRH1 region comprising SEQ ID NO: 20 (GFTFSTYW), (ii) a CDHR2 region comprising SEQ ID NO: 21 (INQDGTAE), and (iii) a CDHR3 region comprising SEQ ID NO: 22 (ATPTGDSDY), (f) a heavy chain domain comprising one or more of: (i) a CDRH1 region comprising SEQ ID NO: 32 (GFTFSTYW), (ii) a CDHR2 region comprising SEQ ID NO: 33 (INQDGTAE), and (iii) a CDHR3 region comprising SEQ ID NO: 34 (ATPTGDSDY), (g) a heavy chain domain comprising one or more of (i) a CDRH1 region comprising SEQ ID NO: 38 (GFTFSNYA), (ii) a CDHR2 region comprising SEQ ID NO: 39 (ISGSGSST), and (iii) a CDHR3 region comprising SEQ ID NO: 40 (AKTSGWPYYFDY), (h) a heavy chain domain comprising one or more of: (i) a CDRH1 region comprising SEQ ID NO: 44 (GFTFSSYA), (ii) a CDHR2 region comprising SEQ ID NO: 45 (VSGTGVST), and (iii) a CDHR3 region comprising SEQ ID NO:46 (ARGLDWKSTPIDY), (i) a heavy chain domain comprising one or more of: (i) a CDRH1 region comprising SEQ ID NO: 50 (GFTVSSNY), (ii) a CDHR2 region comprising SEQ ID NO: 51 (IKQDGSEK), and (iii) a CDHR3 region comprising SEQ ID NO: 52 (ARGGEEKNSGYYGDY), (j) a heavy chain domain comprising one or more of: (i) a CDRH1 region comprising SEQ ID NO:56 (GFTFSSYV), (ii) a CDHR2 region comprising SEQ ID NO: 57 (ISGSGGST), and (iii) a CDHR3 region comprising SEQ ID NO: 58 (AKQNWYFDL), (k) a heavy chain domain comprising one or more of (i) a CDRH1 region comprising SEQ ID NO: 62 (GFTFSSYA), (ii) a CDHR2 region comprising SEQ ID NO: 63 (ISGSGGST), and (iii) a CDHR3 region comprising SEQ ID NO: 64 (AKSQGWAGDFDF), or (1) a heavy chain domain comprising one or more of (i) a CDRH1 region comprising SEQ ID NO: 68 (GFTFSSYA), (ii) a CDHR2 region comprising SEQ ID NO: 69 (ISSNGAIT), and (iii) a CDHR3 region comprising SEQ ID NO: 70 (VKDLKPSSWPPIYFDY). In some embodiments, the isolated BBB-selective antibody or antigen-binding fragment thereof further comprises a variable light domain.

In some embodiments, the isolated BBB-selective antibody or antigen-binding fragment thereof comprises or consists of: (a) a heavy chain domain comprising one or more of (i) a CDRH1 region comprising SEQ ID NO: 26 (GFTFSGYW), (ii) a CDHR2 region comprising SEQ ID NO:27 (IKGDGTDI), and (iii) a CDHR3 region comprising SEQ ID NO: 28 (ARDLRQTHWFDS), and a light chain domain comprising one or more of: (i) CDRL1 region comprising SEQ ID NO: 29 (SLRSYY), (ii) a CDRL2 region comprising the amino acid sequence GE, and (iii) a CDRL3 comprising SEQ ID NO: 30 (SSRDTSGNHVL); (b) a heavy chain domain comprising one or more of (i) a CDRH1 region comprising SEQ ID NO: 2 (GFTFSSYA), (ii) a CDHR2 region comprising SEQ ID NO: 3 (ISYDGSNK), and (iii) a CDHR3 region comprising SEQ ID NO: 4 (ARDSKGQSVRNRFDP), and a light chain domain comprising one or more of (i) a CDRL1 region comprising SEQ ID NO: 5 (NLRSYY), (ii) a CDRL2 region comprising the amino acid sequence AN, and (iii) a CDRL3 comprising SEQ ID NO: 6 (NSRDSSGNLVV); (c) a heavy chain domain comprising one or more of (i) a CDRH1 region comprising SEQ ID NO: 8 (GFTFSSYA), (ii) a CDHR2 region comprising SEQ ID NO: 9 (ISGSGGST), and (iii) a CDHR3 region comprising SEQ ID NO: 10 (ARGWKYFDY), and a light chain domain comprising one or more of: (i) a CDRL1 region comprising SEQ ID NO: 11 (EGIYHW), (ii) a CDRL2 region comprising the amino acid sequence KA, and (iii) a CDRL3 comprising SEQ ID NO: 12 (QQYHTISRT); (d) a heavy chain domain comprising one or more of: (i) a CDRH1 region comprising SEQ ID NO: 14 (GFTFSSST), (ii) a CDHR2 region comprising SEQ ID NO: 15 (VSYDGNTQ), and (iii) a CDHR3 region comprising SEQ ID NO: 16 (AGLWGSLLGYFQH), and a light chain domain comprising one or more of (i) a CDRL1 region comprising SEQ ID NO:17 (QGVNNY), (ii) a CDRL2 region comprising the amino acid sequence AA, and (iii) a CDRL3 comprising SEQ ID NO: 18 (QQAHSFPPT); (e) a heavy chain domain comprising one or more of: (i) a CDRH1 region comprising SEQ ID NO: 20 (GFTFSTYW), (ii) a CDHR2 region comprising SEQ ID NO: 21 (INQDGTAE), and (iii) a CDHR3 region comprising SEQ ID NO: 22 (ATPTGDSDY), and a light chain domain comprising one or more of: (i) a CDRL1 region comprising SEQ ID NO: 23 (SLRSYY), (ii) a CDRL2 region comprising the amino acid sequence GQ, and (iii) a CDRL3 comprising SEQ ID NO: 24 (HSRDSSGNHVL); (f) a heavy chain domain comprising one or more of: (i) a CDRH1 region comprising SEQ ID NO: 32 (GFTFSTYW), (ii) a CDHR2 region comprising SEQ ID NO: 33 (INQDGTAE), and (iii) a CDHR3 region comprising SEQ ID NO: 34 (ATPTGDSDY), and a light chain domain comprising one or more of: (i) a CDRL1 region comprising SEQ ID NO: 35 (QDIGNY), (ii) a CDRL2 region comprising the amino acid sequence DA, and (iii) a CDRL3 comprising SEQ ID NO: 36 (QKLSSYPLT); (g) a heavy chain domain comprising one or more of: (i) a CDRH1 region comprising SEQ ID NO: 38 (GFTFSNYA), (ii) a CDHR2 region comprising SEQ ID NO: 39 (ISGSGSST), and (iii) a CDHR3 region comprising SEQ ID NO: 40 (AKTSGWPYYFDY), and a light chain domain comprising one or more of: (i) a CDRL1 region comprising SEQ ID NO: 41 (SSNIGNNY), (ii) a CDRL2 region comprising the amino acid sequence DN, and (iii) a CDRL3 comprising SEQ ID NO: 42 (CSYAGSSTLV); (h) a heavy chain domain comprising one or more of (i) a CDRH1 region comprising SEQ ID NO: 44 (GFTFSSYA), (ii) a CDR2 region comprising SEQ ID NO: 45 (VSGTGVST), and (iii) a CDHR3 region comprising SEQ ID NO: 46 (ARGLDWKSTPIDY), and a light chain domain comprising one or more of: (i) a CDRL1 region comprising SEQ ID NO: 47 (QSISGW), (ii) a CDRL2 region comprising the amino acid sequence GA, and (iii) a CDRL3 comprising SEQ ID NO: 48 (LQDYNGWT); (i) a heavy chain domain comprising one or more of (i) a CDRH1 region comprising SEQ ID NO: 50 (GFTVSSNY), (ii) a CDHR2 region comprising SEQ ID NO: 51 (IKQDGSEK), and (iii) a CDHR3 region comprising SEQ ID NO: 52 (ARGGEEKNSGYYGDY), and a light chain domain comprising one or more of: (i) a CDRL1 region comprising SEQ ID NO: 53 (SLRSYY), (ii) a CDRL2 region comprising the amino acid sequence QD, and (iii) a CDRL3 comprising SEQ ID NO: 54 (QAWDSSTAHYV); (j) a heavy chain domain comprising one or more of: (i) a CDRH1 region comprising SEQ ID NO: 56 (GFTFSSYV), (ii) a CDHR2 region comprising SEQ ID NO: 57 (ISGSGGST), and (iii) a CDHR3 region comprising SEQ ID NO: 58 (AKQNWYFDL), and a light chain domain comprising one or more of: (i) a CDRL1 region comprising SEQ ID NO: 59 (SLRSYY), (ii) a CDRL2 region comprising the amino acid sequence GE, and (iii) a CDRL3 comprising SEQ ID NO: 60 (NSRDSRGTH-LEV); (k) a heavy chain domain comprising (i) a CDRH1 region comprising SEQ ID NO: 62 (GFTFSSYA), (ii) a CDHR2 region comprising SEQ ID NO: 63 (ISGSGGST), and (iii) a CDHR3 region comprising SEQ ID NO: 64 (AKSQGWAGDFDF), and a light chain domain comprising one or more of: (i) a CDRL1 region comprising SEQ ID NO: 65 (SSDIGTYNY), (ii) a CDRL2 region comprising the amino acid sequence EV, and (iii) a CDRL3 comprising SEQ ID NO:66 (CSYAGSSTLV); or (l) a heavy chain domain comprising one or more of: (i) a CDRH1 region comprising SEQ ID NO: 68 (GFTFSSYA), (ii) a CDHR2 region comprising SEQ ID NO: 69 (ISSNGAIT), and (iii) a CDHR3 region comprising SEQ ID NO: 70 (VKDLKPSS-WPPIYFDY), and a light chain domain comprising one or more of: (i) a CDRL1 region comprising SEQ ID NO:71 (SLRTYY), (ii) a CDRL2 region comprising the amino acid sequence AN, and (iii) a CDRL3 comprising SEQ ID NO: 72 (NSRDSSGNHHVV).

In some embodiments, the isolated BBB-selective antibody or antigen-binding fragment thereof comprises or consists of: (a) a heavy chain domain comprising (i) a CDRH1 region comprising SEQ ID NO: 26 (GFTFSGYW), (ii) a CDHR2 region comprising SEQ ID NO: 27 (IKGDGTDI), and (iii) a CDHR3 region comprising SEQ ID NO: 28 (ARDLRQTHWFDS), and a light chain domain comprising (i) a CDRL1 region comprising SEQ ID NO: 29 (SLRSYY), (ii) a CDRL2 region comprising the amino acid sequence GE, and (iii) a CDRL3 comprising SEQ ID NO:30 (SSRDTSGNHVL); (b) a heavy chain domain comprising (i) a CDRH1 region comprising SEQ ID NO: 2 (GFTFSSYA), (ii) a CDHR2 region comprising SEQ ID NO: 3 (ISYDGSNK), and (iii) a CDHR3 region comprising SEQ ID NO: 4 (ARDSKGQSVRNRFDP), and a light chain domain comprising (i) a CDRL1 region comprising SEQ ID NO: 5 (NLRSYY), (ii) a CDRL2 region comprising the amino acid sequence AN, and (iii) a CDRL3 comprising SEQ ID NO: 6 (NSRDSSGNLVV); (c) a heavy chain domain comprising (i) a CDRH1 region comprising SEQ ID NO: 8 (GFTFSSYA), (ii) a CDHR2 region comprising SEQ ID NO: 9 (ISGSGGST), and (iii) a CDHR3 region comprising SEQ ID NO: 10 (ARGWKYFDY), and a light chain domain comprising (i) a CDRL1 region comprising SEQ ID NO: 11 (EGIYHW), (ii) a CDRL2 region comprising the amino acid sequence KA, and (iii) a CDRL3 comprising SEQ ID NO: 12 (QQYHTISRT); (d) a heavy chain domain comprising (i) a CDRH1 region comprising SEQ ID NO:14 (GFTFSSST), (ii) a CDHR2 region comprising SEQ ID NO: 15 (VSYDGNTQ), and (iii) a CDHR3 region comprising SEQ ID NO: 16 (AGLWGSLLGYFQH), and a light chain domain comprising (i) a CDRL1 region comprising SEQ ID NO: 17 (QGVNNY), (ii) a CDRL2 region comprising the amino acid sequence AA, and (iii) a CDRL3 comprising SEQ ID NO: 18 (QQAHSFPPT); (e) a heavy chain domain comprising (i) a CDRH1 region comprising SEQ ID NO:20 (GFTFSTYW), (ii) a CDHR2 region comprising SEQ ID NO: 21 (INQDGTAE), and (iii) a CDHR3 region comprising SEQ ID NO: 22 (ATPTGDSDY), and a light chain domain comprising (i) a CDRL1 region comprising SEQ ID NO: 23 (SLRSYY), (ii) a CDRL2 region comprising the amino acid sequence GQ, and (iii) a CDRL3 comprising SEQ ID NO: 24 (HSRDSSGNHVL); (f) a heavy chain domain comprising (i) a CDRH1 region comprising SEQ ID NO: 32 (GFTFSTYW), (ii) a CDHR2 region comprising SEQ ID NO: 33 (INQDGTAE), and (iii) a CDHR3 region comprising SEQ ID NO: 34 (ATPTGDSDY), and a light chain domain comprising (i) a CDRL1 region comprising SEQ ID NO: 35 (QDIGNY), (ii) a CDRL2 region comprising the amino acid sequence DA, and (iii) a CDRL3 comprising SEQ ID NO: 36 (QKLSSYPLT); (g) a heavy chain domain comprising (i) a CDRH1 region comprising SEQ ID NO:38 (GFTFSNYA), (ii) a CDHR2 region comprising SEQ ID NO: 39 (ISGSGSST), and (iii) a CDHR3 region comprising SEQ ID NO: 40 (AKTSGWPYYFDY), and a light chain domain comprising (i) a CDRL1 region comprising SEQ ID NO: 41 (SSNIGNNY), (ii) a CDRL2 region comprising the amino acid sequence DN, and (iii) a CDRL3 comprising SEQ ID NO: 42 (CSYAGSSTLV); (h) a heavy chain domain comprising (i) a CDRH1 region comprising SEQ ID NO:44 (GFTFSSYA), (ii) a CDHR2 region comprising SEQ ID NO: 45 (VSGTGVST), and (iii) a CDHR3 region comprising SEQ ID NO: 46 (ARGLDWKSTPIDY), and a light chain domain comprising (i) a CDRL1 region comprising SEQ ID NO: 47 (QSISGW), (ii) a CDRL2 region comprising the amino acid sequence GA, and (iii) a CDRL3 comprising SEQ ID NO: 48 (LQDYNGWT); (i) a heavy chain domain comprising (i) a CDRH1 region comprising SEQ ID NO:50 (GFTVSSNY), (ii) a CDHR2 region comprising SEQ ID NO: 51 (IKQDGSEK), and (iii) a CDHR3 region comprising SEQ ID NO: 52 (ARG-GEEKNSGYYGDY), and a light chain domain comprising (i) a CDRL1 region comprising SEQ ID NO: 53 (SLRSYY), (ii) a CDRL2 region comprising the amino acid sequence QD, and (iii) a CDRL3 comprising SEQ ID NO: 54 (QAWDSSTAHYV); (j) a heavy chain domain comprising (i) a CDRH1 region comprising SEQ ID NO: 56 (GFTFSSYV), (ii) a CDHR2 region comprising SEQ ID NO: 57 (ISGSGGST), and (iii) a CDHR3 region comprising SEQ ID NO: 58 (AKQNWYFDL), and a light chain domain comprising (i) a CDRL1 region comprising SEQ ID NO: 59 (SLRSYY), (ii) a CDRL2 region comprising the amino acid sequence GE, and (iii) a CDRL3 comprising SEQ ID NO: 60 (NSRDSRGTHLEV); (k) a heavy chain domain comprising (i) a CDRH1 region comprising SEQ ID NO: 62 (GFTFSSYA), (ii) a CDHR2 region comprising SEQ ID NO: 63 (ISGSGGST), and (iii) a CDHR3 region comprising SEQ ID NO: 64 (AKSQGWAGDFDF), and a light chain domain comprising (i) a CDRL1 region comprising SEQ ID NO: 65 (SSDIGTYNY), (ii) a CDRL2 region comprising the amino acid sequence EV, and (iii) a CDRL3 comprising SEQ ID NO: 66 (CSYAGSSTLV); or (l) a heavy chain domain comprising (i) a CDRH1 region comprising SEQ ID NO: 68 (GFTFSSYA), (ii) a CDHR2 region comprising SEQ ID NO: 69 (ISSNGAIT), and (iii) a CDHR3 region comprising SEQ ID NO: 70 (VKDLKPSSWPPIYFDY), and a light chain domain comprising (i) a CDRL1 region comprising SEQ ID NO: 71 (SLRTYY), (ii) a CDRL2 region comprising the amino acid sequence AN, and (iii) a CDRL3 comprising SEQ ID NO: 72 (NSRDSSGNHHVV).

In some embodiments, the isolated BBB-selective antibody or antigen-binding fragment thereof comprises an amino acid sequence selected from: (a) SEQ ID NO: 25 or a sequence having at least 90% identity to SEQ ID NO: 25; (b) SEQ ID NO: 1 or a sequence having at least 90% identity to SEQ ID NO: 1; (c) SEQ ID NO: 7 or a sequence having at least 90% identity to SEQ ID NO:7; (d) SEQ ID NO: 13 or a sequence having at least 90% identity to SEQ ID NO: 13; (e) SEQ ID NO: 19 or a sequence having at least 90% identity to SEQ ID NO: 19; (f) SEQ ID NO: 31 or a sequence having at least 90% identity to SEQ ID NO: 31; (g) SEQ ID NO: 37 or a sequence having at least 90% identity to SEQ ID NO: 37; (h) SEQ ID NO: 43 or a sequence having at least 90% identity to SEQ ID NO: 43; (i) SEQ ID NO: 49 or a sequence having at least 90% identity to SEQ ID NO: 49; (j) SEQ ID NO: 55 or a sequence having at least 90% identity to SEQ ID NO: 55; (k) SEQ ID NO: 61 or a sequence having at least 90% identity to SEQ ID NO: 61; and (1) SEQ ID NO:61 or a sequence having at least 90% identity to SEQ ID NO: 67. Suitable isolated blood-brain barrier (BBB)-selective antibody or antigen-binding fragment thereof comprise or consists of scFv46.1, scFv3, scFv9, scFv17, scFv26, scFv6i, scFv5A, scFv2, scFv4B, scFv5E-0.4, scFvB3-R3, or scFv22Ch.

In some embodiments, the antibodies have substantial identity to the polypeptide found in SEQ ID NO: 25. In some embodiments, the antibodies have at least 50% identity to SEQ ID NO: 25, alternatively at least 75% sequence identity, alternatively at least 80% sequence identity, alternatively at least 90% sequence identity, alternatively at least 95% sequence identity, alternatively at least 98% sequence identity, alternatively at least 100% sequence identity. In some embodiments, the modified protein has at least 100% sequence identity within CDRH1, CDRH2 and CDRH3 within SEQ ID NO: 25 (e.g., SEQ ID Nos. 30-32). In some embodiments, the antibodies further have 100% sequence identity with CDRL1, CDRL2 and CDRL3 within SEQ ID NO: 25 (e.g., SEQ ID NO: 29, the amino acid sequence GE, and SEQ ID NO: 30).

In some embodiments, the antibodies have substantial identity to the polypeptide found in SEQ ID NO: 1. In some embodiments, the antibodies have at least 50% identity to SEQ ID NO: 1, alternatively at least 75% sequence identity, alternatively at least 80% sequence identity, alternatively at least 90% sequence identity, alternatively at least 95% sequence identity, alternatively at least 98% sequence identity, alternatively at least 100% sequence identity. In some embodiments, the modified protein has at least 100% sequence identity within CDRH1, CDRH2 and CDRH3 within SEQ ID NO: 1 (e.g., SEQ ID Nos. 2-4). In some embodiments, the antibodies further have 100% sequence identity with CDRL1, CDRL2 and CDRL3 within SEQ ID NO: 1 (e.g., SEQ ID NO: 5, the amino acid sequence AN, and SEQ ID NO: 6).

In some embodiments, the antibodies have substantial identity to the polypeptide found in SEQ ID NO: 7. In some embodiments, the antibodies have at least 50% identity to SEQ ID NO: 7, alternatively at least 75% sequence identity, alternatively at least 80% sequence identity, alternatively at least 90% sequence identity, alternatively at least 95% sequence identity, alternatively at least 98% sequence identity, alternatively at least 100% sequence identity. In some embodiments, the modified protein has at least 100% sequence identity within CDRH1, CDRH2 and CDRH3 within SEQ ID NO: 7 (e.g., SEQ ID Nos. 9-11). In some embodiments, the antibodies further have 100% sequence identity with CDRL1, CDRL2 and CDRL3 within SEQ ID NO: 7 (e.g., SEQ ID NO: 11, the amino acid sequence KA, and SEQ ID NO: 12).

In some embodiments, the antibodies have substantial identity to the polypeptide found in SEQ ID NO: 13. In some embodiments, the antibodies have at least 50% identity to SEQ ID NO: 13, alternatively at least 75% sequence identity, alternatively at least 80% sequence identity, alternatively at least 90% sequence identity, alternatively at least 95% sequence identity, alternatively at least 98% sequence identity, alternatively at least 100% sequence identity. In some embodiments, the modified protein has at least 100% sequence identity within CDRH1, CDRH2 and CDRH3 within SEQ ID NO: 13 (e.g., SEQ ID Nos. 16-18). In some embodiments, the antibodies further have 100% sequence identity with CDRL1, CDRL2 and CDRL3 within SEQ ID NO: 13 (e.g., SEQ ID NO: 17, the amino acid sequence AA, and SEQ ID NO: 18).

In some embodiments, the antibodies have substantial identity to the polypeptide found in SEQ ID NO: 19. In some embodiments, the antibodies have at least 50% identity to SEQ ID NO: 19, alternatively at least 75% sequence identity, alternatively at least 80% sequence identity, alternatively at least 90% sequence identity, alternatively at least 95% sequence identity, alternatively at least 98% sequence identity, alternatively at least 100% sequence identity. In some embodiments, the modified protein has at least 100% sequence identity within CDRH1, CDRH2 and CDRH3 within SEQ ID NO: 19 (e.g., SEQ ID Nos. 22-25). In some embodiments, the antibodies further have 100% sequence identity with CDRL1, CDRL2 and CDRL3 within SEQ ID NO: 19 (e.g., SEQ ID NO: 23, the amino acid sequence GQ, and SEQ ID NO: 24).

In some embodiments, the antibodies have substantial identity to the polypeptide found in SEQ ID NO: 31. In some embodiments, the antibodies have at least 50% identity to SEQ ID NO: 31, alternatively at least 75% sequence identity, alternatively at least 80% sequence identity, alternatively at least 90% sequence identity, alternatively at least 95% sequence identity, alternatively at least 98% sequence identity, alternatively at least 100% sequence identity. In some embodiments, the modified protein has at least 100% sequence identity within CDRH1, CDRH2 and CDRH3 within SEQ ID NO: 31 (e.g., SEQ ID Nos. 37-39). In some embodiments, the antibodies further have 100% sequence identity with CDRL1, CDRL2 and CDRL3 within SEQ ID NO: 31 (e.g., SEQ ID NO: 35, the amino acid sequence DA, and SEQ ID NO: 36).

In some embodiments, the antibodies have substantial identity to the polypeptide found in SEQ ID NO: 37. In some embodiments, the antibodies have at least 50% identity to SEQ ID NO: 37, alternatively at least 75% sequence identity, alternatively at least 80% sequence identity, alternatively at least 90% sequence identity, alternatively at least 95% sequence identity, alternatively at least 98% sequence identity, alternatively at least 100% sequence identity. In some embodiments, the modified protein has at least 100% sequence identity within CDRH1, CDRH2 and CDRH3 within SEQ ID NO: 37 (e.g., SEQ ID Nos. 44-46). In some embodiments, the antibodies further have 100% sequence identity with CDRL1, CDRL2 and CDRL3 within SEQ ID NO: 43 (e.g., SEQ ID NO: 41, the amino acid sequence DN, and SEQ ID NO: 42).

In some embodiments, the antibodies have substantial identity to the polypeptide found in SEQ ID NO: 43. In some embodiments, the antibodies have at least 50% identity to SEQ ID NO: 43, alternatively at least 75% sequence identity, alternatively at least 80% sequence identity, alternatively at least 90% sequence identity, alternatively at least 95% sequence identity, alternatively at least 98% sequence identity, alternatively at least 100% sequence identity. In some embodiments, the modified protein has at least 100% sequence identity within CDRH1, CDRH2 and CDRH3 within SEQ ID NO: 43 e.g., SEQ ID Nos. 51-53). In some embodiments, the antibodies further have 100% sequence identity with CDRL1, CDRL2 and CDRL3 within SEQ ID NO: 43 (e.g., SEQ ID NO: 47, the amino acid sequence GA, and SEQ ID NO: 48).

In some embodiments, the antibodies have substantial identity to the polypeptide found in SEQ ID NO: 49. In some embodiments, the antibodies have at least 50% identity to SEQ ID NO: 49, alternatively at least 75% sequence identity, alternatively at least 80% sequence identity, alternatively at least 90% sequence identity, alternatively at least 95% sequence identity, alternatively at least 98% sequence identity, alternatively at least 100% sequence identity. In some embodiments, the modified protein has at least 100% sequence identity within CDRH1, CDRH2 and CDRH3 within SEQ ID NO: 49 (e.g., SEQ ID Nos. 58-60). In some embodiments, the antibodies further have 100% sequence identity with CDRL1, CDRL2 and CDRL3 within SEQ ID NO: 49 (e.g., SEQ ID NO: 53, the amino acid sequence QD, and SEQ ID NO: 54).

In some embodiments, the antibodies have substantial identity to the polypeptide found in SEQ ID NO: 55. In some embodiments, the antibodies have at least 50% identity to SEQ ID NO: 55, alternatively at least 75% sequence identity, alternatively at least 80% sequence identity, alternatively at least 90% sequence identity, alternatively at least 95% sequence identity, alternatively at least 98% sequence identity, alternatively at least 100% sequence identity. In some embodiments, the modified protein has at least 100% sequence identity within CDRH1, CDRH2 and CDRH3 within SEQ ID NO: 55 (e.g., SEQ ID Nos. 65-67). In some embodiments, the antibodies further have 100% sequence identity with CDRL1, CDRL2 and CDRL3 within SEQ ID NO: 55 (e.g., SEQ ID NO: 59, the amino acid sequence GE, and SEQ ID NO: 60).

In some embodiments, the antibodies have substantial identity to the polypeptide found in SEQ ID NO: 61. In some embodiments, the antibodies have at least 50% identity to SEQ ID NO: 61, alternatively at least 75% sequence identity, alternatively at least 80% sequence identity, alternatively at least 90% sequence identity, alternatively at least 95% sequence identity, alternatively at least 98% sequence identity, alternatively at least 100% sequence identity. In some embodiments, the modified protein has at least 100% sequence identity within CDRH1, CDRH2 and CDRH3 within SEQ ID NO: 61 (e.g., SEQ ID Nos. 72-74). In some embodiments, the antibodies further have 100% sequence identity with CDRL1, CDRL2 and CDRL3 within SEQ ID NO: 61 (e.g., SEQ ID NO: 65, the amino acid sequence EV, and SEQ ID NO: 66).

In some embodiments, the antibodies have substantial identity to the polypeptide found in SEQ ID NO: 67. In some embodiments, the antibodies have at least 50% identity to SEQ ID NO: 67, alternatively at least 75% sequence identity, alternatively at least 80% sequence identity, alternatively at least 90% sequence identity, alternatively at least 95% sequence identity, alternatively at least 98% sequence identity, alternatively at least 100% sequence identity. In some embodiments, the modified protein has at least 100% sequence identity within CDRH1, CDRH2 and CDRH3 within SEQ ID NO: 67 (e.g., SEQ ID Nos. 79-81). In some embodiments, the antibodies further have 100% sequence identity with CDRL1, CDRL2 and CDRL3 within SEQ ID NO: 67 (e.g., SEQ ID NO: 71, the amino acid sequence AN, and SEQ ID NO: 72).

In some embodiments, the isolated BBB-selective antibody or antigen-binding fragment thereof comprises or consists of an amino acid sequence selected from: (a) SEQ ID NO: 25; (b) SEQ ID NO: 1; (c) SEQ ID NO: 7; (d) SEQ ID NO: 13; (e) SEQ ID NO: 19; (f) SEQ ID NO: 31; (g) SEQ ID NO: 37; (h) SEQ ID NO: 43; (i) SEQ ID NO: 49; (j) SEQ ID NO: 55; (k) SEQ ID NO: 61; and (1) SEQ ID NO: 66.

The present invention also encompasses modified forms of the BBB-selective antibodies and antigen-binding fragments disclosed herein. For instance, one may wish to modify the affinity, specificity or other properties of the disclosed antibodies. For example, in some embodiments, the BBB-selective antibody or antigen-binding fragment thereof is humanized. The term "humanized antibody" refers to antibodies in which the human antibody framework has been modified to comprise fragments of antibodies taken from a different species that provide antigen specificity. This term includes chimeric antibodies containing minimal sequence derived from non-human immunoglobulin. For example, the hypervariable region residues of a human antibody may be replaced by hypervariable region residues from a non-human species (e.g., mouse, rat, rabbit, or nonhuman primate) having the desired specificity, affinity, and capacity. In some instances, Fv framework region (FR) residues of the human immunoglobulin are replaced by corresponding non-human residues. In some instances, humanized antibodies may comprise residues that are not found in the recipient antibody or in the donor antibody and are made to further refine antibody performance. In general, the humanized antibody will comprise substantially all of at least one, and typically two or three variable domains, in which all or substantially all of the hypervariable loops correspond to those of a non-human immunoglobulin and all or substantially all of the FR regions are those of a human immunoglobulin sequence. In some aspects, the humanized antibody will also optionally comprise at least a portion of an immunoglobulin constant region (Fc), typically that of a human immunoglobulin. For further details, see Jones et al., Nature 321:522-525 (1986); Reichmann et al., Nature 332: 323-329 (1988); and Presta, Curr. Op. Struct. Biol. 2:593-596 (1992). For example, in one embodiment, the invention provides a humanized scFv antibody or antigen binding fragment thereof comprising the CDR domains from scFV46.1 or the other scFvs described herein (scFv3, scFv9, scFv17, scFv26, scFv6i, scFv5A, scFv2F, scFv4B, scFv5E-0.4, scFvB3-R3, scFv22Ch).

Further, one may wish to engraft one or more CDRs from scFvs (i.e., the entire scFv or fragments thereof) disclosed herein into alternate scaffolds. For example, in some embodiments, the BBB-selective antibody or antigen-binding fragment thereof is engrafted within a full IgG scaffold of human or other species or a scFv scaffold of human or other species of origin. Standard molecular biological techniques can be used to transfer the DNA sequences encoding an antibody's CDR(s) or scFv into an alternate scaffold.

In some embodiments, the BBB-selective antibody or antigen-binding fragment thereof is a single chain variable fragment (scFv). The term "single-chain variable fragment," "single-chain fragment variable" or "scFv," as used herein, refers to a fusion protein of the variable regions of the heavy ($V_H$) and light chains ($V_L$) of immunoglobulins, connected with a short linker peptide of about ten to about 25 amino acids. The linker may be rich in glycine for flexibility, as well as serine or threonine for solubility, and can either connect the N-terminus of the $V_H$ with the C-terminus of the $V_L$, or vice versa. scFvs may often be produced in microbial cell cultures such as *E. coli* or *Saccharomyces cerevisiae*. ScFvs can also be produced in tissue culture, for example, in mammalian or human cell lines. ScFvs have many uses, e.g., flow cytometry, immunohistochemistry, and as antigen-binding domains of artificial T cell receptors. The present invention discloses scFvs. In one embodiment, the scFvs contain the three heavy chain variable domains, CDRH1, CDRH2, and CDRH3, and three light chain variable domains, CDRL1, CDRL2 and CDRL3, as described herein. In some embodiments, additional polypeptide sequence is used to link the CDR1, CDR2, and CDR3 to allow for the formation of the proper three-dimensional antigen-binding site of the antibody or fragment such that it is capable of binding to BBB (and in some examples binding and translocating the BBB).

In some embodiments, the BBB-selective antibody or antigen-binding fragment thereof is directly or indirectly linked to an agent, forming an "antibody conjugate". In some preferred embodiments, the antibody and the agent can translocate the BBB. As demonstrated in the examples, the antibodies or antigen-binding fragments thereof described herein can be conjugated to an agent and are able to bind the BBB and translocate across the BBB carrying the agent, which is able to accumulate in measurable amounts within the brain (as demonstrated in the mouse model). Suitable agents include any agent one wishes to deliver across the BBB to the brain, for example, therapeutic neurological agents or detection agents.

In general, methods of conjugating, linking and coupling antibodies to compounds are well known in the field, see Nat Biotechnol. (2005) 23(9):1137-46; Cancer Immunol Immunother. (2003) 52(5):328-37; and Adv Drug Deliv Rev. (2003) 55(2):199-215. For example, one may wish to link the antibodies of the present invention to an agent via primary amines (see Pharmaceutical Research (2007) 24(9): p. 1759-1771). For example, lysine residues of either antibody or agent may be functionalized using Traut's reagent (2-iminothiolane.HCL) yielding a thiol. The thiol group, now attached to the lysine residue, is reacted with a maleimide-functionalized drug or vector resulting in a stable thio-ether bond. One may optionally use a chemical spacer such as poly-ethylene glycol to reduce steric hindrance. Alternatively, one may wish to link the antibody to the agent non-covalently. For example, one could use biotin/streptavidin interaction (see Pharmaceutical Research (2007) 24(9): p. 1759-1771, incorporated by reference in its entirety). Lysine residues of either the antibody or agent may be biotinylated using one of a number of commercial methods (e.g., N-hydroxysuccinimide biotin analogs). Then, either the antibody or the agent (whichever one was not modified in the previous step) would be conjugated to streptavidin or one of its variants (e.g., neutravidin). The monobiotinylated reagent and the streptavidin-conjugated counterpart would be combined and the near-covalent binding affinity would keep the reagents together. Conjugation may optionally be accomplished with a cleavable or non-cleavable linker.

In some examples, the agent is a polypeptide that is translated concurrently with the antibody polypeptide sequence as a fusion protein. One may wish to express the antibody as a fusion protein with a pharmacologically or therapeutically relevant peptide. For example, one may wish to express a scFv of the present invention with a protein linker and a protein therapeutic. Standard molecular biology techniques (e.g., restriction enzyme based subcloning or homology based subcloning) can be used to place the DNA sequence encoding the agent in frame with the targeting vector. Optionally, a protein linker may be added to avoid steric hindrance. The fusion protein is then produced as one peptide in a cell (e.g., yeast, bacteria, insect, or mammalian cell) and purified before use. Note that the agent does not need to be a whole protein. (For example, it can be a single peptide chain as a subunit in a protein with more than one peptide. The other peptides can be co-expressed with the vector fusion and allowed to associate in the cell or after secretion).

The term "agent" as used herein includes any useful moiety that allows for the purification, identification, detection, diagnosing, imaging, or therapeutic use of the antibody of the present invention. The agent is selected according to the purpose of the intended application (e.g., treatment of a particular disease). In some embodiments, the agent is a therapeutic agent, pharmaceutical agent, or a combination thereof. Exemplary therapeutic agents include, without limitation, pharmaceuticals, biologics, toxins, fragments of toxins, alkylating agents, enzymes, antibiotics, antimetabolites, antiproliferative agents, chemotherapeutic agents, hormones, neurotransmitters, DNA, RNA, siRNA, oligonucleotides, antisense RNA, aptamers, diagnostics, radioopaque dyes, radioactive isotopes, fluorogenic compounds, magnetic labels, nanoparticles, marker compounds, lectins, compounds that alter cell membrane permeability, photochemical compounds, small molecules, liposomes, micelles, gene therapy vectors, viral vectors, immunological therapeutic constructs, and other drugs. Specifically, neurological drugs or drugs that act on the brain of a subject are suitable for use in the present invention.

For use herein, the term "antibody conjugate" includes an antibody described above linked directly or indirectly to an agent.

In other embodiments, the agents is a diagnostic agent or imaging agent. Suitable imaging agents include, without limitation, epitope tags, detectable markers, radioactive markers, and nanoparticles. Suitable epitope tags are known in the art and include, but are not limited to, 6-Histidine (His), hemagglutinin (HA), cMyc, GST, Flag tag, V5 tag, NE-tag, among others. Epitope tags are commonly used as a purification tag (i.e., an agent that allows isolation of the antibody from other non-specific proteins). Suitable detectable markers include luminescent markers, fluorescent markers (e.g., fluorescein, fluorescein isothiocyanate, rhodamine, dichlorot[pi]azinylamine fluorescein, green fluorescent protein (GFP), red fluorescent protein (RFP), blue fluorescent dyes excited at wavelengths in the ultraviolet (UV) part of the spectrum (e.g., AMCA (7-amino-4-methylcoumarin-3-acetic acid); Alexa Fluor 350), green fluorescent dyes excited by blue light (e.g., FITC, Cy2, Alexa Fluor 488), red fluorescent dyes excited by green light (e.g., rhodamines, Texas Red, Cy3, Alexa Fluor dyes 546, 564 and 594), or dyes excited with infrared light (e.g., Cy5), dansyl chloride, and phycoerythrin), or enzymatic markers (e.g., horseradish peroxidase, alkaline phosphatase, beta-galactosidase, glucose-6-phosphatase, and acetylcholinesterase). Suitable radioactive markers include, but are not limited to, $^{125}I$, $^{131}I$, $^{35}S$ or $^{3}H$. Suitable nanoparticles, including metal nanoparticles and other metal chelates, are known in the art and include, but are not limited to, gold nanoparticles (B. Van de Broek et al., ACSNano, Vol. 5, No. 6, 4319-4328, 2011), quantum dots (A. Sukhanova et al., Nanomedicine, 8 (2012) 516-525), magnetic nanoparticles ($Fe_3O_4$), silver nanoparticles, nanoshells, and nanocages. Conventional linking methods of linking a substance of interest to a polypeptide, in particular an antibody or antigen-binding fragment thereof, are known in the art (e.g., see Ternynck and Avrameas, 1987, "Techniques immunoenzymatiques" Ed. INSERM, Paris or G.T. Hermanson, Bioconjugate Techniques, 2010, Academic Press). Many chemical cross-linking methods are also known in the art. Cross-linking reagents may be homobifunctional (i.e., having two functional groups that undergo the same reaction) or heterobifunctional (i.e., having two different functional groups). Numerous cross-linking reagents are commercially available. Detailed instructions for their use are readily available from the commercial suppliers. A general reference on polypeptide cross-linking and conjugate preparation is: WONG, Chemistry of protein conjugation and cross-linking, CRC Press (1991).

Compositions comprising the BBB-targeting antibodies or antigen-binding fragments thereof are also contemplated herein. The compositions may include BBB-targeting antibodies or antigen-binding fragments thereof which are conjugated to an agent. The compositions may further include a pharmaceutically acceptable carrier. The pharmaceutically acceptable carrier may be selected based upon the route of administration desired. For example, the BBB-targeting antibodies or antigen-binding fragments thereof may be provided in combination with liposomes, nanoparticles or other analogous carriers loaded with a pharmaceutically active compound. Methods of preparing such compositions are known in the field (e.g., see Sugano et al., Antibody Targeting of Doxorubicin-loaded Liposomes Suppresses the Growth and Metastatic Spread of Established Human Lung Tumor Xenografts in Severe Combined Immunodeficient Mice Cancer Research 60, 6942-6949, Dec. 15, 2000 and Martin et al., Nanomaterials in Analytical Chemistry, Analytical Chemistry News & Features, May 1, 1998; pp. 322 A-327 A). As used herein, the phrase "antibody in combination with a pharmaceutically active compound" shall not be limited by the method of manufacture and such compositions may be produced by, but not limited to, techniques of conjugating, linking, coupling and decorating known in the art.

Nanoparticles are particle of matter that are between 1 and 100 nanometers (nm) in diameter, and can be made of many different materials, including, for example, lipid-based nanoparticles, polymeric nanoparticles (e.g., synthesized from natural or synthetic materials, monomers, preformed polymers, including, polymersome, dendrimer, polymer micelle, nanosphere, etc.), inorganic nanoparticles (e.g., silica, iron oxide, gold, etc), among others. Liposomes are vesicles comprising one or more phospholipid bilayers. These vesicles can be used to encapsulate water soluble molecules in the aqueous inner cavity, while water insoluble molecules can be embedded in the hydrophobic region of the lipid bilayer. Liposomes may be small (0.025-0.05.μm) or large (0.05-10 μm). Optionally, the liposomes described herein may have diameters of about 50-5,000 nm, of about 50-1,000 nm, or of less than 5,000 nm or 1,000 nm. Liposomes can be unilamellar (having one lipid bilayer) or multilamellar (having two or more lipid bilayers), and a population of liposomes may contain both unilamellar and multilamellar liposomes. See, e.g., Akbarzadeh et al., Nanoscale Res. Letters, 8:102-110 (2013), which is incorporated by reference herein in its entirety. Multilamellar liposomes may optionally include cross-linkages between the lipid bilayers. Such cross-linkages include, for example, boronic ester or thioketal cross-linkages. Liposomes can be prepared using phospholipids from natural or synthetic sources. Liposomes are known in the art and can include, cationic lipids, neutral lipids, or non-cationic lipids. Methods of making liposomes are known in the art.

An inner cavity is the space inside the innermost lipid bilayer of a liposome and an interbilayer space or interlamellar space is the space between any two lipid bilayers. For example, in a multilamellar liposome having three lipid bilayers, the inner cavity would be the space within the first (inner-most) lipid bilayer, an interbilayer space would be the space between the first and second (middle) lipid bilayers, and another interbilayer space would be between the second and third (outer-most) lipid bilayers.

Lipids used to prepare liposomal lipid bilayers include, but are not limited to, phospholipids, sphingolipids, glycosphingolipids, saturated glycerides, steroids (e.g., cholesterol), synthetic phospholipids, and any combinations thereof. Optionally, one or more lipids in the lipid bilayer contains a hydroxyl group and/or a diol head group. Optionally, the hydrocarbon chains of the lipids in the lipid bilayer are the same or approximately the same length. The lipids of the lipid bilayer can include one or more different types of lipids. The two or more lipids may be packed together to form a bilayer and certain lipids may be integrated into the hydrophobic portion of the bilayer. It should be noted that a lipid bilayer may be continuous or composed of islands of lipid bilayer. It should also be understood that the hydrocarbon chains of the various lipids can be of the same or differing lengths.

Although liposomal lipid bilayers typically contain lipids as the predominant structural molecule, the bilayers or the lipids themselves may contain one or more additional components. Optionally, the additional components may include, but are not limited to, detergents, protein-conjugated molecules, PEGylated molecules, and molecules with aliphatic anchors. The additional components may be inserted into lipid bilayers by, for instance, hydrophobic interaction, non-covalent attachment to lipid bilayers, or covalent attachment to lipid bilayers (e.g., via bond formation with lipid head groups). The additional components in the liposomal lipid bilayers may alter the properties of the lipid bilayer, including but not limited to, membrane fluidity, permeability, flexibility, fusogenicity, stability, charge/electrostatics, symmetry, cellular uptake, degradation, and the like. By way of example, addition of cholesterol to a lipid bilayer decreases permeability and fluidity of the liposome, whereas PEG increases the duration of circulation. See e.g., Bozzuto et al., Intl J. of Nanomedicine, 10: 975-999 (2015), which is incorporated herein by reference in its entirety.

Compositions are provided that include one or more of the disclosed antibodies that bind BBB. Compositions comprising antibodies that are conjugated to and/or directly or indirectly linked to an agent are also provided. The compositions can be prepared in unit dosaged forms for administration to a subject. The amount and timing of administration are at the discretion of the treating clinician to achieve the desired outcome. The antibody can be formulated for systemic or local (such as intravenous, intrathecal, intra-cranial) administration. In one example, the antibody is formulated for parenteral administration, such as intravenous administration.

As used herein, "pharmaceutical composition" means therapeutically effective amounts of the antibody together with a pharmaceutically-acceptable carrier. "Pharmaceutically acceptable" carriers are known in the art and include, but are not limited to, for example, suitable diluents, preservatives, solubilizers, emulsifiers, liposomes, nanoparticles and adjuvants. Pharmaceutically acceptable carriers are well known to those skilled in the art and include, but are not limited to, 0.01 to 0.1 M and preferably 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include isotonic solutions, alcoholic/aqueous solutions, emulsions or suspensions, including saline and buffered media.

Pharmaceutical compositions of the present disclosure may include liquids or lyophilized or otherwise dried formulations and may include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

The pharmaceutical compositions can be sterilized by conventional, well known sterilization techniques. The compositions may contain pharmaceutically acceptable additional substances as required to approximate physiological conditions such as a pH adjusting and buffering agent, toxicity adjusting agents, such as, sodium acetate, sodium chloride, potassium chloride, calcium chloride, sodium lactate, and the like.

In some embodiments, the antibodies are provided in lyophilized form and rehydrated with sterile water or saline solution before administration. In some embodiments, the antibodies are provided in sterile solution of known concentration. In some embodiments, the antibody composition may be added to an infusion bag containing 0.9% sodium chloride, USP and in some cases, administered in a dosage of from 0.5 to 15 mg/kg of body weight.

In another aspect, the present invention provides nucleic acid sequences encoding the BBB-selective antibodies or antigen-binding fragments disclosed herein. In some embodiments, the nucleic acid sequences comprise conservative or inconsequential substitutions or deletions.

In another aspect, the present invention provides vectors comprising a DNA sequence encoding the BBB-selective antibodies or antigen-binding fragments disclosed herein. In some embodiments, the invention may be an expression vector comprising an expression cassette encoding the BBB-specific antibody or antigen-binding fragment thereof, and in some examples, encoding the agent in addition to the BBB-specific antibody or antigen-binding fragment thereof. For example, the polynucleotide encoding the antibody or antigen-binding fragment thereof may be under the control of a heterologous transcriptional promoter allowing the regulation of the transcription of said polynucleotide in a cell. Said polynucleotide can also be linked to appropriate control sequences to allow for regulation of its translation in a cell.

In another aspect, the present invention provides cells expressing the BBB-selective antibodies or antigen-binding fragments disclosed herein (including, for example the BBB-selective antibodies or antigen-binding fragments thereof and the agent), and cells comprising the vectors disclosed herein. In some embodiments, the cells comprise an expression vector encoding an antibody or antigen-binding fragment thereof is disclosed herein. It should be appreciated that the cell may be any cell capable of expressing antibodies, and may be either a prokaryotic or a eukaryotic cell. Suitable cells include, without limitation, fungi, mammalian cells, insect cells (e.g., using a baculovirus expression system), plant cells (e.g., corn, rice, or *Arabidopsis*). See, generally, Verma, R. et al., J Immunol Methods. 1998 Jul. 1; 216(1-2):165-81. Cells include "transformants" and "transformed cells", which include the primary transformed cell and progeny derived therefrom without regard to the number of passages. Progeny may not be completely identical in nucleic acid content to a parent cell, and may contain mutations. Mutant progeny that have the same function or biological activity as screened or selected for in the originally transformed cell are encompassed by the present invention.

Methods:

In another aspect, the present invention provides methods of targeting an agent to and/or across the BBB of a subject. The methods involve administering a BBB-selective antibody or antigen-binding fragment disclosed herein. In these methods, the antibody is (1) directly or indirectly linked to the agent, (2) is able to specifically target the BBB, and (3) in some examples, able to translocate the BBB after targeting this tissue. In some embodiments, the agent is able to accumulate at nM levels in the brain of a subject. In some embodiments, the antibodies are administered through an intravenous injection or through intra-peritoneal and subcutaneous methods. Such a method includes administering a pharmaceutically active or therapeutic compound in combination with a purified BBB-targeting antibody or antigen-binding fragment thereof (described herein) to a subject such that the antibody/antigen-binding fragment thereof directs delivery of the agent to and/or across the blood brain barrier into the subject's brain.

In another aspect, the present invention provides methods of targeting a therapeutic agent to the BBB of a subject. The methods involve administering a BBB-selective antibody or antigen-binding fragment disclosed herein. In these methods, the antibody is directly or indirectly linked to the therapeutic agent such that the antibody directs delivery of the therapeutic agent to and/or across the BBB into the subject's brain.

In the present methods, the antibodies may be provided in a lyophilized form and rehydrated with sterile water or saline solution before administration. Alternatively, the antibodies may be provided in a sterile solution of known concentration. Further, the antibody composition may be added to an infusion bag containing 0.9% sodium chloride, USP and in some cases, administered in a dosage of from 0.5 to 15 mg/kg of body weight.

Kits:

In a final aspect, the present invention provides kits comprising the BBB-selective antibodies or antigen-binding fragments disclosed herein. The kits may be used to carry out the methods described herein.

Definitions

Administering. As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, intradermal administration, intrathecal administration and subcutaneous administration. Administration can be continuous or intermittent. In various aspects, a preparation can be administered therapeutically; that is, administered to treat an existing disease or condition.

Chimeric antibody. The term "chimeric antibody" refers to an antibody comprising a variable region (i.e., binding region) from one source or species and at least a portion of a constant region derived from a different source or species, usually prepared by recombinant DNA techniques. For example, the antibodies disclosed in the present invention may be modified to be human antibodies that include the constant region from a human germline immunoglobulin sequences. The term "chimeric human antibody" includes all human antibodies that are prepared, expressed, created or isolated by recombinant means, such as antibodies isolated from a host cell (e.g., an SP2-0, NS0 or CHO cell) or from an animal (e.g., a mouse) that is transgenic for human immunoglobulin genes or antibodies. Such recombinant human antibodies have variable and, in some embodiments, constant regions derived from human germline immunoglobulin sequences in a rearranged form. Other forms of "chimeric antibodies" are those in which the class or subclass has been modified or changed from that of the original antibody. Such "chimeric" antibodies are also referred to as "class-switched antibodies." Methods for producing chimeric antibodies involve conventional recombinant DNA and gene transfection techniques, which are now well known in the art.

Complementarity determining region (CDR). The term "complementarity determining region" or "CDR," as used herein, refers to part of the variable chains in immunoglobulins (antibodies) and T cell receptors where these molecules bind to their specific antigen. As the most variable parts of the molecules, CDRs are crucial to the diversity of antigen specificities generated by lymphocytes. There are three CDRs (CDR1, CDR2 and CDR3), arranged non-consecutively, on the amino acid sequence of a variable domain of an antigen receptor. Since the antigen receptors are typically composed of two variable domains (on two different polypeptide chains: the heavy and light chain), there are six CDRs for each antigen receptor that can collectively come into contact with the antigen. A single whole antibody molecule has two antigen receptors and therefore contains twelve CDRs. Sixty CDRs can be found on a pentameric IgM molecule. Within the variable domain, CDR1 and CDR2 may be found in the variable (V) region of a polypeptide chain, and CDR3 includes some of V, all of diversity (D, heavy chains only) and joining (J) regions. Since most sequence variation associated with immunoglobulins and T cell receptors is found in the CDRs, these regions are sometimes referred to as hypervariable regions. Among these, CDR3 shows the greatest variability as it is encoded by a recombination of VJ in the case of a light chain region and VDJ in the case of heavy chain regions. The tertiary structure of an antibody is important to analyze and design new antibodies.

Monoclonal antibody. The terms "monoclonal antibody" or "monoclonal antibody composition" as used herein refer to a preparation of antibody molecules of a single amino acid composition. Monoclonal antibodies also include "human monoclonal antibodies", which display a single binding specificity and have variable and constant regions derived from human germline immunoglobulin sequences. Human monoclonal antibodies can be produced by a hybridoma, which includes a B cell obtained from a transgenic nonhuman animal (e.g., a transgenic mouse) having a genome comprising a human heavy chain transgene and a human light chain transgene fused to an immortalized cell.

Percentage of sequence identity. "Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Protein and nucleic acid sequence identities are evaluated using the Basic Local Alignment Search Tool ("BLAST"), which is well known in the art (Karlin and Altschul, 1990, *Proc. Natl. Acad. Sci.* USA 87: 2267-2268; Altschul et al., 1997, *Nucl. Acids Res.* 25: 3389-3402). The BLAST programs identify homologous sequences by identifying similar segments, which are referred to herein as "high-scoring segment pairs," between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990), the disclosure of which is incorporated by reference in its entirety. The BLAST programs can be used with the default parameters or with modified parameters provided by the user. The term "substantial identity" of amino acid sequences for purposes of this invention normally means polypeptide sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100%.

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% compared to a reference sequence using the programs described herein; preferably BLAST using standard parameters, as described. These values can be appropriately adjusted to determine corresponding identity of proteins encoded by two nucleotide sequences by taking into account codon degeneracy, amino acid similarity, reading frame positioning and the like.

"Substantial identity" of amino acid sequences for purposes of this invention normally means polypeptide sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100%.

Proteins. As used herein, the terms "proteins" and "polypeptides" are used interchangeably herein to designate a series of amino acid residues connected to the other by peptide bonds between the alpha-amino and carboxy groups of adjacent residues. The terms “protein” and “polypeptide” refer to a polymer of protein amino acids, including modified amino acids (e.g., phosphorylated, glycated, glycosylated, etc.) and amino acid analogs. “Protein” and “polypeptide” are often used in reference to relatively large polypeptides, whereas the term “peptide” is often used in reference to small polypeptides, but usage of these terms in the art overlaps. The terms “protein” and “polypeptide” are used interchangeably herein when referring to an encoded gene product and fragments thereof. Thus, exemplary polypeptides or proteins include gene products, naturally occurring proteins, homologs, orthologs, paralogs, fragments and other equivalents, variants, fragments, and analogs of the foregoing. The antibodies of the present invention are polypeptides.

Subject. As used herein “subject” or “patient” refers to mammals and non-mammals. “Mammals” means any member of the class Mammalia including, but not limited to, humans, non-human primates (e.g., chimpanzees, other apes, and monkey species), farm animals (e.g., cattle, horses, sheep, goats, and swine), domestic animals (e.g., rabbits, dogs, and cats) laboratory animals including rodents (e.g., rats, mice, and guinea pigs). Examples of non-mammals include, but are not limited to, birds, and the like. The term “subject” does not denote a particular age or sex. In one specific embodiment, a subject is a mammal, preferably a human.

Therapeutic agent. As used herein, the term “therapeutic agent” refers to any synthetic or naturally occurring biologically active compound or composition of matter which, when administered to an organism (human or nonhuman animal), induces a desired pharmacologic, immunogenic, and/or physiologic effect by local and/or systemic action. The term, therefore, encompasses those compounds or chemicals traditionally regarded as drugs, chemotherapeutics, and biopharmaceuticals including molecules such as proteins, peptides, hormones, nucleic acids, gene constructs and the like. Examples of therapeutic agents are described in well-known literature references, such as the Merck Index (14th edition), the Physicians’ Desk Reference (64th edition), and The Pharmacological Basis of Therapeutics (12th edition), and they include, without limitation, substances used for the treatment, prevention, diagnosis, cure or mitigation of a disease or illness; substances that affect the structure or function of the body, or pro-drugs, which become biologically active or more active after they have been placed in a physiological environment. Treating. For purposes of the present invention, “treating” or “treatment” describes the management and care of a subject for the purpose of combating the disease, condition, or disorder. Treating includes the administration of an antibody or antigen-binding fragment thereof of present invention to prevent the onset of the symptoms or complications, alleviating the symptoms or complications, or eliminating the disease, condition, or disorder. Specifically, the antibodies or antigen-binding fragments thereof can be used to treat a brain or neurological disorder, or for treating a cancer localized to the brain.

Vector. The term “vector,” or “recombinant vector” as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as “expression vectors”. Vectors, including expression vectors, comprise the nucleotide sequence encoding the antibodies or antigen-binding fragments described herein and a heterogeneous sequence necessary for proper propagation of the vector and expression of the encoded polypeptide. The heterogeneous sequence (i.e., sequence from a difference species than the polypeptide) can comprise a heterologous promoter or heterologous transcriptional regulatory region that allows for expression of the polypeptide. As used herein, the terms “heterologous promoter,” “promoter,” “promoter region,” or “promoter sequence” refer generally to transcriptional regulatory regions of a gene, which may be found at the 5' or 3' side of the polynucleotides described herein, or within the coding region of the polynucleotides, or within introns in the polynucleotides. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains (consensus sequences) responsible for the binding of RNA polymerase.

A recombinant expression cassette comprising a polynucleotide encoding the antibody or antigen-binding fragment thereof of the present invention is also contemplated. The polynucleotide may be under the control of a heterologous transcriptional promoter allowing the regulation of the transcription of said polynucleotide in a host cell. The present invention also provides a recombinant expression cassette comprising a polynucleotide according to the present invention under the control of a transcriptional promoter allowing the regulation of the transcription of said polynucleotide in a host cell. Said polynucleotide can also be linked to appropriate control sequences allowing the regulation of its translation in a host cell.

Host cell. The present invention also provides a host cell containing a recombinant expression cassette or a recombinant expression vector according to the present invention. The host cell is either a prokaryotic or eukaryotic host cell. The host cell is capable of expressing the antibodies of the present invention. Suitable host cells include, but are not limited to, mammalian cells and yeast cells. In some embodiments, the host cell may be a eukaryotic cell. The terms “host cell” refers to a cell into which exogenous nucleic acid has been introduced, including the progeny of such cells. Host cells include “transformants” and “transformed cells”, which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

The invention will be more fully understood upon consideration of the following non-limiting examples.

Examples

Drug delivery across the blood-brain barrier (BBB) remains a significant obstacle for the development of neurological disease therapies. The low penetration of blood-borne therapeutics into the brain can oftentimes be attributed to the restrictive nature of the brain microvascular endothelial cells (BMECs) that comprise the BBB. One strategy beginning to be successfully leveraged is the use of endogenous receptor-mediated transcytosis (RMT) systems as a means to shuttle a targeted therapeutic into the brain. Limitations of known RMT targets and their cognate targeting reagents include brain specificity, brain uptake levels and off-target effects, driving the search for new and potentially improved brain targeting reagent-RMT pairs. In the following Example, the inventors deployed human induced pluripotent stem cell (iPSC)-derived BMEC-like cells as a model BBB substrate on which to mine for new RMT-targeting antibody pairs. A nonimmune, human single-chain variable fragment (scFv) phage display library was screened for binding, internalization and transcytosis across iPSC-derived BMECs. Lead candidates exhibited binding and internalization into BMECs as well as binding to both human and mouse BBB in brain tissue sections. Antibodies targeted the murine BBB after intravenous administration with one particular clone, 46.1-scFv, exhibiting a 26-fold increase in brain accumulation (8.1 nM). Moreover, clone 46.1-scFv was found to associate with postvascular, parenchymal cells, indicating its successful receptor-mediated transport across the BBB. Such a new BBB targeting ligand could enhance the transport of therapeutic molecules into the brain.

Materials and Methods

Experimental Design: Sample size: Sample sizes were dependent on the particular assay and are presented in the figure legends. Rules for stopping data collection: Data were collected at a predefined endpoint as noted in the methods and figure legends, both for in vitro and in vivo assays. Data inclusion exclusion criteria: Generated data are presented in the manuscript inclusively. Outliers: Outlying data points were not removed from any presented data set. Selection of endpoints: Study endpoints were predefined for each assay and are noted in the methods section below. Replicates: All of the in vitro assays were performed with multiple replicates as described in the methods section and animal numbers were powered to measure statistically significant differences between groups if they existed. Research objectives: The overall goals of this study were to identify and characterize antibodies that could interact with and transport across the blood-brain barrier in vitro as well as target the blood-brain barrier in vivo after systemic administration. Research subjects or units of investigation: iPSC-derived BMECs, human and murine tissue sections, C57BL6 mice. Experimental design: These were controlled laboratory experiments. Initial screens identified lead scFvs displayed on phage. Subsequently, the scFvs were produced and analyzed for murine and human tissue binding, BMEC internalization and murine brain uptake. Randomization: Mice were randomly assigned to control and test antibody groups. Blinding: Researchers were generally not blinded given that individual researchers performed each step of the process from gene cloning to murine administration making blinding impractical for this proof-of-concept study.

Cell culture: BMEC differentiation was performed as previously described using the IMR90-C4 iPSC line and retinoic acid induction (17, 18). At day 8 of differentiation, BMECs were plated on collagen/fibronectin coated tissue culture plates or 1 μm pore size poly-ester transwells (Corning #CLS3462). The primary human lung and heart microvascular endothelial cells (hLECs and hCECs, CC-2527 and CC-7030) were obtained from LONZA (Walkersville, MD), and cultured as per manufacturer's instructions.

Phage screen: All the screening methods are adapted from protocols outlined in Zhou and Marks using the previously described fd-tet based human scFv library (22, 42, 43). Initially, the human scFv library was pre-subtracted by serial application on hLECs and hCECs grown on T-75 flasks. All screening rounds were performed in appropriate culture media for each cell type. In each round, $10^{11}$ colony forming units (CFU) were applied to a confluent cell monolayer. Pre-subtraction rounds were performed by incubating the library on monolayers for 1 hr on ice, while internalization rounds on BMECs were performed by incubating the phage library on BMECs for 1 hr at 37° C. Following phage internalization, media was aspirated and cells were washed 1× with stripping buffer I (150 mM NaCl, 100 mM Glycine, pH 2.5) and 2× with stripping buffer II (500 mM NaCl, 50 mM Glycine, 0.2M Urea, pH 2.8) for 5 min at RT to remove membrane bound phage. BMECs were detached by trypsin treatment and spun down at 300 g at 4° C. for 5 min. The cell pellet was then resuspended in ice-cold lysis buffer (triethanolamine 100 mM), incubated on ice for 15 min, and neutralized (Tris-HCl pH 7.4). Phage eluted from each selection round were then used to infect log phase *E. coli* TG1 cells. Phage particles were rescued from the bacteria, amplified and used for subsequent rounds of antibody screening as previously described (30). A total of 1 pre-subtraction and 3 internalization rounds were performed.

For transcytosis screens, $10^{11}$ CFU from the third internalization round was dosed on top of a BMECs monolayer on a 1 μm pore size transwells with a minimum TEER of 1000 ohm-cm$^2$ and allowed to transcytose for 3 hrs at 37° C. before harvesting phage containing media from the bottom chamber for TG1 infection. For the competition transcytosis screen selection, $10^{11}$ CFU from the third internalization round were dosed onto BMECs along with 1 μM of soluble scFv 3 and 22Ch and allowed to transcytose for 3 hrs at 37° C. before harvesting phage containing media from the bottom chamber for TG1 infection.

Individual phage-infected TG1 colonies were grown overnight, and DNA was heat-extracted and PCR amplified using primers that flank the scFv gene. The primer sequences were 5'-TTTTTGGAGATTTTCAACGTGA-3' (SEQ ID NO: 73), and 5'-GAATTTTCTGTATGAGGTTTTGCTAAA-3' (SEQ ID NO: 74) for the forward and reverse primers, respectively. PCR fragments were then Sanger sequenced.

Phage immunocytochemistry: BMECs were purified on 96-well tissue culture plates as described above. The day of the assay, each well of BMECs was blocked with 250 μL of PBS with calcium and magnesium (PBSCM; PBS with 1 mM of calcium chloride and 0.5 mM of magnesium sulfate) supplemented with 40% goat serum (PBSCMG) (Sigma-Aldrich, #G6767). The wells were washed three times with 250 μL of PBSCM. Next, cells were fixed with paraformaldehyde (PFA, 4% w/v in PBS) for 10 min at RT. Overnight cultures of phage harboring bacteria were centrifuged, and 50 μL of the phage containing supernatant from each sample were incubated directly on the BMECs in the presence of 100 μL of fresh PBSCMG. The plate was incubated for 1 hr at 4° C. and then washed once. An anti-M13 antibody (GE healthcare #27942001) diluted 1:500 in PBSCMG was incubated in each well for 1 hr at 4° C. Cells were washed with PBSCM, and incubated with secondary antibody, goat anti-mouse AlexaFluor488 for 30 min at 4° C. Next, the cells were washed three times in PBSCM and post-fixed for 8 min at room temperature with PFA. The plate was then imaged on an Olympus epifluorescence microscope (Center Valley, PA).

Soluble scFv and scFv-Fc preparation: The following method for production of soluble scFv-His6 fusions is based on a protocol described in (30). An overnight bacterial culture transformed with the scFv secretion plasmid was used to inoculate 2×YT medium containing 100 μg/mL ampicillin and 0.1% glucose, which was then grown at 37° C. until an $OD_{600\ nm}$ of 0.9 was reached. Expression was induced by addition of 1 mM isopropyl-β-D-thiogalactopyranoside (IPTG, Fisher Scientific, #50213380) and bacteria allowed to grow for 4 hrs at 30° C. The bacteria was harvested and the scFv recovered by serial incubation with a periplasmic extraction buffer (PPB, 200 g/L sucrose, 1 mM EDTA, 30 mM tris-HCl, pH 8.0) supplemented with DNAse I (Roche Applied Sciences, #10104159001) to 100 μg/mL, and complete Mini protease inhibitor cocktail tablets (Roche Applied Sciences, #11836153001) followed by an osmotic shock buffer (OSB, 5 mM magnesium sulfate in ddH2O) supplemented with DNAse I and complete Mini protease inhibitor cocktail. The resulting solution was syringe filter sterilized, and dialyzed against PBS+10 mM imidazole. The scFv were purified from the crude extract with Qiagen Ni-Nta Spin Columns (Qiagen #31014) using manufacturer recommended protocol for purification. The purified scFvs were eluted and subsequently dialyzed against PBS, and the purity of the scFv was verified by sodium dodecyl sulfate-polyacry-lamide gel electrophoresis (SDS-PAGE) and Coomassie blue staining. Soluble scFvs were pre-dimerized with rabbit polyclonal anti c-myc antibody (Thermo fisher #PA1-981) in 4:1 molar ratio for 2 hrs in PBSG (10% goat serum in PBS) and used as dimers for all downstream assays.

For scFv-Fc fusion production, scFv genes were fused to rabbit Fc region by subcloning into a pIRES-rabbit Fc vector (44) using NheI and AgeI restriction sites via standard PCR amplification, restriction digestion, and ligation procedures. As a negative control, a fusion of the same rabbit Fc to a variable lymphocyte receptor that binds to human H antigen trisaccharide was used (44, 45; negative control, Ctrl-Fc). Large-scale DNA purification for HEK 293F transfection was done with ZymoPURE II plasmid kit (Zymo Research #D4200), and 293fectin (ThermoFisher #12347019) transfection reagent was used. Transfected cultures were then incubated for 5 days at 370 C, 8% $CO_2$, 135 rpm in a humidified incubator and the supernatant containing scFv-Fcs was separated from the cell mass via centrifugation and filtration. scFv-Fcs were purified from the cleared supernatant via protein A/G chromatography (ThermoFisher #20423). After elution with 100 mM Citric Acid pH 3, the solution was neutralized with 1M Tris-base pH 9 and concentrated with protein concentrator (ThermoFisher #88502) before 4° C. storage. Total protein concentration was quantified using UV 280 absorbance and extinction coefficients generated by ExPASy (web.expasy.org/protparam/).

Cell based assays: Membrane binding and endocytosis assay: BMECs were purified on Lab Tek II chamber slides (Nunc #154917). Cells were washed once with PBS and incubated with blocking buffer PBSG (10% goat serum in PBS) for 30 min on ice. Pre-dimerized scFvs (13.2 μg/ml) or scFv-Fc (5 μg/ml) were added to BMECs and incubated for additional 30 min on ice to allow binding. The chamber slides were then transferred at 37° C. for 45 min to allow internalization. Afterwards, cells were washed with cold PBS and incubated with anti-rabbit AlexaFluor555, 1:1000 in PBSG for 30 min on ice to label the membrane-bound fraction of scFv-Fcs. Cells were washed once more on ice, fixed with 4% PFA on ice for 10 min and permeabilized with 0.2% Triton X for 2 min. Anti-rabbit AlexaFluor488, 1:1000 in PBSG was used to label the internalized fraction for 30 min at RT. Finally, cells were washed and mounted with ProLong Gold antifade reagent with DAPI (Invitrogen, P36935). Images were acquired on Zeiss Axio Imager Z2 Upright microscope.

Internalization assay: BMECs were purified on 96-well flat-bottomed plates (Corning #3539948). Cells were serum starved for 1 hr at 37° C. in serum free endothelial medium. 1 μM purified scFv-Fc diluted in serum free medium were applied to cells. For temperature dependent internalization experiments, one group of samples was incubated at 37° C. and one group with the same concentration of scFv-Fc was incubated at 4° C. for 1 hr. After scFv-Fc incubation, cell membrane-bound antibodies were stripped by 5X acid washing (100 mM Citric Acid pH 3) on ice. Cells were fixed with 4% PFA for 8 min and blocked and permeabilized with 0.1% Triton X diluted in odyssey blocking buffer (LICOR #927-40000) for 15 min. Internalized scFv-Fcs were detected by incubation for 1 hr at 4° C. with IRdye800CW goat-anti-rabbit IgG pAb (LICOR #925-32211) and cell number in each well measured with CellTag (LICOR #926-041090), both diluted in odyssey blocking buffer. After primary antibody incubation, BMECs were washed on ice 7X with PBS 0.05% Tween-20, and signal from each well measured with a LICOR Odyssey Imager with a focus offset of 3 mm and resolution of 169 μm. ScFv-Fc signal in each well was normalized to total cell number by dividing with the equivalent CellTag signal.

Equilibrium binding measurements: BMECs were purified on 96-well flat-bottomed plates, washed 2× with PBS, and fixed with 2% PFA for 8 min. Fixed cells were blocked and permeabilized as described above for LICOR imaging. Apparent equilibrium affinity titration measurements were performed by incubating fixed cells with a range of scFv-Fc concentrations ranging from 1 nM to 1 μM at room temperature for 2 hr. After extensive washing with PBS 0.05% Tween-20 at 4° C., cells were labeled for scFv-Fc detection and for total cell number evaluation with IRdye reagents and CellTag as described above. Fraction of cellular antigens bound by scFv-Fc was quantified using background subtracted, total cell number normalized binding signal and the data was fit to a bimolecular equilibrium binding model to determine the apparent dissociation constant ($K_D$).

Competition assay: scFv-Fcs were pre-incubated with $10XK_D$ concentrations of recombinant receptor ecto-domain proteins rIR (R&D Systems #1444-IR) and rhTfR (R&D Systems #2474-TR) in PBS plus 1% BSA for 30 min at room temperature and then applied to serum starved BMECs in 96 well plates to allow scFv-Fcs to bind to membrane antigens. Plates were incubated at 4° C. for 2 hrs, and extensively washed, fixed and labeled with IRdye reagents for detection as described above. Total signal of the receptor-competed scFv-Fcs was compared to non-competed scFv-Fc signal intensity.

SDS-PAGE: scFv-Fcs were mixed with SDS containing sample buffer without reducing reagent and heated for 10 min prior to loading onto a 4-12% Bis-Tris gel (ThermoFisher #NP0321). Gels were stained with Coomassie blue.

Flow cytometry: BMECs were cultured in 6 wells plate as described above. The cells (~$2\times10^6$ cells/sample) were washed in PBS and detached from the culture plate with versene treatment for 1 hr at 37° C. The cells were transferred to 1.5 mL tubes and blocked for 1 hr at 4° C. with PBS 1% BSA while rotating. $10^{11}$ CFU of phage (either from each round of panning, or negative control anti-botulinum toxin scFv displaying phage) were incubated with blocked BMECs for 1 hr at 4° C. Next, cells were washed 3× with PBS 1% BSA to remove weakly bound phage and labeled with anti-M13 antibody as described above. The cells were washed two times, resuspended in flow buffer (PBS+0.1% BSA+5 mM EDTA), and analyzed on a flow cytometer (Becton Dickinson FACSCalibur).

Immunolabeling of human and mouse brain cryosections: Human brain tissue samples were obtained with approval from the University of Wisconsin-Madison Institutional Review Board and samples were snap frozen. Mouse brains were snap frozen in liquid nitrogen. Human and mouse tissue were cryosectioned in 8 and 30 μm sections on Thermo Scientific Microm HM 525. Due to the unknown structure of the corresponding antigens, multiple modes of fixation were used. Prior to immunolabeling, sections were fixed with either 4% PFA for 20 min at RT or in cold acetone at −20° C. for 20 min. In some instances, sections were post-fixed after incubation with scFv-Fcs. Sections fixed with PFA were, additionally, permeabilized with 0.2% Tx-100 in PBS. Sections were blocked with 10% goat serum in PBS (PBSG) for 30 min at room temperature. ScFv-Fcs (5 μg/ml) were incubated on human and mouse brain sections for 24 hrs at 4° C. In human sections, the blood vessels were labeled with mouse anti-human PECAM1/CD31 (Cell Sciences #MON6002-1), diluted 1:50 in PBSG for 2 hrs at RT and secondary goat anti-mouse AlexaFluor488 (1:1000). The blood vessels in mouse brain sections were directly labeled with the lectin LelDyLight488 (Vector laboratories Lel Dylight488). Tested antibodies were labeled with goat anti-rabbit AlexaFluor555 (1:1000) in PBSG. Sections were mounted with ProLong Gold antifade reagent with DAPI (Invitrogen, P36935), and mouse and human brains analyzed on Leica SP8 3×STED Confocal.

Immunolabeling of Mouse Brain Cryosections after IV Administration of Antibodies:

Animal studies were approved by the Institutional Animal Care and Use Committee (IACUC) at the University of Wisconsin-Madison. Mice C57BL6, 5-6 weeks old, were injected intravenously via the retroorbital route with scFv-Fcs in a dose 5 mg/kg. Mice were subjected to whole-body perfusion at 5 ml/min for 5 min with a PBS, supplemented with 100 U/ml heparin, 4 μg/ml fluorescently labeled lectin (LEL Dylight488 Vector laboratories) and 0.1% BSA, followed by additional 5 min perfusion with 4% PFA in PBS. Brain, heart, lung, liver, kidney and spinal cord were collected and snap frozen in liquid nitrogen and stored at −80° C. Sections of 8 or 30 μm were made on Thermo Scientific Microm HM 525. Before immunolabeling, sections were air dried for 1 hr, permeabilized with 0.05% saponin for 30 min, and blocked with PBSG for 30 min at RT. To visualize bound scFv-Fcs, sections were incubated with anti-rabbit AlexaFluor555-conjugated secondary antibody (Invitrogen #A21428), diluted 1:1000 in PBSG with 0.05% saponin, overnight at 4° C. Washing steps were with 0.05% saponin in PBS. Sections were mounted with ProLong Gold antifade reagent with DAPI (Invitrogen, P36935) and analyzed on a Zeiss Axio Imager Z2 Upright microscope. Additionally, 30 μm sections of injected mouse brain were immunolabeled for glial fibrillary acidic protein (GFAP) and collagen IV. After blocking with 10% goat or donkey serum, respectively and permeabilization as described previously, sections were incubated with either mouse anti-GFAP (BD Pharmingen #556329) or goat anti-collagen IV (Milipore Sigma #AB769) in the corresponding blocking buffer plus 0.05% saponin for 2 hrs at room temperature. Sections were washed with 0.05% saponin in PBS and incubated with secondary antibodies: anti-rabbit AlexaFluor555 (Invitrogen #A21428) and anti-mouse AlexaFluor647 (Invitrogen #A-21235) for GFAP detection or anti-rabbit AlexaFluor555 (Invitrogen #A31572) and anti-goat AlexaFluor647 (Invitrogen #A-21447) for collagen IV detection. Images were taken on Leica SP8 3×STED Confocal and processed with ImageJ.

Quantification of antibodies in mouse brains with ELISA: Mice C57BL6, 5-6 weeks old were injected intravenously with scFv-Fcs at a dose 20 mg/kg. After 1 hr, blood was sampled, briefly spun down and the plasma was frozen at −80° C. until analysis. After whole body perfusion at a rate 5 ml/min for 10 min with a PBS, supplemented with 100 U/ml heparin and 0.1% BSA, brains were removed. Next, to extract the accumulated antibody, brains were homogenized in 1% NP-40 in PBS with Complete Mini EDTA-free protease inhibitor cocktail tablets (Roche Diagnostics) as described previously (11). To allow the extraction of antibodies from the tissue, brains were rotated at 4° C. for 24 hrs. Supernatant was collected after centrifugation at 14,000 rpm for 20 min at 4° C. Brain extracts were either analyzed immediately or frozen at −80° C. No difference in the antibody brain concentration was observed in fresh or frozen samples.

Nunc Maxisorp 96-wells plates were coated with anti-HA tag antibody 1 μg/ml (Thermo Fisher Scientific #MA1-12429) diluted in 0.2 M $NaCO_3/NaHCO_3$ at 4° C. overnight. Plates were washed three times 5 min each with 0.05% Tween-20 in PBS and blocked with 2% BSA in washing buffer. Brain extracts were added undiluted to the plate and blood plasma samples were diluted in blocking buffer. Antibodies with known concentration were diluted in NP-40 brain extracts prepared from untreated mice exactly as described above and added in serial dilutions to construct the standard curve for calculation of brain concentrations. The standard curve to determine the terminal plasma concentration was constructed from known concentration antibodies diluted in blocking buffer. After 2 hrs incubation at RT the samples were aspirated, the plate was washed three times 5 min each and anti-rabbit HRP antibody (Sigma #A6154) was added for 1 hr at RT. The unbound detection antibody was washed six times 5 min each and 1-Step Ultra TMB-ELISA Substrate Solution (ThermoFisher Scientific #34028) was added. Absorbance was measured at 450 nm on Infinite M200 (Tecan) plate reader. The lower limit of detection in brain samples was 1.03 nM, 0.02 nM and 0.44 nM for clone 46.1, 17 and Ctrl-Fc, respectively. The plasma concentration for clones 46.1 and Ctrl was determined with ELISA and for clone 17 with Western Blot.

Temperature measurement in mice: Neurotensin (UniProtKB-Q9D3P9 (NEUT_MOUSE) was fused to the rabbit Fc region into a pIRES-rabbit Fe vector (44) via $(G4S)_2$ linker between customarily introduced BamHI and Notl restriction sites using standard cloning technique. ScFvs 46.1, and RBC36 were subcloned into the neurotensin containing vector as described earlier. The neurotensin antibody conjugates were produced and purified as described earlier. The activity of neurotensin was measured using PathHunter eXpress NTSR1 CHO-K1 (3-Arrestin GPCR assay (Eurofins, No. 93-0280E2CPOM) according to the manufacturer protocol.

Temperature measuring probe—loggers (Star Oddi, DST-nanoT) were implanted into the peritoneal cavity of C57BL6 mice (approx. 15 g) using aseptic technique. Mice were allowed to recover for 5 days. Analgesia was provided with Buprenorphine SR-Lab (Zoopharma) 1 mg/kg for 72 hours. ScFv-rabbitFc-neurotensin-antibody conjugates (20 mg/kg) or neurotensin (Sigma, No. N6383), dissolved in PBS (1 mg/kg) were injected into the retro-orbital sinus. Two days post injection mice were sacrificed, the loggers removed and the recordings registered.

Statistical Analyses: Statistical analysis was performed with two-tailed unpaired Students t test, p values<0.05 were considered statistically significant. For in vitro experiments, each lead antibody was compared directly to its appropriate control. For in vivo experiments, each lead antibody was directly compared with Ctrl-Fc to determine significance of brain uptake.

Results:

Phage Display Screening Using iPSC-Derived BMEC Model

A major challenge in phenotypic screens for antibodies capable of transcytosing the BBB is the inherent paracellular leakiness of most current BBB models. In the setting of a two compartment barrier model where a phage display antibody library is added to the blood side compartment (FIG. 1A, Step 3), paracellular leakiness will result in significant non-specific phage recovery in the brain side compartment masking potentially valuable, rare clones that actually had to traverse the BMECs by RMT. To address this longstanding challenge, we employed an iPSC-derived BMEC BBB model that combines the advantages of human-sourced material with robust barrier properties (18), which could in principle limit non-specific phage recovery. These BMECs express a collection of markers expressed by the BBB and a host of transporter proteins including nutrient transporters, drug efflux transporters, and large molecule RMT systems (17, 18) suggesting they could also be well suited for transporter-based screening (20, 21). Indeed, when irrelevant phage were applied to iPSC-derived BMEC monolayers varying in barrier quality as assessed by transendothelial electrical resistance (TEER), it was discovered that non-specific phage passage into the bottom well was very high in the traditional BBB model TEER range of 100-200 ohm-cm$^2$ (FIG. 1B). However, the irrelevant phage transport was greatly reduced above approximately 1000 ohm-cm$^2$, a range uniquely achieved by the human iPSC-based system. Thus, to avoid a large and deleterious background of phage, we used BMECs having a barrier of at least 1000 ohm-cm$^2$ for the transcytosis component of our screening procedure.

The entire screening procedure is illustrated in FIG. 1A. A library of $5\times10^8$ nonimmune human-derived scFvs displayed on the surface of fd-tet phage (22) was used for screening as multivalent display can help bias the screen towards antibodies capable of internalization (23), a requirement for transcytosis. First, a library pre-subtraction step was performed on human lung and heart endothelial cells (FIG. 1A, Step 1) in an attempt to de-enrich phage binding to common endothelial antigens and thereby gain BBB selectivity, as transcriptomics studies have shown a reasonably close relation between lung and heart cells to the BBB (24). Next, three screening rounds of BMEC binding and internalization were performed in order to enrich for scFvs having binding and internalization capacity, and to increase oversampling of such clones for the stringent transcytosis round. For these three rounds, $10^{11}$ phage from the presubtracted pool were incubated on BMECs, first on ice as a binding step and then at 37° C. to allow for phage internalization (FIG. 1A, Step 2). The surface of the BMEC monolayer was subsequently stripped of phage particles with low pH washes, cells were lysed, and internalized phage recovered in bacteria. After three rounds of binding and internalization, the phage pools were substantially enriched for BMEC-binding scFvs as measured by flow cytometry with the recovered phage pools (FIG. 1C). Next, in order to identify scFv-displaying phage capable of transcytosis across the BMEC monolayers, internalizing phage pools were added to the upper chamber of BMECs in a Transwell system and allowed to transcytose for 3 hours before phage recovery from the bottom chamber (FIG. 1A, Step 3*i*). A total of 220 phage clones were isolated from the bottom chamber (out of $10^{11}$ phage added), indicating the stringency of the screen. Phage immunochemistry on BMEC monolayers was performed to identify antibodies that truly interact with BMECs as opposed to non-specific phage that leaked through the monolayer, despite its substantial barrier (FIG. 1D). Upon sequencing, 12 unique scFvs were capable of binding to BMECs in phage display format. Moreover, it was observed that two clones, named 3 and 22Ch, represented>60% of the transcytosing phage pool (142/220 sequences, Table 1), and potentially masked the diversity by saturating the BMEC transcytosis capacity. Thus, to expand the diversity of scFvs recovered, scFv clones 3 and 22Ch were produced as soluble proteins and used to perform a competitive transcytosis screen. Soluble scFvs at saturating conditions were added to the upper chamber along with the internalizing phage antibody pools to reduce the interactions between phage displaying scFvs 3 and 22Ch and BMECs (FIG. 1A, step 3*ii*, and Materials and Methods). Individual phage clones accumulating in the bottom chamber were isolated and sequenced. Neither clone 3 nor 22Ch was found in the transcytosed fraction following soluble scFv competition, and the competitive transcytosis approach resulted in 10 more unique scFvs that bound to BMECs in phage display format, for a total of 22 lead scFvs.

TABLE 1

ScFv frequency from transcytosis screen.

| Number of unique scFv sequences | scFv sequence occurrence [%] |
|---|---|
| 1 (clone 3) | 38.2 |
| 1 (clone 22Ch) | 26.4 |
| 1 | 6.8 |

TABLE 1-continued

ScFv frequency from transcytosis screen.

| Number of unique scFv sequences | scFv sequence occurrence [%] |
|---|---|
| 1 | 2.7 |
| 1 | 1.4 |
| 3 | 0.9 |
| 48 | 0.4 |

ScFvs Internalize into BMECs and Bind to Human and Mouse Brain Microvessels

Figure 6:
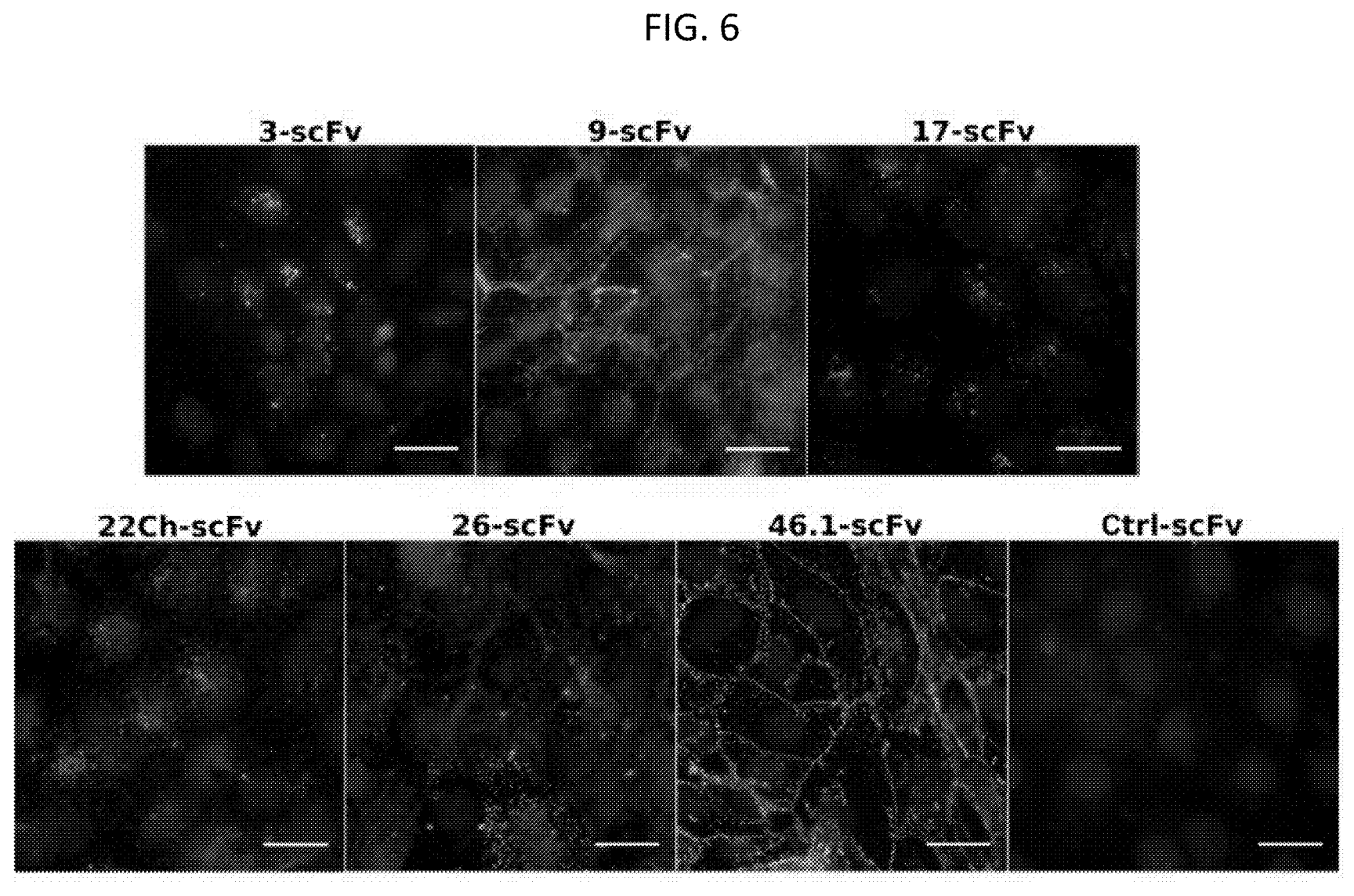

BMEC-binding scFvs identified from the transcytosis rounds were subcloned, bacterially expressed and purified. A total of 15 of the 22 scFvs could be produced at levels allowing downstream evaluation. After pulsing soluble scFvs onto BMECs, 12 out of the 15 scFvs bound to BMECs, with 10 also exhibiting clear internalization into BMECs (Table 2 and FIG. 6). For further evaluation, scFvs were reformatted as scFv-Fc fusions, expressed in HEK293F cells and purified (FIG. 2A). Six clones (3, 9, 26, 17, 46.1 and 22Ch) were produced in sufficient amounts for in vitro evaluation and subsequent in vivo assessment. As expected, scFv-Fc formatted antibodies migrated as dimers of ~100 kDa under non-reducing conditions (FIG. 2B). Apparent affinity ($K_D$) of scFv-Fcs for binding to BMEC monolayers was determined and ranged from 20-200 nM (FIG. 2C). To confirm that the reformatted scFv-Fc fusions retained their ability to bind and internalize into BMECs, scFv-Fcs were applied to BMECs. Each of the six assayed scFv-Fcs preserved their capacity to bind and internalize into BMECs (FIG. 2D). Five of six antibodies showed a similar binding and internalization appearance (clones 3, 9, 17, 22Ch, and 26). The surface bound antibodies were distributed across the BMEC surface (FIG. 2D, red), with the internalized antibodies found in puncta that were often perinuclear (FIG. 2D, green), reminiscent of intracellular vesicles. In striking contrast, the major fraction of internalized 46.1-scFv-Fc was trafficked to the cell-cell junctions. Quantitative internalization assays were performed with BMEC monolayers and five out of six clones tested exhibited a statistically significant, temperature dependent internalization, suggestive of endocytosis processes (FIG. 2E).

TABLE 2

Antibody attributes.

| Clone | Binding to BMECS | Internalization into BMECs | Binding to brain tissue human | Binding to brain tissue mouse | Target BBB after IV injection |
|---|---|---|---|---|---|
| 3 | Yes | Yes | Yes | Yes | Yes |
| 9 | Yes | Yes | Yes | Yes | No |
| 17 | Yes | Yes | Yes | Yes | Yes |
| 26 | Yes | Yes | Yes | Yes | Yes |
| 46.1 | Yes | Yes | Yes | Yes | Yes |
| 22Ch | Yes | Yes | Yes | No | No |
| 6i | Yes | No | No | ND | ND |
| 5A | Yes | Yes | No | ND | ND |
| 2F-scFv | Yes | Yes | Yes | Yes | ND |
| 4B-scFv | Yes | Yes | Yes | Yes | ND |
| 5E-0.4 | Yes | No | Yes | Yes | ND |
| B3-R3 | Yes | No | Yes | Yes | ND |

(ND—Not Determined)

Since in vitro modeling of the BBB can result in altered expression of surface receptors (25), the in vivo relevance in terms of the capacity of the identified antibodies to bind the BBB in brain tissue was next explored. First, the binding of scFvs to human brain sections was evaluated. Ten of twelve antibodies bind to their cognate antigens on human brain microvessels in tissue sections (FIG. 2F and Table 2). Given the need to perform pre-clinical evaluation, we also tested the antibody crossreactivity to mouse BBB antigens. Of the 10 scFvs with BBB binding in human sections, 9 also bound the mouse BBB (FIG. 2F and Table 2). Only those clones that could be produced in reasonable yields as scFv-Fcs and exhibited BMEC internalization and binding to both human and mouse BBB were evaluated further (3, 9, 26, 17, 46.1 and 22Ch).

Figure 3:
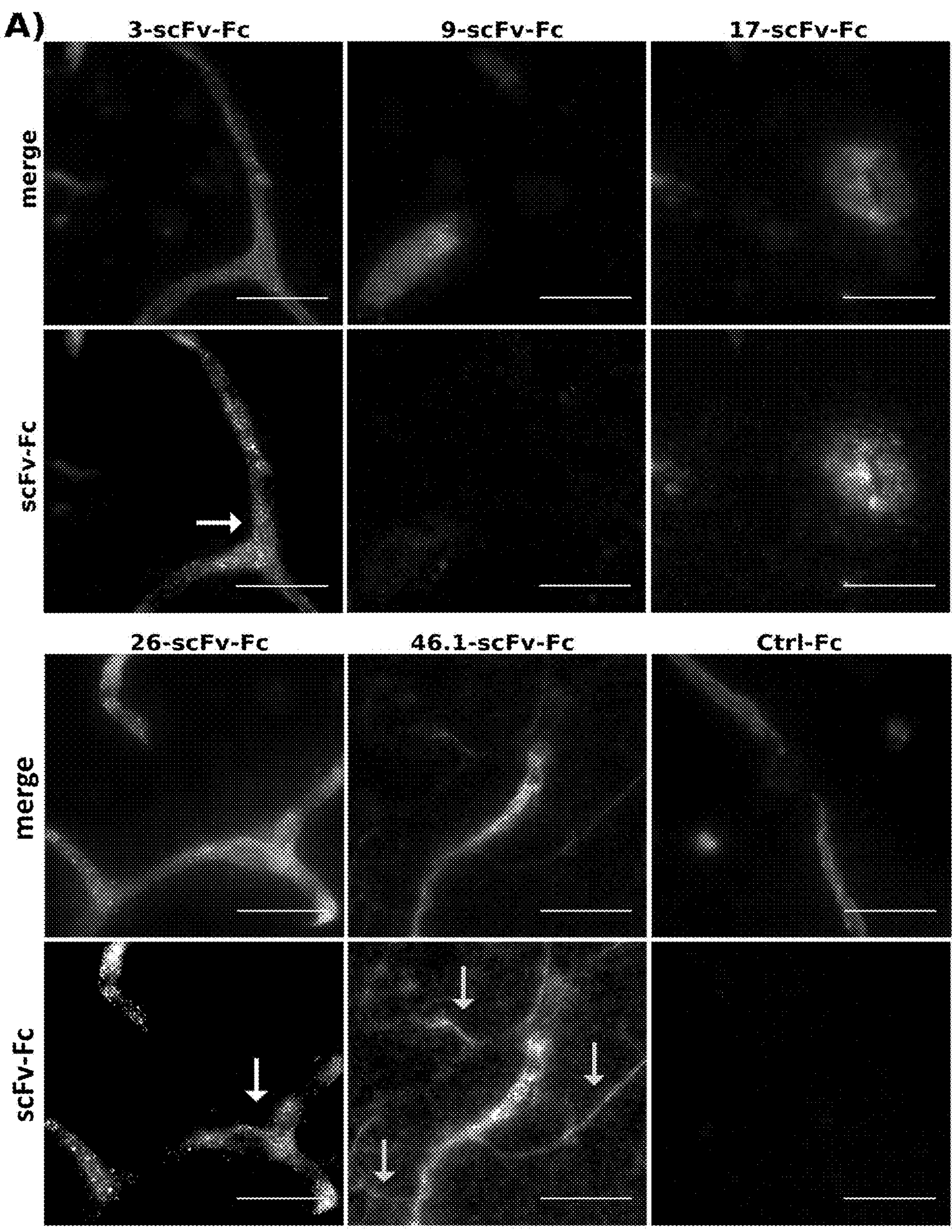
FIG. 3. Brain targeting of antibodies after intravenous administration in mice. (A) Antibodies (5 mg/kg) were injected intravenously in mice. One hour post-injection, mice were whole body perfused and brains collected. ScFv-Fcs (red) were labeled with fluorescent anti-rabbit Fc AlexaFluor555 antibody, blood vessels (green) were visualized with DyLight488 lectin that was present in the perfusion buffer. Four of five analyzed antibodies accumulate in brain vasculature as punctate structures in endothelial cells. Postvascular immunoreactivity was observed in the brain sections from mice injected with clone 46.1 (yellow arrows). Images were taken on an epifluorescence microscope. Scale bar, 20 μm. (B) Confocal images from a z-stack showing the localization of scFv-Fcs (red) with respect to collagen IV (blue). Blood vessels (green) as in A), nuclei (cyan). Clones 3, 26, and 46.1 colocalize with collagen IV (purple in merge and white arrows). Clone 17 shows no colocalization with collagen IV, but diffuse parenchymal staining was detected. (C) Co-localization of scFv-Fcs (red) and GFAP+ astrocytes (blue) can be observed in merged confocal images (purple). The yellow arrows in panels B) and C) indicate accumulation of antibodies in postvascular, GFAP-brain cells. In all panels, the grayscale images are included to assist evaluation of the individual channels depicted in the merged images. Scale bar, 20 μm.

Antibodies Accumulate in Brain Microvessels and Parenchyma after Intravenous Administration in Mice The scFv-Fcs that showed binding to brain microvessels in both human and mouse brain sections were next tested for brain targeting after intravenous administration. Mice were administered an intravenous scFv-Fc dose of 5 mg/kg, and the antibodies were allowed to circulate for 1 hour. The unbound antibody fraction was cleared from the blood vessels by whole body perfusion with a physiological saline solution. Perfusate also contained a fluorescently labeled lectin to visualize the lumen of the blood vessels. Following fixation, whole brains were removed and examined by immunohistochemistry. Immunohistochemical analysis of brain sections revealed that four of five injected antibodies target luminal BBB antigens (3, 17, 26 and 46.1, FIG. 3A). Clones 3—, 26- and 46.1-scFv-Fcs are visible as punctate structures (FIG. 3A, white arrows) resembling endocytic vesicles, suggesting receptor-mediated uptake in brain endothelial cells in vivo, while for clone 17, vascular labeling was slightly more diffuse (FIG. 3A). In addition, postvascular antibody was detected in 46.1 injected mice in perivascular processes associated with blood vessels (FIG. 3A, yellow arrow).

Given the appearance of transport through BBB endothelial cells, we further evaluated the antibody localization by confocal microscopy and co-localization with BBB basement membrane component, collagen IV (26), as an indicator of antibody transport from the blood side of the BBB endothelial cells to the brain side of the endothelial cells. Three-dimensional reconstructions of confocal Z-stack images indicated that three of the analyzed antibodies (3, 26 and 46.1) exhibit at least partial co-localization with the collagen IV, indicating antibody trafficking to the brain side of the BBB endothelium (FIG. 3B, white arrows, purple merge). By contrast, clone 17 does not exhibit co-localization with collagen IV, despite the fact that it could be consistently detected above background in the postvascular tissue and with some perinuclear localization associated with postvascular cells (FIG. 3B, yellow arrow).

As mentioned above, we frequently observed clone 46.1 in postvascular processes proximal to the microvessels (e.g., FIG. 3A, yellow arrows). To determine the cellular origin of these processes, we next labeled mouse brain sections with the astrocyte marker, glial fibrillary acidic protein (GFAP) (FIG. 3C). Clone 46.1 could be clearly identified as puncta associated with GFAP+ astrocyte processes (FIG. 3C). Astrocytes positive for 46.1-scFv-Fc were unevenly spread throughout the sagittal sections analyzed, with a tendency to occur most frequently in the hippocampal region. Other, unidentified CNS cells of non-vascular origin, also likely accumulate clone 46.1 (FIG. 3C, yellow arrow). Taken together, immunofluorescence suggests that clones 17 and 46.1 traffic across the BBB, with clone 46.1 exhibiting demonstrable postvascular association with perivascular astrocytes.

Figure 7:
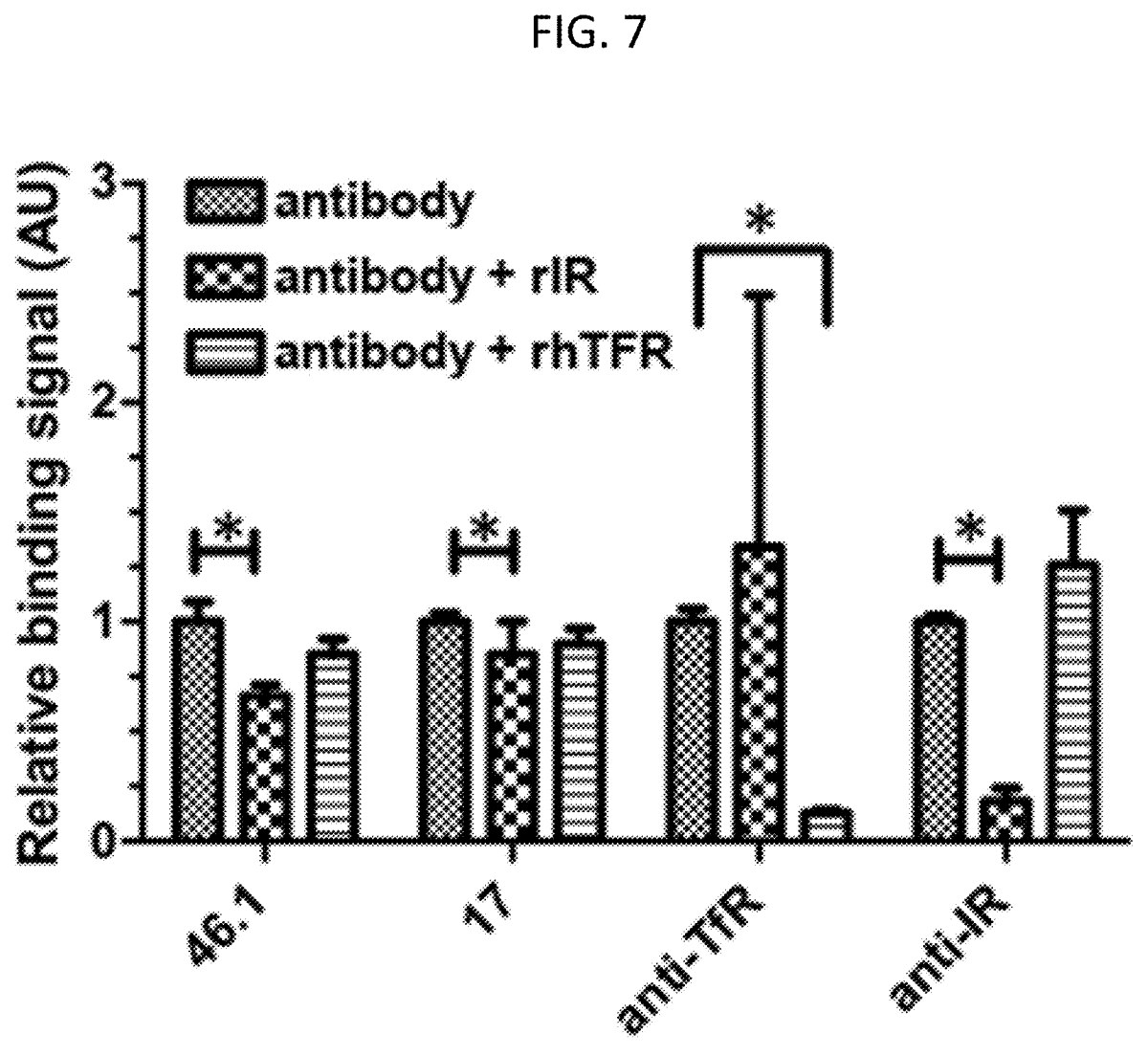

Given the capacity for clones 17 and 46.1 to cross the BBB, we investigated if they recognize the well-studied transferrin (TfR) or insulin receptors (IR). A competitive binding assay was used to determine if the scFv-Fcs interact substantially with TfR or IR by pre-incubating scFv-Fcs with excess recombinant receptor ectodomains before a cell surface binding assay. Cell surface binding of both clones 46.1 and 17 was not substantially reduced by either of the competing ligands (FIG. 7). Although there was a small decrease in both 17 and 46.1 binding in the presence of IR competition, it was quite small in comparison with the 80% reduction observed when anti-human IR control antibody was competed by soluble IR ectodomain. These data, along with the different trafficking patterns observed for 17 and 46.1, indicate that these two scFvs are not targeting TfR or IR.

Antibodies have Variable Biodistributions after Intravenous Administration

Figure 4:
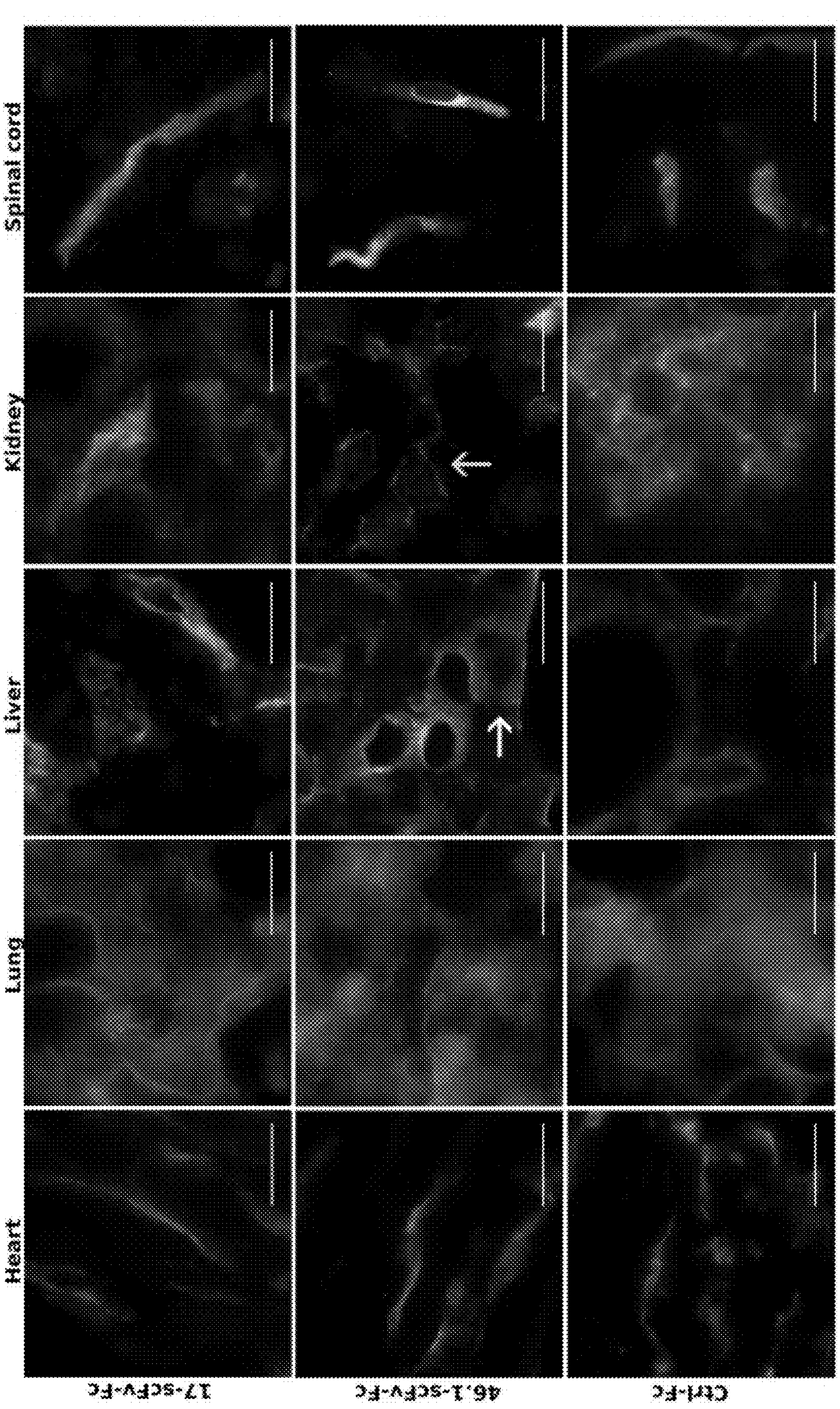
FIG. 4. Organ biodistribution of antibodies. Antibodies (5 mg/kg) were injected intravenously in mice. One hour post-injection, mice were whole body perfused and organs collected. ScFv-Fcs were immunolabeled with fluorescent anti-rabbit Fc AlexaFluor555 antibody (red), blood vessels were visualized with the perfused DyLight488 lectin (green). White and yellow arrows point junctional localization of clone 46.1 in hepatocytes and renal epithelial cells, respectively. Images were taken on an epifluorescence microscope. Scale bar, 20 μm.
Figure 8:
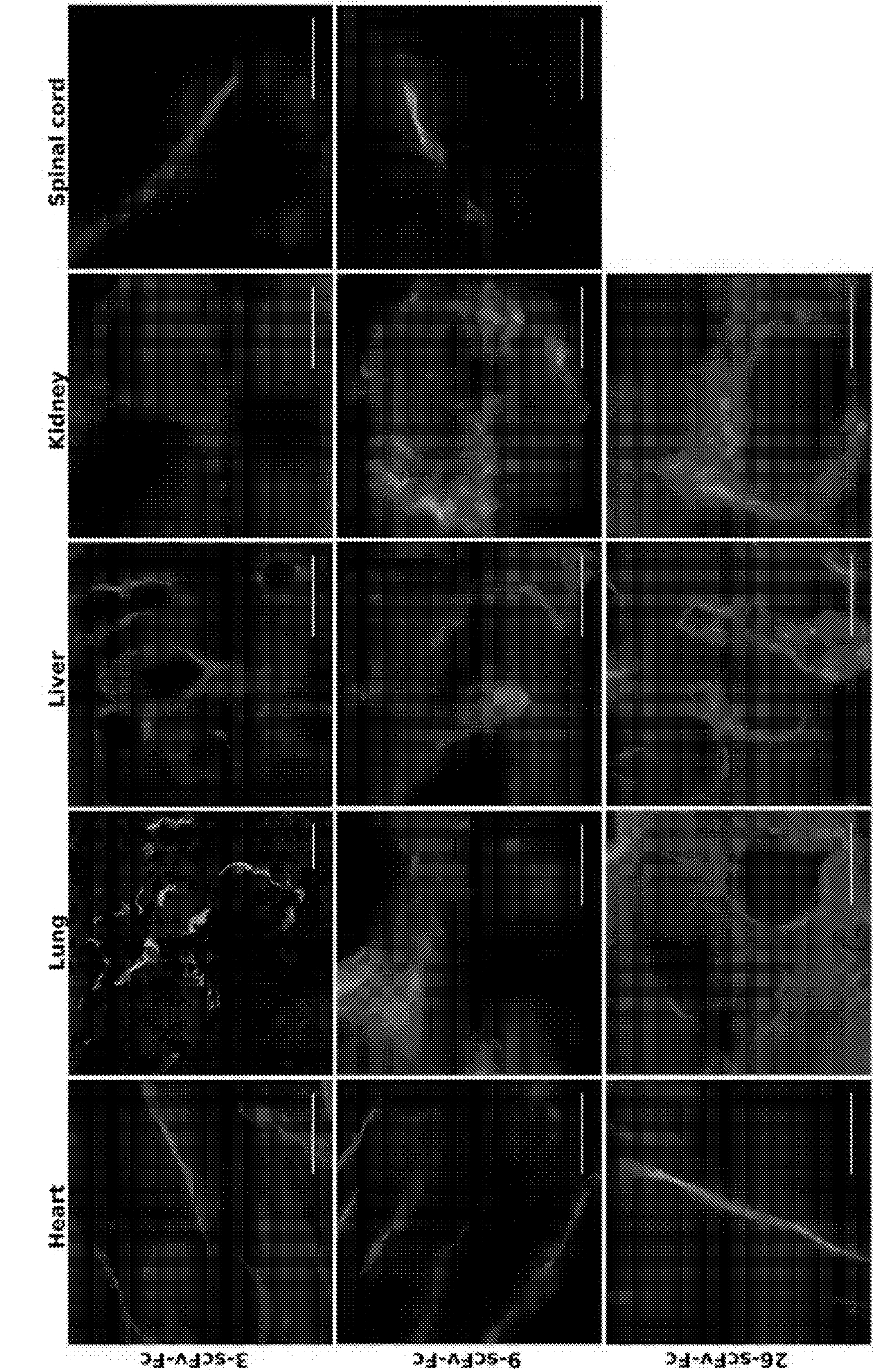
FIG. 8. Organ biodistribution of antibodies 3, 9 and 26. Antibodies were administered and detected as described in FIG. 4. ScFv-Fcs (red) and blood vessels (green) were visualized. Images were taken on epifluorescence microscope. Scale bar, 20 μm.

Given the pre-subtraction step that was built into the screen design (FIG. 1A), we also wished to assess the potential brain selectivity of candidate antibodies. To this end, antibody uptake was qualitatively assessed using immunohistochemistry. Antibody localization in heart and lung as highly vascularized organs as well as in liver and kidney as major clearance organs was assessed. Cervical and thoracic segments from the spinal cord were additionally analyzed for presence of antibodies. The qualitative analysis of organ biodistribution is summarized in Table 3 and representative images for the clones are shown in FIG. 4 and FIG. 8. Albeit with differences in tissue-specific cellular distribution, clone 3 and 17 were found in all analyzed organs. In contrast, clone 26 was not detected in heart, lung or kidney tissue (FIG. 4A). Clone 46.1 was not detected in heart microvasculature, showing at least partial selectivity to brain microvessels. Of particular interest with clone 46.1 was its cellular localization in liver and kidney, which suggested transcellular junctional trafficking in these organs. For instance, hepatocytes, like BBB endothelial cells, are polarized, with apical and basolateral membrane, segregated by tight junctions (27). Clone 46.1 could be found localizing at the cell-cell junctions of hepatocytes, (FIG. 4, white arrow). In addition, clone 46.1 could be found clearly localized at the cell-cell junctions of kidney tubular epithelial cells (FIG. 4, yellow arrow). Finally, we sought to determine whether antibodies could accumulate in the spinal cord. Clones 3, 9, 17 and 46.1 were found within the endothelial cells of capillaries penetrating the spinal cord, despite the fact that clone 9 did not bind BBB microvessels. Overall, the variable organ and tissue distribution of candidate antibodies points to different receptors engaged in their uptake and transport on both organ and cellular levels.

TABLE 3

Antibody organ biodistribution summary.

| Clone | Brain | Heart | Lung | Liver | Kidney | Spinal cord |
|---|---|---|---|---|---|---|
| 3-scFv-Fc | + | + | + | + | + | + |
| 9-scFv-Fc | − | − | − | + | − | + |
| 17-scFv-Fc | + | + | + | + | + | + |
| 26-scFv-Fc | + | − | − | + | − | ND |
| 46.1-scFv-Fc | + | − | + | + | + | + |
| Ctrl-Fc | − | − | − | − | − | − |

(+ positive, − negative, ND not determined)

Quantification of scFv-Fc Brain Accumulation after Intravenous Administration

Figure 5:
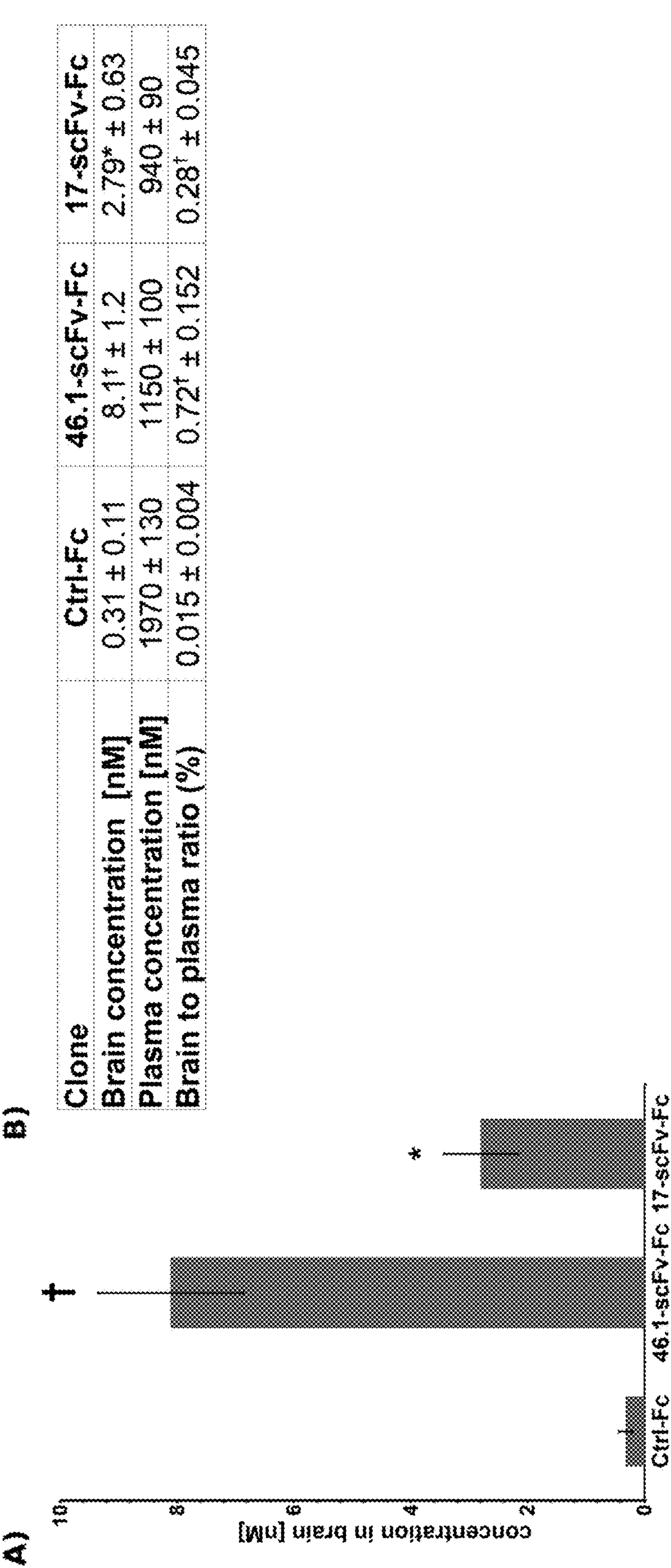
FIG. 5. Quantification of scFv-Fc brain accumulation. Clones 17 and 46.1 were intravenously injected into mice (n=4). After one hour, the mice were whole body perfused, brains collected and antibodies extracted. A) Concentration of antibodies in brain extracts were determined with ELISA as described in Materials and Methods. Reported are means±S.E.M., † p<0.005, * p<0.05 compared to Ctrl-Fc by two-tailed unpaired Students t test. B) Brain to plasma ratios were calculated from terminal plasma concentration of antibodies. Reported are means±S.E.M., *p<0.05, † p<0.005 compared to Ctrl-Fc by two-tailed unpaired Students t test.

Given the immunofluorescence analyses that indicated postvascular brain accumulation of clones 17 and 46.1, we further quantified their accumulation in whole mouse brain after intravenous administration. ScFv-Fcs at 20 mg/kg were injected and allowed to circulate for 1 hour. After whole body perfusion to remove the unbound antibodies from the vasculature, brains were isolated, homogenized and antibodies extracted. The concentration of antibodies in brain extracts (vascular-associated and parenchymal) was determined with ELISA (FIG. 5A). The measured concentration of clone 46.1 (8.1±1.2 nM) was 26-fold higher than that for negative control-Fc (0.31±0.11 nM). Clone 17 also accumulated in brain (2.79±0.63 nM), about 9-fold higher than control. Additionally, the antibody concentration in the terminal plasma was measured, and the brain concentrations were also expressed as a ratio to the plasma concentration (FIG. 5B), again indicating the selective uptake of clones 46.1 (0.72%) and 17 (0.28%) in the brain versus control (0.015%).

scFv-Fcs Deliver a Conjugated Payload Across the BBB

Figure 9:
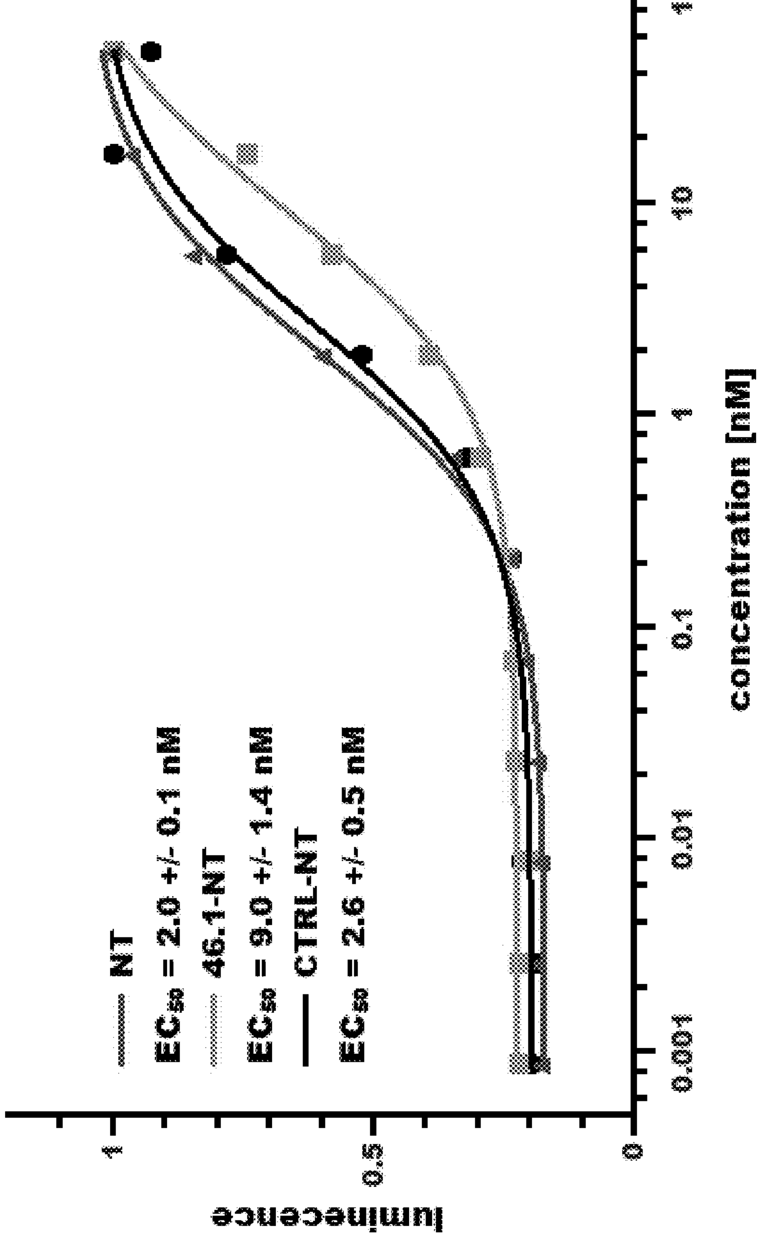
FIG. 9. Activity of neurotensin fused to the rabbit Fc region of antibodies. A reporter cell line expressing neurotensin receptor 1 was dosed with a range of concentrations of free neurotensin (NT), antibody bearing scFv-46.1 (46.1-NT), and control sequence coding variable lymphocyte receptor binding red blood cells antigen (CTRL-NT) and the activity of the receptor was plotted as a function of concentration.

To test whether the scFv-Fcs retain their ability to transverse the BBB after fusion to a molecular payload, scFv-46.1 was fused to neurotensin, the ligand for the cell surface receptor neurotensin receptor 1 (NTR1). The scFv-46.1-rabbitFc-neurotensin-antibody conjugate (neurotensin UniProtKB-Q9D3P9 (NEUT_MOUSE) sequence found at www.uniprot.org/uniprot/Q9D3P9 #PRO_0000019528) was shown to activate NTR1 in a reporter cell line expressing neurotensin receptor 1, although with lower affinity than either free neurotensin or neurotensin fused to a control Fc fusion (FIG. 9). When the scFv-46.1-rabbitFc-neurotensin-antibody conjugate was administered to mice via the retro-orbital sinus, a significant decrease in body temperature was observed spanning about one hour (FIG. 10), indicating the engagement of neurotensin receptor 1 on expressing neurons. By comparison, free neurotensin at 3-fold molar excess and control Fc neurotensin fusion did not yield a body temperature decrease over this same time frame. Thus, scFv-46.1 retains its ability to transverse the blood-brain barrier when it is conjugated to this ligand, demonstrating the potential of such antibodies for delivery of therapeutics to the brain.

DISCUSSION

In this study, we developed an original antibody screening strategy to identify antibodies that target human BBB antigens and also target and transcytose the murine BBB after systemic administration. Our functional screening strategy employed iPSC-derived BMEC-like cells as a screening substrate. Importantly, the paracellular tightness of this BBB model was key to limit the nonspecific accumulation of phage in the lower chamber, which would mask the recovery of clones that could truly transcytose across the BMECs. This stringent screening filter allowed for the identification of a panel of scFvs that upon further characterization led to a set of lead molecules capable of targeting and trafficking at the BBB in vivo. Although the iPSC-based BMEC-like model has been shown to have reasonable fidelity in modeling many BBB transport attributes (17, 18, 21), it cannot fully replicate all BBB functions (16, 19, 28). However, 10 of the 12 scFvs that bound to the BMECs also bound to the human BBB in tissue sections. By contrast, other screens using immortalized or primary BMEC substrates yield very few antibodies having in vivo relevance (29, 30). While the screening paradigm also included a pre-subtraction step on human lung and heart endothelial cells in an attempt to bias the screen towards BBB-selective antibodies, the biodistribution analyses indicated that the antibodies had a range of tissue selectivities. These data mirror other in vitro screening outcomes where pre-subtraction methods gave minimal advantage for in vivo selectivity of the lead molecules (14, 23, 30-32). These findings support the validity of the iPSC-BMEC system as a screening substrate, and along with the barrier properties of the model, the strategies described here may facilitate future efforts in identifying and engineering additional antibody-BBB transporter combinations.

Most of the scFvs (9 of 12) that were identified as binding to BMECs, also internalized, indicating that the internalization and transcytosis screening steps were enriching for endocytosing antibody-receptor combinations. The percentage of internalizing antibodies was much higher than other BBB screens using phage or yeast display libraries (29, 30). ScFvs interacted with the BMECs in a temperature-dependent fashion, and were found in intracellular punctae, suggesting RMT as the predominant route for cellular uptake. In particular, scFv 46.1 had a unique uptake pattern, namely there were few cytoplasmic 46.1-containing structures and most antibody could be found in punctae at the cell-cell junctions, seemingly distinct from recycling or degradative compartments (33, 34). While the identification of the receptor targeted by 46.1 is the focus of future work, we have not observed any literature describing such an antibody transport profile at the BBB. In addition to this unique intracellular distribution of internalized antibody, receptor ectodomain competition experiments indicated that the RMT target is not the transferrin or insulin receptors, suggesting that the 46.1-receptor system represents a new potential platform for brain delivery.

The potential of these new antibody-receptor pairs was further confirmed in vivo after intravenous administration. Four of five scFv-Fcs accumulated in mouse brain endothelium after one hour of circulation. Clones 3, 26 and 46.1 yielded a clear intracellular vesicular localization along the brain microvessels. Through collagen IV colocalization, it was apparent that each of these clones was also trafficked to the brain side of the brain endothelial cells. Once an antibody leaves the vasculature, it undergoes a rapid 1000-fold dilution, which hampers downstream postvascular detection (35). However, if the antibody also binds to a postvascular cell, like an astrocyte or neuron, it re-concentrates and can be readily detected (36, 37). In this way, it was possible to observe the postvascular accumulation of clone 46.1 where it was found associated with GFAP+ astrocyte foot processes and cell bodies. In addition, 46.1 was detected as punctae in GFAP− brain cells in the vicinity of 46.1-containing astrocytes. These findings gave clear evidence of full transcytosis of clone 46.1 across the BBB and its distribution in the brain parenchyma. Clone 17 did not co-localize with the vascular basement membrane. However, it could be observed reproducibly above background within the postvascular tissue compartment with occasional perinuclear association. Although not as clear as the 46.1 association with GFAP+ astrocytes, clone 17 also offers promise as a new antibody-receptor combination.

To benchmark the brain accumulation of clones 17 and 46.1, we next quantified the amount of antibody reaching the brain. After intravenous administration at 20 mg/kg, and one hour of circulation time, the brain concentration of clone 46.1 (8.1 nM, 0.72% brain/plasma) was 26-fold higher than control, and 9-fold higher for clone 17 (2.8 nM, 0.28% brain/plasma), respectively. These brain uptake levels are comparable to brain concentrations previously reported for engineered anti-transferrin antibodies (37-39). As in these comparative studies, the brain extracts were prepared from the whole tissue, including both the antibody in the brain parenchyma and that sequestered in the blood vessels endothelium. Combined with our immunofluorescence data, it is clear that within the one-hour time window, antibody is accumulating in postvascular brain tissue. Ultimately, antibody uptake levels are controlled by myriad factors (40) including antigen binding in non-target tissue, dose limitations, antibody affinity and avidity (6, 7, 34, 38, 41). For instance, given the fairly broad peripheral distribution of 46.1 into lung, liver and kidney, the specificity of conjugated drug payload will be a key consideration. Other BBB antibodies under development that target ubiquitously expressed receptors, including the TfR, also face similar challenges where payload choice and protein engineering need to be combined to maximize efficacy (7, 36, 38). Thus, antibody and payload engineering strategies will be important for the further development of the new antibody-receptor systems described here. In summary, we have identified new and promising antibodies that show substantial brain uptake, including postvascular accumulation. Importantly for translational considerations, our antibodies demonstrate cross-reactivity to mouse and human antigens. This work should enable the development of these lead antibodies as a platform to deliver therapeutics to the brain.

Sequences:

Synthetic - scFv3 AA:

(SEQ ID NO: 1)

QVQLQESGGGVVQPGRSLRLSCAASGFTFSSYAMHWVRQAPGKGLEWVAV*ISYDGSNK*YYAD

SVKGRFTISRDNSKNTLYLQMNSLRAEDTAVYYCARDSKGQSVRNRFDPWGQGTLVTVSSGGG

GSGGGGSGGGGSSELTQDPAVSVALGQTVRITCQGDNLRSYYASWYQQRPGQAPILVLY*AN*TH

RPSSIPDRFSGSSSGNTASLTITGAQAEDEADYYC*NSRDSSGNLVV*FGGGTKLTVLG

Synthetic - scFv9 AA:

(SEQ ID NO: 7)

QVQLVESGGGVTQPGLSLRLSCAASGFTFSSYAMSWVRQAPGKGLEWVSA*ISGSGGST*YYADS

VKGRFTISRDNSKNTLYLQMNSLRAEDTAVYYCARGWKYFDYWGQGTLVTVSSSGGGSGGGGS

GGGGSETTLTQSPSTLSASIGDRVAITCRASEGIYHWLAWYQQKPG*KA*PKLLIYKASSLASGA

PSRFSGSGSGTDFTLTISSLQPDDFATYYC*QQYHTISRT*FGPGTKVEIKR

-continued

Synthetic - scFv17 AA:

(SEQ ID NO: 13)

QVQLLQSAGALVQPGGSLRLSCAASGFTFSSSTMHWVRQAPGKGLEWVAVVSYDGNTQYYADS
VKGRFTISRDNSKNTLSLQMNNLRAEDTAVYYCAGLWGSLLGYFQHWGQGTLVTVSSGGGGSG
GGGSGGGGSDIQMTQSPSFLSASVGDRVTITCRASQGVNNYLAWYQQKPGKAPKLLIYAASTL
QSGVPSSFSGSGSGTEFTLTISSLQPEDFATYFCQQAHSFPPTFGGGTKLEIKR

Synthetic - scFv26 AA:

(SEQ ID NO: 19)

QVELVESGGGLVQPGGSLRLSCAASGFTFSTYWMNWVRQAPGKGLEWVAIINQDGTAEYYVDS
VEGRFTISRDNAKNSLYLQMTSLRVEDTAVYYCATPTGDSDYWGQGTLVTVSSGGGGSGGGGS
GGGGSSELTQDPAVSVALGQTVRITCQGDSLRSYYATWYQQKPGQAPVAVIYGQNNRPSGIPD
RFSGSNSGNTASLTITAALAEDEADYYCHSRDSSGNHVLFGGGTKLTVLG

Synthetic - scFv46.1 AA:

(SEQ ID NO: 25)

QVQLQESGGGLAQPGGSLRLSCAASGFTFSGYWMHWVRQAPGKGLVWVSRIKGDGTDIEYAD
SVKGRFTISRDNAKNTLYLQMNSLRAEDTAVYYCARDLRQTHWFDSWGQGTLVTVSSGGGGS
GGGGSGGGGSQSALTQDPAVSVALGQTVRITCQGDSLRSYYASWYQQKPGQAPVLVMYGENS
RPSGIPDRFSGSNSGNTASLIITGAQAEDEADYYCSSRDTSGNHVLFGGGTKLTVLG

Synthetic - scFv6i AA:

(SEQ ID NO: 31)

QVQLVESGGGLVQPGGSLRLSCAASGFTFSTYWMNWVRQAPGKGLEWVAIINQDGTAEYYVD
SVEGRFTISRDNAKNSLYLQMTSLRVEDTAVYYCATPTGDSDYWGQGTLVTVSSGGGGSGGGG
SGGGGSDIQMTQSPSTLSASIGDRVTITCQASQDIGNYLNWYQQKPGEAPKLLIYDASHLETG
VPSRFSGSGSGTEFTLTITGLQPEDFATYYCQKLSSYPLTFGGGTKLEIKR

Synthetic - scFv5A AA:

(SEQ ID NO: 37)

QVQLVESGGGLVQPGGSLRLSCAASGFTFSNYAMTWVRQAPGKGLEWVSAISGSGSSTYYADS
VKGRFTISRDNSKNTLYLQMNSLRAEDTAVYYCAKTSGWPYYFDYWGQGTLVTVSSGGGGSGG
GGSGGGGSQSVLTQPPSVSAAPGQKVTISCSGSSSNIGNNYVSWYQQFPGAAPKLLIYDNNKR
PSGIPDRFSGSKSGTSATLGITGLQTGDEADYYCCSYAGSSTLVFGGGTKXDRPR

Synthetic - scFv2F AA:

(SEQ ID NO: 43)

QVQLQESGGGLVQPGGSLRLSCAASGFTFSSYAMTWVRQVPGKGLEWVSTVSGTGVSTYYADS
VKGRFTISRDNSKNTLYLQMNSLRAEDTAIYYCARGLDWKSTPIDYWGQGTLVTVSSGGGGSG
GGGSGGGGSEIVLTQSPSTLSASVGDRVTITCRASQSISGWLAWYQQKPGKAPKLLIYGASSL
QSGVPSRFSGSGSGTDFTLTISGPQPEDSATYYCLQDYNGWTFGQGTKVEIKR

Synthetic - scFv4B AA:

(SEQ ID NO: 49)

QVQLQESGGGLIQPGGSLRLSCAASGFTVSSNYMSWVRQAPGKGLEWVANIKQDGSEKYYVDS
VKDRFTISRDNAKNSLDLQMNSLRAEDTALYYCARGGEEKNSGYYGDYWGQGTLVTVSSGGGG
SGGGGSGGGGSSELTQDPAVSVAVGQTVKITCQGDSLRSYYASWYRQKPGQSPVLVIYQDSKR
PSGIPERFSGSNSGNTATLTISGTQAMDEANYYCQAWDSSTAHYVFGTGTKVTVLG

Synthetic - scFv5E-0.4 AA:

(SEQ ID NO: 55)

QVQLQESGGGLVQPGGSLRLSCSASGFTFSSYVMGWVRQAPGKGLEWVSAISGSGGSTYYADS
VKGRFTISRDNSKNTVYLQMNSLRAEDTAVYYCAKQNWYFDLWGRGTLVTVSSGGGGSGGGG
SGGGGSSELTQDPAVSVALGQTVRITCQGDSLRSYYASWYQQKPGQAPVLVIYGENSRPSGIP
DRFSGSSSGNTASLTITGAQAEDEADYYCNSRDSRGTHLEVFGGRTKLTVLG

Synthetic - scFvB3-R3 AA:

-continued (SEQ ID NO: 61)

QVQLVESGGGVVQPGRSLRLSCAASGFTFSSYAMSWVRQAPGKGLEWVSA*ISGSGGST*YYADS

VMGRFTISRDNSKNTLYLQMDSLRAEDTAVYYCAKSQGWAGDFDFWGRGTLVTVSSGGGGSG

GGGSGGGGSQSALTQPPSASGSPGQSVTISCTGTSSDIGTYNYVSWYQQRPGYAPKLMIY*EV*N

KRPSGVPDRFSGSKSGNTASLTISGLQAEDEAEYHC*CSYAGSSTLV*FGGGTKLTVLG

Synthetic - scFv22Ch AA:

(SEQ ID NO: 67)

QVQLQESGGGVVQPGGSLRLSCSASGFTFSSYAMHWVRQAPGKGLEYVSA*ISSNGAIT*YYADS

VKGRFTISRDNSKNTLYLQMSSLSAEDTAVYYCVKDLKPSSWPPIYFDYWGQGTLVTVSSGGG

SGGGGGSGGGGSQSVLTQDPAVSVALGQTVKITCQGDSLRTYYASWYQQRPGQAPILVLY*AN*T

HRPSSIPDRFSGSSSGTTASLTITGAQAEDEADYYC*NSRDSSGNHHVV*FGGGTKLTVLG

REFERENCES

1. N. J. Abbott, A. Friedman, Overview and introduction: the blood-brain barrier in health and disease. *Epilepsia.* 53 Suppl 6, 1-6 (2012).
2. J. F. Poduslo, G. L. Curran, C. T. Berg, Macromolecular permeability across the blood-nerve and blood-brain barriers. *Proc. Natl. Acad. Sci. U.S.A* 91, 5705-5709 (1994).
3. A. R. Jones, E. V Shusta, Blood-brain barrier transport of therapeutics via receptor-mediation. *Pharm. Res.* 24, 1759-1771 (2007).
4. W. M. Pardridge, Y. S. Kang, J. L. Buciak, Transport of human recombinant brain-derived neurotrophic factor ({BDNF}) through the rat blood-brain barrier in vivo using vector-mediated peptide drug delivery. *Pharm. Res.* 11, 738-746 (1994).
5. W. M. Pardridge, Y. S. Kang, J. L. Buciak, J. Yang, Human insulin receptor monoclonal antibody undergoes high affinity binding to human brain capillaries in vitro and rapid transcytosis through the blood-brain barrier in vivo in the primate. *Pharm. Res.* 12, 807-816 (1995).
6. J. Niewoehner, B. Bohrmann, L. Collin, E. Urich, H. Sade, P. Maier, P. Rueger, J. O. Stracke, W. Lau, A. C. Tissot, H. Loetscher, A. Ghosh, P.-O. Freskgård, Increased brain penetration and potency of a therapeutic antibody using a monovalent molecular shuttle. Neuron. 81, 49-60 (2014).
7. J. A. Couch, Y. J. Yu, Y. Zhang, J. M. Tarrant, R. N. Fuji, W. J. Meilandt, H. Solanoy, R. K. Tong, K. Hoyte, W. Luk, Y. Lu, K. Gadkar, S. Prabhu, B. A. Ordonia, Q. Nguyen, Y. Lin, Z. Lin, M. Balazs, K. Scearce-Levie, J. A. Ernst, M. S. Dennis, R. J. Watts, Addressing safety liabilities of TfR bispecific antibodies that cross the blood-brain barrier. *Sci. Transl. Med.* 5, 183ra57, 1-12 (2013).
8. K. B. Johnsen, M. Bak, F. Melander, M. S. Thomsen, A. Burkhart, P. J. Kempen, T. L. Andresen, T. Moos, Modulating the antibody density changes the uptake and transport at the blood-brain barrier of both transferrin receptor-targeted gold nanoparticles and liposomal cargo. *J. Control. Release.* 295, 237-249 (2019).
9. L. I. Goulatis, E. V Shusta, Protein engineering approaches for regulating blood-brain barrier transcytosis. *Curr. Opin. Struct. Biol.* 45, 109-115 (2017).
10. C. C. Stutz, X. Zhang, E. V Shusta, Combinatorial approaches for the identification of brain drug delivery targets. *Curr. Pharm. Des.* 20, 1564-1576 (2014).
11. Y. J. Y. Zuchero, X. Chen, N. Bien-Ly, D. Bumbaca, R. K. Tong, X. Gao, S. Zhang, K. Hoyte, W. Luk, M. A. Huntley, L. Phu, C. Tan, D. Kallop, R. M. Weimer, Y. Lu, D. S. Kirkpatrick, J. A. Ernst, B. Chih, M. S. Dennis, R. J. Watts, Discovery of Novel Blood-Brain Barrier Targets to Enhance Brain Uptake of Therapeutic Antibodies. *Neuron.* 89, 70-82 (2016).
12. E. Urich, R. Schmucki, N. Ruderisch, E. Kitas, U. Certa, H. Jacobsen, C. Schweitzer, A. Bergadano, M. Ebeling, H. Loetscher, P. O. Freskgird, Cargo Delivery into the Brain by in vivo identified Transport Peptides. *Sci. Rep.* 5, 14104 (2015).
13. R. Pasqualini, E. Ruoslahti, Organ targeting in vivo using phage display peptide libraries. *Nature.* 380, 364-366 (1996).
14. A. Muruganandam, J. Tanha, S. Narang, D. Stanimirovic, Selection of phage-displayed llama single-domain antibodies that transmigrate across human blood-brain barrier endothelium. *FASEB J. Off Publ. Fed. Am. Soc. Exp. Biol.* 16, 240-242 (2002).
15. C. C. Stutz, J. V. Georgieva, E. V. Shusta, Coupling brain perfusion screens and next generation sequencing to identify blood-brain barrier binding antibodies. *AIChE J.* 64 (2018), doi:10.1002/aic.16360.
16. G. D. Vatine, A. Al-Ahmad, B. K. Barriga, S. Svendsen, A. Salim, L. Garcia, V. J. Garcia, R. Ho, N. Yucer, T. Qian, R. G. Lim, J. Wu, L. M. Thompson, W. R. Spivia, Z. Chen, J. Van Eyk, S. P. Palecek, S. Refetoff, E. V Shusta, C. N. Svendsen, Modeling Psychomotor Retardation using iPSCs from MCT8-Deficient Patients Indicates a Prominent Role for the Blood-Brain Barrier. *Cell Stem Cell.* 20, 831-843.e5 (2017).
17. E. S. Lippmann, S. M. Azarin, J. E. Kay, R. A. Nessler, H. K. Wilson, A. Al-Ahmad, S. P. Palecek, E. V Shusta, Derivation of blood-brain barrier endothelial cells from human pluripotent stem cells. *Nat. Biotechnol.* 30, 783-791 (2012).
18. E. S. Lippmann, A. Al-Ahmad, S. M. Azarin, S. P. Palecek, E. V Shusta, A retinoic acid-enhanced, multicellular human blood-brain barrier model derived from stem cell sources. *Sci. Rep.* 4, 4160 (2014).
19. T. Kurosawa, Y. Tega, K. Higuchi, T. Yamaguchi, T. Nakakura, T. Mochizuki, H. Kusuhara, K. Kawabata, Y. Deguchi, Expression and Functional Characterization of Drug Transporters in Brain Microvascular Endothelial Cells Derived from Human Induced Pluripotent Stem Cells. *Mol. Pharm.* 15, 5546-5555 (2018).
20. M. Ribecco-Lutkiewicz, C. Sodja, J. Haukenfrers, A. S. Haqqani, D. Ly, P. Zachar, E. Baumann, M. Ball, J. Huang, M. Rukhlova, M. Martina, Q. Liu, D. Stanimirovic, A. Jezierski, M. Bani-Yaghoub, A novel human induced pluripotent stem cell blood-brain barrier model:

Applicability to study antibody-triggered receptor-mediated transcytosis. *Sci. Rep.* 8, 1873 (2018).

21. M. J. Stebbins, H. K. Wilson, S. G. Canfield, T. Qian, S. P. Palecek, E. V Shusta, Differentiation and characterization of human pluripotent stem cell-derived brain microvascular endothelial cells. *Methods.* 101, 93-102 (2016).
22. M. D. Sheets, P. Amersdorfer, R. Finnern, P. Sargent, E. Lindquist, R. Schier, G. Hemingsen, C. Wong, J. C. Gerhart, J. D. Marks, E. Lindqvist, Efficient construction of a large nonimmune phage antibody library: the production of high-affinity human single-chain antibodies to protein antigens. *Proc. Natl. Acad. Sci. U.S.A* 95, 6157-6162 (1998).
23. M. A. Poul, B. Becerril, U. B. Nielsen, P. Morisson, J. D. Marks, Selection of tumor-specific internalizing human antibodies from phage libraries. *J. Mol. Biol.* 301, 1149-1161 (2000).
24. D. J. Nolan, M. Ginsberg, E. Israely, B. Palikuqi, M. G. Poulos, D. James, B.-S. Ding, W. Schachterle, Y. Liu, Z. Rosenwaks, J. M. Butler, J. Xiang, A. Rafii, K. Shido, S. Y. Rabbany, O. Elemento, S. Rafii, Molecular signatures of tissue-specific microvascular endothelial cell heterogeneity in organ maintenance and regeneration. *Dev. Cell.* 26, 204-219 (2013).
25. H. C. Helms, N. J. Abbott, M. Burek, R. Cecchelli, P.-O. Couraud, M. A. Deli, C. Förster, H. J. Galla, I. A. Romero, E. V Shusta, M. J. Stebbins, E. Vandenhaute, B. Weksler, B. Brodin, In vitro models of the blood-brain barrier: An overview of commonly used brain endothelial cell culture models and guidelines for their use. *J. Cereb. Blood Flow Metab.* 36, 862-890 (2016).
26. K. Kuhn, Basement membrane (type IV) collagen. *Matrix Biol.* 14, 439-45 (1995).
27. L. Wang, J. L. Boyer, The maintenance and generation of membrane polarity in hepatocytes. *Hepatology.* 39, 892-899 (2004).
28. L. Delsing, P. Dönnes, J. Sánchez, M. Clausen, D. Voulgaris, A. Falk, A. Herland, G. Brolen, H. Zetterberg, R. Hicks, J. Synnergren, Barrier Properties and Transcriptome Expression in Human iPSC-Derived Models of the Blood-Brain Barrier. *Stem Cells.* 36, 1816-1827 (2018).
29. X. X. Wang, Y. K. Cho, E. V Shusta, Mining a yeast library for brain endothelial cell-binding antibodies. *Nat. Methods.* 4, 143-145 (2007).
30. A. R. Jones, C. C. Stutz, Y. Zhou, J. D. Marks, E. V Shusta, Identifying blood-brain-barrier selective single-chain antibody fragments. *Biotechnol. J.* 9, 664-674 (2014).
31. J. Li, L. Feng, L. Fan, Y. Zha, L. Guo, Q. Zhang, J. Chen, Z. Pang, Y. Wang, X. Jiang, V. C. Yang, L. Wen, Targeting the brain with PEG-PLGA nanoparticles modified with phage-displayed peptides. *Biomaterials.* 32, 4943-4950 (2011).
32. M. Zorniak, P. A. Clark, B. J. Umlauf, Y. Cho, E. V Shusta, J. S. Kuo, Yeast display biopanning identifies human antibodies targeting glioblastoma stem-like cells. *Sci. Rep.* 7, 15840 (2017).
33. O. Ullrich, S. Reinsch, S. Urbé, M. Zerial, R. G. Parton, Rab 11 regulates recycling through the pericentriolar recycling endosome. *J. Cell Biol.* 135, 913-924 (1996).
34. A. S. Haqqani, G. Thom, M. Burrell, C. E. Delaney, E. Brunette, E. Baumann, C. Sodja, A. Jezierski, C. Webster, D. B. Stanimirovic, Intracellular sorting and transcytosis of the rat transferrin receptor antibody {OX}26 across the blood-brain barrier in vitro is dependent on its binding affinity. *J. Neurochem.* (2018), doi:10.1111/jnc.14482.
35. W. M. Pardridge, Blood-brain barrier drug delivery of IgG fusion proteins with a transferrin receptor monoclonal antibody. *Expert Opin. Drug Deliv.* 12 (2015), pp. 207-222.
36. Y. J. Yu, J. K. Atwal, Y. Zhang, R. K. Tong, K. R. Wildsmith, C. Tan, N. Bien-Ly, M. Hersom, J. A. Maloney, W. J. Meilandt, D. Bumbaca, K. Gadkar, K. Hoyte, W. Luk, Y. Lu, J. A. Ernst, K. Scearce-Levie, J. A. Couch, M. S. Dennis, R. J. Watts, Therapeutic bispecific antibodies cross the blood-brain barrier in nonhuman primates. *Sci. Transl. Med.* 6, 261ra154 (2014).
37. C. I. Webster, N. Caram-Salas, A. S. Haqqani, G. Thom, L. Brown, K. Rennie, A. Yogi, W. Costain, E. Brunette, D. B. Stanimirovic, Brain penetration, target engagement, and disposition of the blood-brain barrier-crossing bispecific antibody antagonist of metabotropic glutamate receptor type 1. *FASEB J.* 30, 1927-1940 (2016).
38. Y. J. Yu, Y. Zhang, M. Kenrick, K. Hoyte, W. Luk, Y. Lu, J. Atwal, J. M. Elliott, S. Prabhu, R. J. Watts, M. S. Dennis, Boosting brain uptake of a therapeutic antibody by reducing its affinity for a transcytosis target. *Sci. Transl. Med.* 3, 84ra44 (2011).
39. D. Karaoglu Hanzatian, A. Schwartz, F. Gizatullin, J. Erickson, K. Deng, R. Villanueva, C. Stedman, C. Harris, T. Ghayur, A. Goodearl, Brain uptake of multivalent and multi-specific DVD-Ig proteins after systemic administration. *MAbs.* 10, 765-777 (2018).
40. Y. Takakura, M. Hashida, Macromolecular carrier systems for targeted drug delivery: Pharmacokinetic considerations on biodistribution. *Pharm. Res.* 13, 820-831 (1996).
41. G. K. Farrington, N. Caram-Salas, A. S. Haqqani, E. Brunette, J. Eldredge, B. Pepinsky, G. Antognetti, E. Baumann, W. Ding, E. Garber, S. Jiang, C. Delaney, E. Boileau, W. P. Sisk, D. B. Stanimirovic, A novel platform for engineering blood-brain barrier-crossing bispecific biologics. *FASEB J.* 28, 4764-78 (2014).
42. D. O'Connell, B. Becerril, A. Roy-Burman, M. Daws, J. D. Marks, Phage versus Phagemid Libraries for Generation of Human Monoclonal Antibodies. *J Mol. Biol.* 321, 49-56 (2002).
43. Y. Zhou, J. D. Marks, in *Methods in molecular biology* (Clifton, N.J.) (2009; http://www.ncbi.nlm.nih.gov/pubmed/19252832), vol. 525, pp. 145-160.
44. B. J. Umlauf, P. A. Clark, J. M. Lajoie, J. V. Georgieva, S. Bremner, B. R. Herrin, J. S. Kuo, E. V. Shusta, Identification of variable lymphocyte receptors that can target therapeutics to pathologically exposed brain extracellular matrix. *Sci. Adv.* 5 (2019), doi:10.1126/sciadv.aau4245.
45. B. W. Han, B. R. Herrin, M. D. Cooper, I. A. Wilson, Antigen recognition by variable lymphocyte receptors. *Science* (80-.). 321, 1834-1837 (2008).

What is claimed:

1. A nucleic acid sequence encoding a blood-brain barrier (BBB)-selective antibody or antigen-binding fragment comprising:

(a) a heavy chain domain comprising a CDRH1 region comprising SEQ ID NO: 26 (GFTFSGYW), a CDHR2 region comprising SEQ ID NO: 27 (IKGDGTDI), and a CDHR3 region comprising SEQ ID NO: 28 (ARDLRQTHWFDS), and a light chain domain comprising CDRL1 region comprising SEQ ID NO: 29 (SLRSYY), a CDRL2 region comprising the amino acid sequence GE, and a CDRL3 comprising SEQ ID NO:30 (SSRDTSGNHVL);

(b) a heavy chain domain comprising a CDRH1 region comprising SEQ ID NO: 2 (GFTFSSYA), a CDHR2 region comprising SEQ ID NO: 3 (ISYDGSNK), and a CDHR3 region comprising SEQ ID NO: 4 (ARDSKGQSVRNRFDP), and a light chain domain comprising a CDRL1 region comprising SEQ ID NO: 5 (NLRSYY), a CDRL2 region comprising the amino acid sequence AN, and a CDRL3 comprising SEQ ID NO:6 (NSRDSSGNLVV);

(c) a heavy chain domain comprising a CDRH1 region comprising SEQ ID NO: 8 (GFTFSSYA), a CDHR2 region comprising SEQ ID NO: 9 (ISGSGGST), and a CDHR3 region comprising SEQ ID NO: 10 (ARGWKYFDY), and a light chain domain comprising a CDRL1 region comprising SEQ ID NO: 11 (EGIYHW), a CDRL2 region comprising the amino acid sequence KA, and a CDRL3 comprising SEQ ID NO: 12 (QQYHTISRT);

(d) a heavy chain domain comprising a CDRH1 region comprising SEQ ID NO: 14 (GFTFSSST), a CDHR2 region comprising SEQ ID NO: 15 (VSYDGNTQ), and a CDHR3 region comprising SEQ ID NO: 16 (AGLWGSLLGYFQH), and a light chain domain comprising a CDRL1 region comprising SEQ ID NO: 17 (QGVNNY), a CDRL2 region comprising the amino acid sequence AA, and a CDRL3 comprising SEQ ID NO: 18 (QQAHSFPPT);

(e) a heavy chain domain comprising a CDRH1 region comprising SEQ ID NO: 20 (GFTFSTYW), a CDHR2 region comprising SEQ ID NO: 21 (INQDGTAE), and a CDHR3 region comprising SEQ ID NO: 22 (ATPTGDSDY), and a light chain domain comprising a CDRL1 region comprising SEQ ID NO: 23 (SLRSYY), a CDRL2 region comprising the amino acid sequence GQ, and a CDRL3 comprising SEQ ID NO: 24 (HSRDSSGNHVL);

(f) a heavy chain domain comprising a CDRH1 region comprising SEQ ID NO: 32 (GFTFSTYW), a CDHR2 region comprising SEQ ID NO: 33 (INQDGTAE), and a CDHR3 region comprising SEQ ID NO: 34 (ATPTGDSDY), and a light chain domain comprising a CDRL1 region comprising SEQ ID NO: 35 (QDIGNY), a CDRL2 region comprising the amino acid sequence DA, and a CDRL3 comprising SEQ ID NO: 36 (QKLSSYPLT);

(g) a heavy chain domain comprising a CDRH1 region comprising SEQ ID NO: 38 (GFTFSNYA), a CDHR2 region comprising SEQ ID NO: 39 (ISGSGSST), and a CDHR3 region comprising SEQ ID NO: 40 (AKTSGWPYYFDY), and a light chain domain comprising a CDRL1 region comprising SEQ ID NO: 41 (SSNIGNNY), a CDRL2 region comprising the amino acid sequence DN, and a CDRL3 comprising SEQ ID NO: 42 (CSYAGSSTLV);

(h) a heavy chain domain comprising a CDRH1 region comprising SEQ ID NO: 44 (GFTFSSYA), a CDHR2 region comprising SEQ ID NO: 45 (VSGTGVST), and a CDHR3 region comprising SEQ ID NO: 46 (ARGLDWKSTPIDY), and a light chain domain comprising a CDRL1 region comprising SEQ ID NO: 47 (QSISGW), a CDRL2 region comprising the amino acid sequence GA, and a CDRL3 comprising SEQ ID NO: 48 (LQDYNGWT);

(i) a heavy chain domain comprising a CDRH1 region comprising SEQ ID NO: 50 (GFTVSSNY), a CDHR2 region comprising SEQ ID NO: 51 (IKQDGSEK), and a CDHR3 region comprising SEQ ID NO: 52 (ARGGEEKNSGYYGDY), and a light chain domain comprising a CDRL1 region comprising SEQ ID NO: 53 (SLRSYY), a CDRL2 region comprising the amino acid sequence QD, and a CDRL3 comprising SEQ ID NO: 54 (QAWDSSTAHYV);

(j) a heavy chain domain comprising a CDRH1 region comprising SEQ ID NO: 56 (GFTFSSYV), a CDHR2 region comprising SEQ ID NO: 57 (ISGSGGST), and a CDHR3 region comprising SEQ ID NO: 58 (AKQNWYFDL), and a light chain domain comprising a CDRL1 region comprising SEQ ID NO: 59 (SLRSYY), a CDRL2 region comprising the amino acid sequence GE, and a CDRL3 comprising SEQ ID NO: 60 (NSRDSRGTHLEV);

(k) a heavy chain domain comprising a CDRH1 region comprising SEQ ID NO: 62 (GFTFSSYA), a CDHR2 region comprising SEQ ID NO: 63 (ISGSGGST), and a CDHR3 region comprising SEQ ID NO: 64 (AKSQGWAGDFDF), and a light chain domain comprising a CDRL1 region comprising SEQ ID NO: 65 (SSDIGTYNY), a CDRL2 region comprising the amino acid sequence EV, and a CDRL3 comprising SEQ ID NO: 66 (CSYAGSSTLV); or (l) a heavy chain domain comprising a CDRH1 region comprising SEQ ID NO: 68 (GFTFSSYA), a CDHR2 region comprising SEQ ID NO: 69 (ISSNGAIT), and a CDHR3 region comprising SEQ ID NO: 70 (VKDLKPSSWPPIYFDY), and a light chain domain comprising a CDRL1 region comprising SEQ ID NO: 71 (SLRTYY), a CDRL2 region comprising the amino acid sequence AN, and a CDRL3 comprising SEQ ID NO: 72 (NSRDSSGNHHVV).

2. The nucleic acid sequence of claim 1, wherein the BBB-selective antibody or antigen-binding fragment comprises an amino acid sequence selected from:

(a) SEQ ID NO: 25 or a sequence having at least 90% identity to SEQ ID NO: 25;

(b) SEQ ID NO: 1 or a sequence having at least 90% identity to SEQ ID NO: 1;

(c) SEQ ID NO: 7 or a sequence having at least 90% identity to SEQ ID NO: 7;

(d) SEQ ID NO: 13 or a sequence having at least 90% identity to SEQ ID NO: 13;

(e) SEQ ID NO: 19 or a sequence having at least 90% identity to SEQ ID NO: 19;

(f) SEQ ID NO: 31 or a sequence having at least 90% identity to SEQ ID NO: 31;

(g) SEQ ID NO: 37 or a sequence having at least 90% identity to SEQ ID NO: 37;

(h) SEQ ID NO: 43 or a sequence having at least 90% identity to SEQ ID NO: 43;

(i) SEQ ID NO: 49 or a sequence having at least 90% identity to SEQ ID NO: 49;

(j) SEQ ID NO: 55 or a sequence having at least 90% identity to SEQ ID NO: 55;

(k) SEQ ID NO: 61 or a sequence having at least 90% identity to SEQ ID NO: 61; and (l) SEQ ID NO: 67 or a sequence having at least 90% identity to SEQ ID NO: 67.

3. The nucleic acid sequence of claim 1, wherein the BBB-selective antibody or antigen-binding fragment comprises an amino acid sequence selected from: (a) SEQ ID NO: 25; (b) SEQ ID NO: 1; (c) SEQ ID NO: 7; (d) SEQ ID NO: 13; (e) SEQ ID NO: 19; (f) SEQ ID NO: 31; (g) SEQ ID NO: 37; (h) SEQ ID NO: 43; (i) SEQ ID NO: 49; (j) SEQ ID NO: 55; (k) SEQ ID NO: 61; and (l) SEQ ID NO: 66.

4. The nucleic acid sequence of claim 1, wherein the BBB-selective antibody or antigen-binding fragment is a humanized antibody or humanized antigen-binding fragment thereof.

5. The nucleic acid of claim 1, wherein the BBB-selective antibody or antigen-binding fragment is engrafted within a full IgG scaffold of human or other species origin or a scFv scaffold of human or other species of origin.

6. The nucleic acid sequence of claim 1, wherein the BBB-selective antibody or antigen-binding fragment is a single chain variable fragment (scFv).

7. The nucleic acid sequence of claim 1, wherein the BBB-selective antibody or antigen-binding fragment can bind the BBB and translocate across the BBB.

8. The nucleic acid sequence of claim 1, wherein the BBB-selective antibody or antigen-binding fragment specifically binds to the brain.

9. The nucleic acid sequence of claim 1, wherein the nucleic acid is linked to a nucleic acid encoding an agent.

10. The nucleic acid of claim 9, wherein the agent is selected from the group consisting of a therapeutic agent, a pharmaceutical agent, a diagnostic agent, an imaging agent, a detection agent, an immunological therapeutic construct, and a combination thereof.

11. The nucleic acid sequence of claim 9, wherein the BBB-selective antibody or antigen-binding fragment and the agent are able to translocate the BBB.

12. A method of targeting a therapeutic agent to the BBB of a subject, the method comprising administering to the subject the nucleic acid sequence of claim 1, wherein the nucleic acid sequence encoding the BBB-selective antibody or antigen-binding fragment is linked to the therapeutic agent, and wherein the BBB-selective antibody or antigen-binding fragment thereof is able to specifically target and translocate the BBB.

13. The method of claim 12, wherein the agent is able to cross the BBB after targeting.

14. The method of claim 12, wherein the agent is able to accumulate at nM levels in the brain of the subject.

15. A kit comprising the nucleic acid sequence encoding the BBB-selective antibody or antigen-binding fragment of claim 1.

16. A vector comprising the nucleic acid sequence of claim 1.

17. A cell comprising the vector of claim 16.

18. A cell comprising the nucleic acid sequence of claim 1, wherein the cell is capable of expressing the BBB-selective antibody or antigen-binding fragment thereof.

* * * * *